US012595471B2

(12) United States Patent
Jenewein et al.

(10) Patent No.: US 12,595,471 B2
(45) Date of Patent: Apr. 7, 2026

(54) AMYLASE VARIANTS

(71) Applicant: BASF SE, Ludwigshafen (DE)

(72) Inventors: Stefan Jenewein, Ludwigshafen (DE);
Zachary David Miles, San Diego, CA
(US); Priya Anand, San Diego, CA
(US)

(73) Assignee: BASF SE, Ludwigshafen (DE)

( * ) Notice: Subject to any disclaimer, the term of this
patent is extended or adjusted under 35
U.S.C. 154(b) by 814 days.

(21) Appl. No.: 17/636,972

(22) PCT Filed: Aug. 21, 2020

(86) PCT No.: PCT/EP2020/073514
§ 371 (c)(1),
(2) Date: Feb. 21, 2022

(87) PCT Pub. No.: WO2021/032881
PCT Pub. Date: Feb. 25, 2021

(65) Prior Publication Data
US 2022/0267748 A1     Aug. 25, 2022

Related U.S. Application Data

(60) Provisional application No. 62/890,325, filed on Aug.
22, 2019, provisional application No. 62/905,893,
filed on Sep. 25, 2019, provisional application No.
62/930,806, filed on Nov. 5, 2019.

(51) Int. Cl.
*C12N 9/26* (2006.01)
*A21D 8/04* (2006.01)
*C11D 3/386* (2006.01)

(52) U.S. Cl.
CPC ........... *C12N 9/2414* (2013.01); *A21D 8/042*
(2013.01); *C11D 3/386* (2013.01); *C12Y*
*302/01001* (2013.01)

(58) Field of Classification Search
CPC ...... C12N 9/2414; A21D 8/042; C11D 3/386;
C11D 3/38681; C12Y 302/01001; Y02E
50/10
See application file for complete search history.

(56) References Cited

U.S. PATENT DOCUMENTS

| | | | |
|---|---|---|---|
| 9,670,436 B2 | 6/2017 | Jackson et al. | |
| 10,167,458 B2 | 1/2019 | Kaasgaard et al. | |
| 2012/0021485 A1 | 1/2012 | Power et al. | |
| 2016/0177238 A1 | 6/2016 | Jackson et al. | |
| 2016/0326506 A1 | 11/2016 | Kaasgaard et al. | |
| 2017/0015950 A1* | 1/2017 | Andersen ....... | C12Y 302/01001 |
| 2017/0166876 A1 | 6/2017 | Svendsen et al. | |

FOREIGN PATENT DOCUMENTS

| | | | |
|---|---|---|---|
| EP | 1781790 A2 | 5/2007 | |
| RU | 2469087 C2 | 12/2012 | |
| WO | WO-94/02597 A1 | 2/1994 | |
| WO | WO-94/18314 A1 | 8/1994 | |
| WO | WO-95/10603 A1 | 4/1995 | |
| WO | WO-96/23872 A1 | 8/1996 | |
| WO | WO-97/43424 A1 | 11/1997 | |
| WO | WO-99/19467 A1 | 4/1999 | |
| WO | WO-00/22103 A1 | 4/2000 | |
| WO | WO-00/60060 A2 | 10/2000 | |
| WO | WO-02/10355 A2 | 2/2002 | |
| WO | WO-02/068589 A2 | 9/2002 | |
| WO | WO-02/068597 A2 | 9/2002 | |
| WO | WO-03/83054 A2 | 10/2003 | |
| WO | WO-2004/091544 A2 | 10/2004 | |
| WO | WO-2005/001064 A2 | 1/2005 | |
| WO | WO-2006/002643 A2 | 1/2006 | |
| WO | WO-2006/066594 A2 | 6/2006 | |
| WO | WO-2008/080093 A2 | 7/2008 | |
| WO | WO-2009/061380 A2 | 5/2009 | |
| WO | WO-2009061378 A2 | 5/2009 | |
| WO | WO-2009/100102 A2 | 8/2009 | |
| WO | WO-2009/149130 A2 | 12/2009 | |
| WO | WO-2010/104675 A1 | 9/2010 | |
| WO | WO-2011/098531 A1 | 8/2011 | |
| WO | WO-2013/001078 A1 | 1/2013 | |
| WO | WO-2013/001087 A2 | 1/2013 | |
| WO | WO-2013/184577 A1 | 12/2013 | |
| WO | WO-2014/183921 A1 | 11/2014 | |
| WO | WO-2018/060216 A1 | 4/2018 | |
| WO | WO-2022/175435 A1 | 8/2022 | |

(Continued)

OTHER PUBLICATIONS

Banerjee et al., Improving enzymes for biomass conversion: A basic
research perspective. Bioenerg. Res., 2010, vol. 3: 82-92. (Year:
2010).*
Broun et al., Catalytic plasticity of fatty acid modification enzymes
underlying chemical diversity of plant lipids. Science, 1998, vol.
282: 1315-1317. (Year: 1998).*
Chica et al., Semi-rational approaches to engineering enzyme
activity: combining the benefits of directed evolution and rational
design. Curr. Opi. Biotechnol., 2005, vol. 16: 378-384. (Year:
2005).*
Devos et al., Practical limits of function prediction. Proteins:
Structure, Function, and Genetics. 2000, vol. 41: 98-107. (Year:
2000).*
Labes et al., Novel members of Glycoside hydrolase Family 13
derived from environmental DNA. Appl. Environ. Microbiol., 2008,
vol. 74(6); 1914-1921, (Year: 2008).*

(Continued)

*Primary Examiner* — Ganapathirama Raghu
(74) *Attorney, Agent, or Firm* — MARSHALL,
GERSTEIN & BORUN LLP

(57) ABSTRACT

Described herein are genetically engineered enzymes having
amylase enzyme activity, compositions comprising the
enzymes, and methods of making and using the enzymes.
The genetically engineered amylase enzymes are useful in
many different applications such as laundry detergents, dish
washing detergents, and cleaning products for homes, indus-
try, vehicle care, baking, animal feed, pulp and paper pro-
cessing, starch processing, brewing, and ethanol production.

18 Claims, 1 Drawing Sheet

Specification includes a Sequence Listing.

(56) References Cited

FOREIGN PATENT DOCUMENTS

| WO | WO-2024/033135 A2 | 2/2024 |
| WO | WO-2024/033136 A1 | 2/2024 |

OTHER PUBLICATIONS

Seffernick et al., Melamine deaminase and Atrazine chlorohydrolase: 98 percent identical but functionally different. J. Bacteriol., 2001, vol. 183 (8): 2405-2410. (Year: 2001).*

Sen et al., Developments in directed evolution for enzyme functions. Appl. Biochem. Biotechnol., 2007, vol. 143: 212-223. (Year: 2007).*

Van der Maarel et al., Properties and applications of starch-converting enzymes of a-amylase family. J. Biotechnol., 2002, vol. 94: 137-155 (Year: 2002).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

International Application No. PCT/EP2020/058129, International Search Report and Written Opinion, mailed Oct. 21, 2020.

EBI Accession No. GSP:AXQ16884, *Bacillus* sp. alpha-amylase mature mutant protein N272E (Oct. 1, 2009).

EBI Accession No. GSP: AQX15862, "*Bacillus* sp. alpha amylase AmyTS23 mutant protein N272E", (Oct. 1, 2019).

EBI Accession No. UNIPROT:A0A1V3FF02, SubName: Full= Alpha-amylase {ECO:0000313; EMBL:00E00238.1} (Jun. 7, 2017).

International Application No. PCT/EP2020/058130, International Search Report and Written Opinion, Oct. 21, 2020.

International Application No. PCT/EP2020/073514, International Search Report and Written Opinion, mailed Nov. 4, 2020.

EBI Accession No. GSP:BBX20349, *Bacillus* sp. nutritive polypeptide, SEQ ID 28761 (May 21, 2015).

EBI Accession No. GSP:BBX20889, Bacillus thuringiensis nutritive polypeptide, SEQ ID 29301, May 21, 2015.

Machius, et al., "Crystal Structure of Calcium-depletedBacillus licheniformis?-amylase at 2.2 Å Resolution", Journal of Molecular Biology, vol. 246, Issue 4, Mar. 3, 1995, pp. 545-559.

"Sequence 12 from U.S. Pat. No. 10,167,458", Database USPTO Proteins [Online], retrieved from EBI Database accession No. USPOP:QBD06052, XP002800786, Feb. 15, 2019, 1 page.

"Sequence 12 from U.S. Pat. No. 9,670,436", Database USPTO Proteins [Online], retrieved from EBI Database accession No. USPOP:AUE83821, XP002800787, Dec. 13, 2017, 01 page.

Sindhu, et al., "Molecular improvements in microbial ?-amylases for enhanced stability and catalytic efficiency", Bioresource Technology, vol. 245, Dec. 2017, pp. 1740-1748.

Egorov, et al., "Bacterial enzymes and antibiotic resistance", Acta Naturae, vol. 10, Issue 4, 2018, pp. 33-48.

* cited by examiner

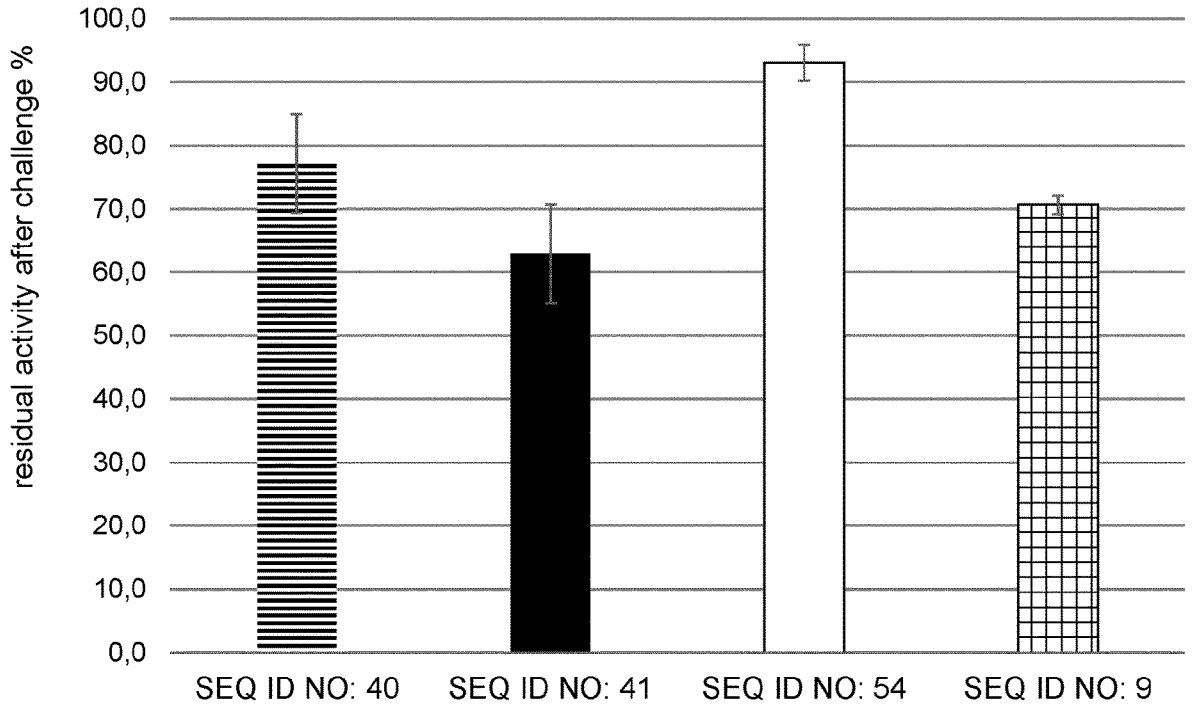

SEQUENCE LISTING

```
<160> NUMBER OF SEQ ID NOS: 56

<210> SEQ ID NO 1
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 1

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
            195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
            245                 250                 255

Lys Asn Met Phe Ala Val Ala Glu Phe Trp Lys Asn Asp Ile Gly Ala
```

-continued

```
              260              265              270

Ile Glu Asn Tyr Leu Ser Lys Thr Asn Trp Asn His Ser Val Phe Asp
         275              280              285

Val Pro Leu His Tyr Asn Leu Tyr Asn Ala Ser Arg Ser Gly Gly Asn
         290              295              300

Tyr Asp Met Arg Gln Ile Phe Asn Gly Thr Val Val Gln Arg His Pro
305              310              315              320

Thr His Ala Val Thr Phe Val Asp Asn His Asp Ser Gln Pro Glu Glu
             325              330              335

Ala Leu Glu Ser Phe Val Glu Glu Trp Phe Lys Pro Leu Ala Tyr Ala
             340              345              350

Leu Thr Leu Thr Arg Asp Gln Gly Tyr Pro Ser Val Phe Tyr Gly Asp
         355              360              365

Tyr Tyr Gly Ile Pro Thr His Gly Val Pro Ala Met Lys Ser Lys Ile
         370              375              380

Asp Pro Ile Leu Glu Ala Arg Gln Lys Tyr Ala Tyr Gly Thr Gln Arg
385              390              395              400

Asp Tyr Leu Asp His Pro Asp Val Ile Gly Trp Thr Arg Glu Gly Asp
             405              410              415

Ser Val His Ala Asn Ser Gly Leu Ala Thr Leu Met Ser Asp Gly Pro
             420              425              430

Gly Gly Ser Lys Trp Met Asp Val Gly Lys Asn Asn Ala Gly Glu Val
             435              440              445

Trp Arg Asp Ile Thr Gly Asn Gln Thr Asn Thr Val Thr Ile Asn Lys
         450              455              460

Asp Gly Trp Gly Gln Phe His Val Ser Gly Gly Ser Val Ser Ile Tyr
465              470              475              480

Val Gln Gln
```

```
<210> SEQ ID NO 2
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 2
catcacaatg gcacaaacgg taccatgatg caatattttg agtggtacct cccaaatgac      60
ggaaatcatt ggaacagatt gcgctctgat gcaagcaacc ttaaagataa gggcataaca     120
gctgtttgga ttccgccagc atggaaaggc gccagtcaaa cgacgtcgg atatggagcg      180 tacgatctgt atgatttagg cgagtttaat cagaaaggca cagtaagaac gaaatatgga     240
accaggaatc aacttcaggc ggctgtgacg gccctcaagt ctaatggcat tcaggtgtat     300
ggcgacgttg tgatgaacca caaaggagga gctgatgcga cagaatgggt tagagcagtc     360
gaagtaaatc ctagcaatcg aaaccaggag gtgagcggtg attacacaat cgaggcatgg     420
accaaattcg actttcctgg acgtggcaac acacatagta attttaagtg gagatggtat     480
cacttcgatg gcgtagactg ggatcaatct agacagttac agaaccggat ctacaaattt     540
cgcggaaaag gctgggattg ggaagttgat acggagaacg gcaattatga ttacttgatg     600
tacgcagata tcgacatgga tcatccggaa gtggtcaatg agttacgtaa ttggggcgtc     660
tggtacacta acacactggg ccttgacgga ttccgcattg atgcggttaa acatatcaaa     720 tattcgtta cgcgcgactg gttaactcat gtccggaata caacaggcaa gaatatgttt     780
```

-continued

```
gctgttgcag aattttggaa aaacgatatc ggcgcgattg aaaattatct ttcaaagact     840
aactggaatc attccgtatt cgacgtgcct ttgcactaca acctgtataa tgcgtcgcgc     900
tccggcggta actatgacat gcgacaaatc ttcaacggca cagtcgttca gcgtcacccc     960
acacacgctg ttacatttgt agacaaccat gacagccaac cggaggaagc tcttgaaagc    1020
ttcgtagaag aatggtttaa gcctctggcc tatgcgctga cgcttacgcg ggatcaagga    1080
tacccgagcg tgtttttatgg agattactat ggcattccga cgcatggcgt gccagccatg    1140
aaatcaaaaa ttgatccgat actcgaagcc agacaaaaat atgcatatgg tactcaacgg    1200
gattatttgg accatccgga tgtcattggt tggacccgtg aaggagatag cgtacatgct    1260
aactctggct tagccacact gatgtccgat ggtcctggag gctcaaaatg gatggatgtg    1320
ggtaagaaca atgcaggtga agtttggcgc gatattaccg gcaatcagac gaatacggtt    1380
actattaata aagatggttg gggacaattt catgtctcag gcggctctgt ctcaatctat    1440
gttcagcag                                                           1449
```

```
<210> SEQ ID NO 3
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 3
```

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
            115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240
```

```
Tyr Ser Phe Thr Arg Asp Trp Leu Thr His Val Arg Asn Thr Thr Gly
            245                 250                 255

Lys Asn Met Phe Ala Val Ala Glu Phe Trp Lys Asn Asp Ile Gly Ala
            260                 265                 270

Ile Glu Asn Tyr Leu Ser Lys Thr Asn Trp Asn His Ser Val Phe Asp
            275                 280                 285

Val Pro Leu His Tyr Asn Leu Tyr Asn Ala Ser Arg Ser Gly Gly Asn
        290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
            325                 330                 335

Ala Leu Glu Ser Phe Val Glu Glu Trp Phe Lys Pro Leu Ala Tyr Ala
            340                 345                 350

Leu Thr Leu Thr Arg Asp Gln Gly Tyr Pro Ser Val Phe Tyr Gly Asp
            355                 360                 365

Tyr Tyr Gly Ile Pro Thr His Gly Val Pro Ala Met Lys Ser Lys Ile
        370                 375                 380

Asp Pro Ile Leu Glu Ala Arg Gln Lys Tyr Ala Tyr Gly Thr Gln Arg
385                 390                 395                 400

Asp Tyr Leu Asp His Pro Asp Val Ile Gly Trp Thr Arg Glu Gly Asp
            405                 410                 415

Ser Val His Ala Asn Ser Gly Leu Ala Thr Leu Met Ser Asp Gly Pro
            420                 425                 430

Gly Gly Ser Lys Trp Met Asp Val Gly Lys Asn Asn Ala Gly Glu Val
            435                 440                 445

Trp Tyr Asp Ile Thr Gly Asn Gln Thr Asn Thr Val Thr Ile Asn Lys
        450                 455                 460

Asp Gly Trp Gly Gln Phe Gln Val Ser Gly Gly Ser Val Ser Ile Tyr
465                 470                 475                 480

Val Gln Arg
```

```
<210> SEQ ID NO 4
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 4
catcacaatg gcacaaacgg taccatgatg caatattttg agtggtacct cccaaatgac      60
ggaaatcatt ggaacagatt gcgctctgat gcaagcaacc ttaaagataa gggcataaca     120
gctgtttgga ttccgccagc atggaaaggc gccagtcaaa cgacgtcgg atatggagcg      180 tacgatctgt atgatttagg cgagtttaat cagaaaggca cagtaagaac gaaatatgga     240
accaggaatc aacttcaggc ggctgtgacg gccctcaagt ctaatggcat tcaggtgtat     300
ggcgacgttg tgatgaacca caaaggagga gctgatgcga cagaatgggt tagagcagtc     360
gaagtaaatc ctagcaatcg aaaccaggag gtgagcggtg attacacaat cgaggcatgg     420
accaaattcg actttcctgg acgtggcaac acacatagta attttaagtg agatatggtat    480 cacttcgatg gcgtagactg ggatcaatct agacagttac agaaccggat ctacaaattt     540
cgcggaaaag ctgggattgg gaagttgat acgagaacg gcaattatga ttacttgatg       600
tacgcagata tcgacatgga tcatccggaa gtggtcaatg agttacgtaa ttggggcgtc     660
```

```
tggtacacta acacactggg ccttgacgga ttccgcattg atgcggttaa acatatcaaa      720
tattcgttta cgcgcgactg gttaactcat gtccggaata caacaggcaa gaatatgttt      780
gctgttgcag aattttggaa aaacgatatc ggcgcgattg aaaattatct ttcaaagact      840
aactggaatc attccgtatt cgacgtgcct ttgcactaca acctgtataa tgcgtcgcgc      900
tccggcggta actatgacat gcgacaaatc ttcaacggca cagtcgttca gcgtcacccc      960
acacacgctg ttacatttgt agacaaccat gacagccaac cggaggaagc tcttgaaagc     1020
ttcgtagaag aatggtttaa gcctctggcc tatgcgctga cgcttacgcg ggatcaagga     1080
tacccgagcg tgttttatgg agattactat ggcattccga cgcatggcgt gccagccatg     1140
aaatcaaaaa ttgatccgat actcgaagcc agacaaaaat atgcatatgg tactcaacgg     1200
gattatttgg accatccgga tgtcattggt tggacccgtg aaggagatag cgtacatgct     1260
aactctggct tagccacact gatgtccgat ggtcctggag gctcaaaatg gatggatgtg     1320
ggtaagaaca atgcaggtga agtttggtat gatattaccg gcaatcagac gaatacggtt     1380
actattaata aagatggttg gggacaattt caggtctcag gcggctctgt ctcaatctat     1440
gttcagcgc                                                            1449
```

<210> SEQ ID NO 5
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 5

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220
```

-continued

```
Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
                245                 250                 255

Lys Asn Met Phe Ala Val Ala Glu Phe Trp Lys Asn Asp Ile Gly Ala
            260                 265                 270

Ile Glu Asn Tyr Leu Ser Lys Thr Asn Trp Asn His Ser Val Phe Asp
        275                 280                 285

Val Pro Leu His Tyr Asn Leu Tyr Asn Ala Ser Arg Ser Gly Gly Asn
    290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Asp Gln Gly Tyr Pro Ser Val Phe Tyr Gly Asp
        355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Thr Gln Arg
385                 390                 395                 400

Asp Tyr Leu Asp His Pro Asp Val Ile Gly Trp Thr Arg Glu Gly Asp
                405                 410                 415

Ser Val His Ala Asn Ser Gly Leu Ala Thr Leu Met Ser Asp Gly Pro
            420                 425                 430

Gly Gly Ala Lys Trp Met Asp Val Gly Lys Asn Asn Ala Gly Glu Ile
            435                 440                 445

Trp Tyr Asp Ile Thr Gly Asn Gln Thr Asn Thr Val Thr Ile Asn Lys
    450                 455                 460

Asp Gly Trp Gly Gln Phe Gln Val Ser Gly Gly Ser Val Ser Ile Tyr
465                 470                 475                 480

Val Gln Arg
```

```
<210> SEQ ID NO 6
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 6
catcacaatg gcacaaacgg taccatgatg caatattttg agtggtacct cccaaatgac      60
ggaaatcatt ggaacagatt gcgctctgat gcaagcaacc ttaaagataa gggcataaca     120
gctgtttgga ttccgccagc atggaaaggc gccagtcaaa acgacgtcgg atatggagcg     180
tacgatctgt atgatttagg cgagtttaat cagaaaggca cagtaagaac gaaatatgga     240
accaggaatc aacttcaggc ggctgtgacg gccctcaagt ctaatggcat tcaggtgtat     300
ggcgacgttg tgatgaacca caaaggagga gctgatgcga cagaatgggt tagagcagtc     360
gaagtaaatc ctagcaatcg aaaccaggag gtgagcggtg attacacaat cgaggcatgg     420
accaaattcg actttcctgg acgtggcaac acacatagta atttaagtg gagatggtat     480 cacttcgatg gcgtagactg ggatcaatct agacagttac agaaccggat ctacaaattt     540
```

-continued

```
cgcggaaaag gctgggattg ggaagttgat acggagaacg gcaattatga ttacttgatg      600
tacgcagata tcgacatgga tcatccggaa gtggtcaatg agttacgtaa ttggggcgtc      660
tggtacacta acacactggg ccttgacgga ttccgcattg atgcggttaa acatatcaaa      720
tattcgttta cgcgcgactg gttaactcat gtccggaata caacaggcaa gaatatgttt      780
gctgttgcag aattttggaa aaacgatatc ggcgcgattg aaaattatct ttcaaagact      840
aactggaatc attccgtatt cgacgtgcct ttgcactaca acctgtataa tgcgtcgcgc      900
tccggcggta actatgacat gcgacaaatc ttcaacggca cagtcgttca gcgtcacccc      960
acacacgctg ttacatttgt agacaaccat gacagccaac cggaggaagc tcttgaaagc     1020
ttcgtagaag aatggtttaa gcctctggcc tatgcgctga cgcttacgcg ggatcaagga     1080
tacccgagcg tgttttatgg agattactat ggcattccga cgcatggcgt gccagccatg     1140
aaatcaaaaa ttgatccgat actcgaagcc agacaaaaat atgcatatgg tactcaacgg     1200
gattatttgg accatccgga tgtcattggt tggacccgtg aaggagatag cgtacatgct     1260
aactctggct tagccacact gatgtccgat ggtcctggag gcgcgaaatg gatggatgtg     1320
ggtaagaaca atgcaggtga atctggtat gatattaccg gcaatcagac gaatacggtt     1380
actattaata aagatggttg gggacaattt caggtctcag gcggctctgt ctcaatctat     1440
gttcagcgc                                                             1449
```

```
<210> SEQ ID NO 7
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 7

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
```

```
                    195                 200                 205
Pro Glu Val Val Asn Glu Leu Arg Asn Trp Gly Val Trp Tyr Thr Asn
    210                 215                 220
Thr Leu Gly Leu Asp Gly Phe Arg Ile Asp Ala Val Lys His Ile Lys
225                 230                 235                 240
Tyr Ser Phe Thr Arg Asp Trp Leu Thr His Val Arg Asn Thr Thr Gly
                245                 250                 255
Lys Asn Met Phe Ala Val Ala Glu Phe Trp Lys Asn Asp Ile Gly Ala
                260                 265                 270
Ile Glu Asn Tyr Leu Ser Lys Thr Asn Trp Asn His Ser Val Phe Asp
                275                 280                 285
Val Pro Leu His Tyr Asn Leu Tyr Asn Ala Ser Arg Ser Gly Gly Asn
    290                 295                 300
Tyr Asp Met Arg Gln Ile Phe Asn Gly Thr Val Val Gln Arg His Pro
305                 310                 315                 320
Thr His Ala Val Thr Phe Val Asp Asn His Asp Ser Gln Pro Glu Glu
                325                 330                 335
Ala Leu Glu Ser Phe Val Glu Glu Trp Phe Lys Pro Leu Ala Tyr Ala
                340                 345                 350
Leu Thr Leu Thr Arg Asp Gln Gly Tyr Pro Ser Val Phe Tyr Gly Asp
                355                 360                 365
Tyr Tyr Gly Ile Pro Thr His Gly Val Pro Ala Met Lys Ser Lys Ile
    370                 375                 380
Asp Pro Ile Leu Glu Ala Arg Gln Lys Tyr Ala Tyr Gly Thr Gln Arg
385                 390                 395                 400
Asp Tyr Leu Asp His Pro Asp Val Ile Gly Trp Thr Arg Glu Gly Asp
                405                 410                 415
Gly Val His Ala Asp Ser Gly Leu Ala Thr Leu Met Ser Asp Gly Pro
                420                 425                 430
Gly Gly Ser Lys Trp Met Glu Val Gly Lys Asn Asn Ala Gly Glu Val
                435                 440                 445
Trp Tyr Asp Ile Thr Gly Asn Gln Thr Asn Thr Val Thr Ile Asn Lys
    450                 455                 460
Asp Gly Trp Gly Gln Phe His Val Ser Glu Gly Ser Val Ser Ile Tyr
465                 470                 475                 480
Val Gln Arg
```

<210> SEQ ID NO 8
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 8

```
catcacaatg gcacaaacgg taccatgatg caatattttg agtggtacct cccaaatgac    60
ggaaatcatt ggaacagatt gcgctctgat gcaagcaacc ttaaagataa gggcataaca   120
gctgtttgga ttccgccagc atggaaaggc gccagtcaaa cgacgtcgg atatggagcg    180 tacgatctgt atgatttagg cgagtttaat cagaaaggca cagtaagaac gaaatatgga   240
accaggaatc aacttcaggc ggctgtgacg gccctcaagt ctaatggcat tcaggtgtat   300
ggcgacgttg tgatgaacca caaaggagga gctgatgcga cagaatgggt tagagcagtc   360
gaagtaaatc ctagcaatcg aaaccaggag gtgagcggtg attacacaat cgaggcatgg   420
```

-continued

```
accaaattcg actttcctgg acgtggcaac acacatagta attttaagtg gagatggtat   480
cacttcgatg gcgtagactg ggatcaatct agacagttac agaaccggat ctacaaattt   540
cgcggaaaag gctgggattg ggaagttgat acggagaacg gcaattatga ttacttgatg   600
tacgcagata tcgacatgga tcatccggaa gtggtcaatg agttacgtaa ttggggcgtc   660
tggtacacta acacactggg ccttgacgga ttccgcattg atgcggttaa acatatcaaa   720
tattcgttta cgcgcgactg gttaactcat gtccggaata caacaggcaa gaatatgttt   780
gctgttgcag aattttggaa aaacgatatc ggcgcgattg aaaattatct ttcaaagact   840
aactggaatc attccgtatt cgacgtgcct ttgcactaca acctgtataa tgcgtcgcgc   900
tccggcggta actatgacat gcgacaaatc ttcaacggca cagtcgttca gcgtcacccc   960
acacacgctg ttacatttgt agacaaccat gacagccaac cggaggaagc tcttgaaagc   1020
ttcgtagaag aatggtttaa gcctctggcc tatgcgctga cgcttacgcg ggatcaagga   1080
tacccgagcg tgttttatgg agattactat ggcattccga cgcatggcgt gccagccatg   1140
aaatcaaaaa ttgatccgat actcgaagcc agacaaaaat atgcatatgg tactcaacgg   1200
gattatttgg accatccgga tgtcattggt tggacccgtg aaggagatgg agtacatgct   1260
gactctggct tagccacact gatgtccgat ggtcctggag gctcaaaatg gatggaagtg   1320
ggtaagaaca atgcaggtga agtttggtat gatattaccg gcaatcagac gaatacggtt   1380
actattaata aagatggttg gggacaattt catgtctcag aaggctctgt ctcaatctat   1440
gttcagcgc                                                            1449
```

```
<210> SEQ ID NO 9
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 9

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175
```

```
Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
            195                 200                 205

Pro Glu Val Val Asn Glu Leu Arg Asn Trp Gly Val Trp Tyr Thr Asn
            210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
            245                 250                 255

Lys Asn Met Phe Ala Val Ala Glu Phe Trp Lys Asn Asp Ile Gly Ala
            260                 265                 270

Ile Glu Asn Tyr Leu Ser Lys Thr Asn Trp Asn His Ser Val Phe Asp
            275                 280                 285

Val Pro Leu His Tyr Asn Leu Tyr Asn Ala Ser Arg Ser Gly Gly Asn
            290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
            325                 330                 335

Ala Leu Glu Ser Phe Val Glu Glu Trp Phe Lys Pro Leu Ala Tyr Ala
            340                 345                 350

Leu Thr Leu Thr Arg Asp Gln Gly Tyr Pro Ser Val Phe Tyr Gly Asp
            355                 360                 365

Tyr Tyr Gly Ile Pro Thr His Gly Val Pro Ala Met Lys Ser Lys Ile
            370                 375                 380

Asp Pro Ile Leu Glu Ala Arg Gln Lys Tyr Ala Tyr Gly Thr Gln Arg
385                 390                 395                 400

Asp Tyr Leu Asp His Pro Asp Val Ile Gly Trp Thr Arg Glu Gly Asp
            405                 410                 415

Ser Val His Ala Lys Ser Gly Leu Ala Thr Leu Met Ser Asp Gly Pro
            420                 425                 430

Gly Gly Ser Lys Trp Met Asp Val Gly Lys Asn Asn Ala Gly Glu Val
            435                 440                 445

Trp Tyr Asp Ile Thr Gly Asn Gln Thr Asn Thr Val Thr Ile Asn Lys
            450                 455                 460

Asp Gly Trp Gly Gln Phe His Val Ser Gly Gly Ser Val Ser Ile Tyr
465                 470                 475                 480

Val Gln Gln
```

```
<210> SEQ ID NO 10
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 10
catcacaatg gcacaaacgg taccatgatg caatattttg agtggtacct cccaaatgac        60
ggaaatcatt ggaacagatt gcgctctgat gcaagcaacc ttaaagataa gggcataaca       120
gctgtttgga ttccgccagc atggaaaggc gccagtcaaa cgacgtcgg atatggagcg       180 tacgatctgt atgatttagg cgagtttaat cagaaaggca cagtaagaac gaaatatgga       240
accaggaatc aacttcaggc ggctgtgacg gccctcaagt ctaatggcat tcaggtgtat       300
```

-continued

```
ggcgacgttg tgatgaacca caaaggagga gctgatgcga cagaatgggt tagagcagtc      360
gaagtaaatc ctagcaatcg aaaccaggag gtgagcggtg attacacaat cgaggcatgg      420
accaaattcg actttcctgg acgtggcaac acacatagta attttaagtg gagatggtat      480
cacttcgatg gcgtagactg ggatcaatct agacagttac agaaccggat ctacaaattt      540
cgcggaaaag gctgggattg ggaagttgat acggagaacg gcaattatga ttacttgatg      600
tacgcagata tcgacatgga tcatccggaa gtggtcaatg agttacgtaa ttggggcgtc      660
tggtacacta acacactggg ccttgacgga ttccgcattg atgcggttaa acatatcaaa      720
tattcgttta cgcgcgactg gttaactcat gtccggaata caacaggcaa gaatatgttt      780
gctgttgcag aattttggaa aaacgatatc ggcgcgattg aaaattatct ttcaaagact      840
aactggaatc attccgtatt cgacgtgcct ttgcactaca acctgtataa tgcgtcgcgc      900
tccggcggta actatgacat gcgacaaatc ttcaacggca cagtcgttca gcgtcacccc      960
acacacgctg ttacatttgt agacaaccat gacagccaac cggaggaagc tcttgaaagc     1020
ttcgtagaag aatggtttaa gcctctggcc tatgcgctga cgcttacgcg ggatcaagga     1080
tacccgagcg tgttttatgg agattactat ggcattccga cgcatggcgt gccagccatg     1140
aaatcaaaaa ttgatccgat actcgaagcc agacaaaaat atgcatatgg tactcaacgg     1200
gattatttgg accatccgga tgtcattggt tggacccgtg aaggagatag cgtacatgct     1260
aaatctggct tagccacact gatgtccgat ggtcctggag gctcaaaatg gatggatgtg     1320
ggtaagaaca atgcaggtga gtttggtat gatattaccg gcaatcagac gaatacggtt      1380
actattaata aagatggttg gggacaattt catgtctcag gcggctctgt ctcaatctat     1440
gttcagcag                                                             1449
```

<210> SEQ ID NO 11
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 11

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160
```

-continued

```
His Phe Asp Gly Val Asp Trp Asp Gln Ser Arg Gln Leu Gln Asn Arg
            165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
            195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
            245                 250                 255

Lys Asn Met Phe Ala Val Ala Glu Phe Trp Lys Asn Asp Ile Gly Ala
            260                 265                 270

Ile Glu Asn Tyr Leu Ser Lys Thr Asn Trp Asn His Ser Val Phe Asp
            275                 280                 285

Val Pro Leu His Tyr Asn Leu Tyr Asn Ala Ser Arg Ser Gly Gly Asn
    290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
            325                 330                 335

Ala Leu Glu Ser Phe Val Glu Glu Trp Phe Lys Pro Leu Ala Tyr Ala
            340                 345                 350

Leu Thr Leu Thr Arg Asp Gln Gly Tyr Pro Ser Val Phe Tyr Gly Asp
            355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Thr Gln Arg
385                 390                 395                 400

Asp Tyr Leu Asp His Pro Asp Val Ile Gly Trp Thr Arg Glu Gly Asp
            405                 410                 415

Gly Val His Ala Asp Ser Gly Leu Ala Thr Leu Met Ser Asp Gly Pro
            420                 425                 430

Glu Gly Ser Lys Trp Met Glu Val Gly Lys Asn Asn Ala Gly Glu Val
            435                 440                 445

Trp Tyr Asp Ile Thr Gly Asn Gln Thr Asn Thr Val Thr Ile Asn Lys
    450                 455                 460

Asp Gly Trp Gly Gln Phe His Val Ser Gly Gly Ser Val Ser Ile Tyr
465                 470                 475                 480

Val Gln Lys
```

```
<210> SEQ ID NO 12
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 12
catcacaatg gcacaaacgg taccatgatg caatattttg agtggtacct cccaaatgac       60
ggaaatcatt ggaacagatt gcgctctgat gcaagcaacc ttaaagataa gggcataaca      120
gctgtttgga ttccgccagc atggaaaggc gccagtcaaa acgacgtcgg atatggagcg      180
```

```
tacgatctgt atgatttagg cgagtttaat cagaaaggca cagtaagaac gaaatatgga      240
accaggaatc aacttcaggc ggctgtgacg gccctcaagt ctaatggcat tcaggtgtat      300
ggcgacgttg tgatgaacca caaaggagga gctgatgcga cagaatgggt tagagcagtc      360
gaagtaaatc ctagcaatcg aaaccaggag gtgagcggtg attacacaat cgaggcatgg      420
accaaattcg actttcctgg acgtggcaac acacatagta attttaagtg gagatggtat      480
cacttcgatg gcgtagactg ggatcaatct agacagttac agaaccggat ctacaaattt      540
cgcggaaaag gctgggattg ggaagttgat acggagaacg gcaattatga ttacttgatg      600
tacgcagata tcgacatgga tcatccggaa gtggtcaatg agttacgtaa ttggggcgtc      660
tggtacacta acacactggg ccttgacgga ttccgcattg atgcggttaa acatatcaaa      720
tattcgttta cgcgcgactg gttaactcat gtccggaata caacaggcaa gaatatgttt      780
gctgttgcag aattttggaa aaacgatatc ggcgcgattg aaaattatct ttcaaagact      840
aactggaatc attccgtatt cgacgtgcct ttgcactaca acctgtataa tgcgtcgcgc      900
tccggcggta actatgacat gcgacaaatc ttcaacggca cagtcgttca gcgtcacccc      960
acacacgctg ttacatttgt agacaaccat gacagccaac cggaggaagc tcttgaaagc     1020
ttcgtagaag aatggtttaa gcctctggcc tatgcgctga cgcttacgcg ggatcaagga     1080
tacccgagcg tgttttatgg agattactat ggcattccga cgcatggcgt gccagccatg     1140
aaatcaaaaa ttgatccgat actcgaagcc agacaaaaat atgcatatgg tactcaacgg     1200
gattatttgg accatccgga tgtcattggt tggacccgtg aaggagatgg agtacatgct     1260
gactctggct tagccacact gatgtccgat ggtcctgaag ctcaaaatg gatggaagtg      1320 ggtaagaaca atgcaggtga agtttggtat gatattaccg gcaatcagac gaatacggtt     1380
actattaata aagatggttg gggacaattt catgtctcag gcggctctgt ctcaatctat     1440
gttcagaaa                                                             1449
```

<210> SEQ ID NO 13
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 13

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
```

```
     130                135                140

Phe Pro Gly Arg Gly Asn Thr His Ser Asn Phe Lys Trp Arg Trp Tyr
145                150                155                160

His Phe Asp Gly Val Asp Trp Asp Gln Ser Arg Gln Leu Gln Asn Arg
              165                170                175

Ile Tyr Lys Phe Arg Gly Lys Gly Trp Asp Trp Glu Val Asp Thr Glu
              180                185                190

Asn Gly Asn Tyr Asp Tyr Leu Met Tyr Ala Asp Ile Asp Met Asp His
              195                200                205

Pro Glu Val Val Asn Glu Leu Arg Asn Trp Gly Val Trp Tyr Thr Asn
     210                215                220

Thr Leu Gly Leu Asp Gly Phe Arg Ile Asp Ala Val Lys His Ile Lys
225                230                235                240

Tyr Ser Phe Thr Arg Asp Trp Leu Thr His Val Arg Asn Thr Thr Gly
              245                250                255

Lys Asn Met Phe Ala Val Ala Glu Phe Trp Lys Asn Asp Ile Gly Ala
              260                265                270

Ile Glu Asn Tyr Leu Ser Lys Thr Asn Trp Asn His Ser Val Phe Asp
              275                280                285

Val Pro Leu His Tyr Asn Leu Tyr Asn Ala Ser Arg Ser Gly Gly Asn
     290                295                300

Tyr Asp Met Arg Gln Ile Phe Asn Gly Thr Val Val Gln Arg His Pro
305                310                315                320

Thr His Ala Val Thr Phe Val Asp Asn His Asp Ser Gln Pro Glu Glu
              325                330                335

Ala Leu Glu Ser Phe Val Glu Glu Trp Phe Lys Pro Leu Ala Tyr Ala
              340                345                350

Leu Thr Leu Thr Arg Asp Gln Gly Tyr Pro Ser Val Phe Tyr Gly Asp
              355                360                365

Tyr Tyr Gly Ile Pro Thr His Gly Val Pro Ala Met Lys Ser Lys Ile
     370                375                380

Asp Pro Ile Leu Glu Ala Arg Gln Lys Tyr Ala Tyr Gly Thr Gln Arg
385                390                395                400

Asp Tyr Leu Asp His Pro Asp Val Ile Gly Trp Thr Arg Glu Gly Asp
              405                410                415

Gly Val His Ala Gly Ser Gly Leu Ala Thr Leu Met Ser Asp Gly Pro
              420                425                430

Gly Gly Ser Lys Trp Met Glu Val Gly Glu Asn Asn Ala Gly Glu Val
              435                440                445

Trp Tyr Asp Ile Thr Gly Asn Gln Thr Asn Thr Val Thr Ile Asn Lys
     450                455                460

Asp Gly Trp Gly Gln Phe His Val Ser Gly Gly Ser Val Ser Ile Tyr
465                470                475                480

Val Gln Gln
```

<210> SEQ ID NO 14
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 14
catcacaatg gcacaaacgg taccatgatg caatattttg agtggtacct cccaaatgac      60

-continued

```
ggaaatcatt ggaacagatt gcgctctgat gcaagcaacc ttaaagataa gggcataaca        120
gctgtttgga ttccgccagc atggaaaggc gccagtcaaa acgacgtcgg atatggagcg        180
tacgatctgt atgatttagg cgagtttaat cagaaaggca cagtaagaac gaaatatgga        240
accaggaatc aacttcaggc ggctgtgacg gccctcaagt ctaatggcat tcaggtgtat        300
ggcgacgttg tgatgaacca caaaggagga gctgatgcga cagaatgggt tagagcagtc        360
gaagtaaatc ctagcaatcg aaaccaggag gtgagcggtg attacacaat cgaggcatgg        420
accaaattcg actttcctgg acgtggcaac acacatagta attttaagtg gagatggtat        480
cacttcgatg gcgtagactg ggatcaatct agacagttac agaaccggat ctacaaattt        540
cgcggaaaag gctgggattg ggaagttgat acggagaacg gcaattatga ttacttgatg        600
tacgcagata tcgacatgga tcatccggaa gtggtcaatg agttacgtaa ttggggcgtc        660
tggtacacta acacactggg ccttgacgga ttccgcattg atgcggttaa acatatcaaa        720
tattcgttta cgcgcgactg gttaactcat gtccggaata caacaggcaa gaatatgttt        780
gctgttgcag aattttggaa aaacgatatc ggcgcgattg aaaattatct ttcaaagact        840
aactggaatc attccgtatt cgacgtgcct ttgcactaca acctgtataa tgcgtcgcgc        900
tccggcggta actatgacat gcgacaaatc ttcaacggca cagtcgttca gcgtcacccc        960
acacacgctg ttacatttgt agacaaccat gacagccaac cggaggaagc tcttgaaagc       1020
ttcgtagaag aatggtttaa gcctctggcc tatgcgctga cgcttacgcg ggatcaagga       1080
tacccgagcg tgttttatgg agattactat ggcattccga cgcatggcgt gccagccatg       1140
aaatcaaaaa ttgatccgat actcgaagcc agacaaaaat atgcatatgg tactcaacgg       1200
gattatttgg accatccgga tgtcattggt tggacccgtg aaggagatgg agtacatgct       1260
ggctctggct tagccacact gatgtccgat ggtcctggag gctcaaaatg gatggaagtg       1320
ggtgaaaaca atgcaggtga gtttggtat gatattaccg gcaatcagac gaatacggtt        1380
actattaata aagatggttg gggacaattt catgtctcag gcggctctgt ctcaatctat       1440
gttcagcag                                                            1449
```

<210> SEQ ID NO 15
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 15

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110
```

```
Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
        130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
        180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
        210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
                245                 250                 255

Lys Asn Met Phe Ala Val Ala Glu Phe Trp Lys Asn Asp Ile Gly Ala
                260                 265                 270

Ile Glu Asn Tyr Leu Ser Lys Thr Asn Trp Asn His Ser Val Phe Asp
        275                 280                 285

Val Pro Leu His Tyr Asn Leu Tyr Asn Ala Ser Arg Ser Gly Gly Asn
        290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
                340                 345                 350

Leu Thr Leu Thr Arg Asp Gln Gly Tyr Pro Ser Val Phe Tyr Gly Asp
        355                 360                 365

Tyr Tyr Gly Ile Pro Thr His Gly Val Pro Ala Met Lys Ser Lys Ile
        370                 375                 380

Asp Pro Ile Leu Glu Ala Arg Gln Lys Tyr Ala Tyr Gly Thr Gln Arg
385                 390                 395                 400

Asp Tyr Leu Asp His Pro Asp Val Ile Gly Trp Thr Arg Glu Gly Asp
                405                 410                 415

Asp Val His Ala Asp Ser Gly Leu Ala Thr Leu Met Ser Asp Gly Pro
                420                 425                 430

Arg Gly Ser Lys Trp Met Glu Val Gly Lys Asn Asn Ala Gly Glu Val
        435                 440                 445

Trp Tyr Asp Ile Thr Gly Asn Gln Thr Asn Thr Val Thr Ile Asn Lys
        450                 455                 460

Asp Gly Trp Gly Gln Phe Arg Val Ser Gly Gly Ser Val Ser Ile Tyr
465                 470                 475                 480

Val Gln Gln
```

<210> SEQ ID NO 16
<211> LENGTH: 1449
<212> TYPE: DNA
<213> ORGANISM: Artificial Sequence
<220> FEATURE:
<223> OTHER INFORMATION: recombinant amylase variant

```
<400> SEQUENCE: 16
catcacaatg gcacaaacgg taccatgatg caatattttg agtggtacct cccaaatgac        60
ggaaatcatt ggaacagatt gcgctctgat gcaagcaacc ttaaagataa gggcataaca       120
gctgtttgga ttccgccagc atggaaaggc gccagtcaaa acgacgtcgg atatggagcg       180
tacgatctgt atgatttagg cgagtttaat cagaaaggca cagtaagaac gaaatatgga       240
accaggaatc aacttcaggc ggctgtgacg gccctcaagt ctaatggcat tcaggtgtat       300
ggcgacgttg tgatgaacca caaaggagga gctgatgcga cagaatgggt tagagcagtc       360
gaagtaaatc ctagcaatcg aaaccaggag gtgagcggtg attacacaat cgaggcatgg       420
accaaattcg actttcctgg acgtggcaac acacatagta attttaagtg gagatggtat       480
cacttcgatg gcgtagactg ggatcaatct agacagttac agaaccggat ctacaaattt       540
cgcggaaaag gctgggattg ggaagttgat acggagaacg gcaattatga ttacttgatg       600
tacgcagata tcgacatgga tcatccggaa gtggtcaatg agttacgtaa ttggggcgtc       660
tggtacacta acacactggg ccttgacgga ttccgcattg atgcggttaa acatatcaaa       720 tattcgtttta cgcgcgactg gttaactcat gtccggaata caacaggcaa gaatatgttt       780
gctgttgcag aattttggaa aaacgatatc ggcgcgattg aaaattatct ttcaaagact       840
aactggaatc attccgtatt cgacgtgcct ttgcactaca acctgtataa tgcgtcgcgc       900
tccggcggta actatgacat gcgacaaatc ttcaacggca cagtcgttca gcgtcacccc       960
acacacgctg ttacatttgt agacaaccat gacagccaac cggaggaagc tcttgaaagc      1020
ttcgtagaag aatggtttaa gcctctggcc tatgcgctga cgcttacgcg ggatcaagga      1080
tacccgagcg tgttttatgg agattactat ggcattccga cgcatggcgt gccagccatg      1140
aaatcaaaaa ttgatccgat actcgaagcc agacaaaaat atgcatatgg tactcaacgg      1200
gattatttgg accatccgga tgtcattggt tggacccgtg aaggagatga tgtacatgct      1260
gactctggct tagccacact gatgtccgat ggtcctcgcg ctcaaaatg gatggaagtg       1320 ggtaagaaca atgcaggtga agtttggtat gatattaccg gcaatcagac gaatacggtt      1380
actattaata aagatggttg gggacaattt cgcgtctcag gcggctctgt ctcaatctat      1440
gttcagcag                                                             1449

<210> SEQ ID NO 17
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 17

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95
```

```
Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
            115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
            195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
                245                 250                 255

Lys Asn Met Phe Ala Val Ala Glu Phe Trp Lys Asn Asp Ile Gly Ala
                260                 265                 270

Ile Glu Asn Tyr Leu Ser Lys Thr Asn Trp Asn His Ser Val Phe Asp
            275                 280                 285

Val Pro Leu His Tyr Asn Leu Tyr Asn Ala Ser Arg Ser Gly Gly Asn
    290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
                340                 345                 350

Leu Thr Leu Thr Arg Asp Gln Gly Tyr Pro Ser Val Phe Tyr Gly Asp
            355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Thr Gln His
385                 390                 395                 400

Asp Tyr Leu Asp His Pro Asp Val Ile Gly Trp Thr Arg Glu Gly Asp
                405                 410                 415

Ser Val His Ala Asn Ser Gly Leu Ala Thr Leu Met Ser Asp Gly Pro
                420                 425                 430

Gly Gly Ser Lys Trp Met Asp Val Gly Lys Asn Asn Ala Gly Glu Val
            435                 440                 445

Trp Tyr Asp Ile Thr Gly Asn Gln Thr Asn Thr Val Thr Ile Asn Lys
    450                 455                 460

Asp Gly Trp Gly Gln Phe Gln Val Ser Gly Gly Ser Val Ser Ile Tyr
465                 470                 475                 480

Val Gln Arg
```

<210> SEQ ID NO 18
<211> LENGTH: 1449
<212> TYPE: DNA

```
<213> ORGANISM: Artificial Sequence
<220> FEATURE:
<223> OTHER INFORMATION: recombinant amylase variant

<400> SEQUENCE: 18
catcacaatg gcacaaacgg taccatgatg caatattttg agtggtacct cccaaatgac      60
ggaaatcatt ggaacagatt gcgctctgat gcaagcaacc ttaaagataa gggcataaca     120
gctgtttgga ttccgccagc atggaaaggc gccagtcaaa acgacgtcgg atatggagcg     180
tacgatctgt atgatttagg cgagtttaat cagaaaggca cagtaagaac gaaatatgga     240
accaggaatc aacttcaggc ggctgtgacg gccctcaagt ctaatggcat tcaggtgtat     300
ggcgacgttg tgatgaacca caaaggagga gctgatgcga cagaatgggt tagagcagtc     360
gaagtaaatc ctagcaatcg aaaccaggag gtgagcggtg attacacaat cgaggcatgg     420
accaaattcg actttcctgg acgtggcaac acacatagta attttaagtg gagatggtat     480
cacttcgatg gcgtagactg ggatcaatct agacagttac agaaccggat ctacaaattt     540
cgcggaaaag gctgggattg ggaagttgat acggagaacg gcaattatga ttacttgatg     600
tacgcagata tcgacatgga tcatccggaa gtggtcaatg agttacgtaa ttgggggcgtc     660 tggtacacta acacactggg ccttgacgga ttccgcattg atgcggttaa acatatcaaa     720
tattcgttta cgcgcgactg gttaactcat gtccggaata caacaggcaa gaatatgttt     780
gctgttgcag aattttggaa aaacgatatc ggcgcgattg aaaattatct ttcaaagact     840
aactggaatc attccgtatt cgacgtgcct ttgcactaca acctgtataa tgcgtcgcgc     900
tccggcggta actatgacat cgacaaaatc ttcaacggca cagtcgttca gcgtcacccc     960
acacacgctg ttacatttgt agacaaccat gacagccaac cggaggaagc tcttgaaagc    1020
ttcgtagaag aatggtttaa gcctctggcc tatgcgctga cgcttacgcg ggatcaagga    1080
tacccgagcg tgtttttatgg agattactat ggcattccga cgcatggcgt gccagccatg    1140
aaatcaaaaa ttgatccgat actcgaagcc agacaaaaat atgcatatgg tactcaacat    1200
gattatttgg accatccgga tgtcattggt tggacccgtg aaggagatag cgtacatgct    1260
aactctggct tagccacact gatgtccgat ggtcctggag ctcaaaatg gatggatgtg     1320 ggtaagaaca atgcaggtga agtttggtat gatattaccg gcaatcagac gaatacggtt    1380
actattaata aagatggttg gggacaattt caggtctcag cggctctgt ctcaatctat    1440 gttcagcgc                                                            1449

<210> SEQ ID NO 19
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 19

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
```

```
65                    70                   75                   80
Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
               100                 105                 110

Ala Thr Glu Trp Val Arg Ala Val Glu Val Asn Pro Ser Asn Arg Asn
           115                 120                 125

Gln Glu Val Ser Gly Asp Tyr Thr Ile Glu Ala Trp Thr Lys Phe Asp
       130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
               180                 185                 190

Asn Gly Asn Tyr Asp Tyr Leu Met Tyr Ala Asp Ile Asp Met Asp His
               195                 200                 205

Pro Glu Val Val Asn Glu Leu Arg Asn Trp Gly Val Trp Tyr Thr Asn
       210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
                245                 250                 255

Lys Asn Met Phe Ala Val Ala Glu Phe Trp Lys Asn Asp Ile Gly Ala
                260                 265                 270

Ile Glu Asn Tyr Leu Ser Lys Thr Asn Trp Asn His Ser Val Phe Asp
           275                 280                 285

Val Pro Leu His Tyr Asn Leu Tyr Asn Ala Ser Arg Ser Gly Gly Asn
       290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
                340                 345                 350

Leu Thr Leu Thr Arg Asp Gln Gly Tyr Pro Ser Val Phe Tyr Gly Asp
           355                 360                 365

Tyr Tyr Gly Ile Pro Thr His Gly Val Pro Ala Met Lys Ser Lys Ile
       370                 375                 380

Asp Pro Ile Leu Glu Ala Arg Gln Lys Tyr Ala Tyr Gly Thr Gln Arg
385                 390                 395                 400

Asp Tyr Leu Asp His Pro Asp Val Ile Gly Trp Thr Arg Glu Gly Asp
                405                 410                 415

Ser Val His Ala Lys Ser Gly Leu Ala Ala Leu Met Ser Asp Gly Pro
                420                 425                 430

Gly Gly Ser Lys Trp Met Asp Val Gly Lys Asn Asn Ala Gly Glu Val
            435                 440                 445

Trp Tyr Asp Ile Thr Gly Asn Gln Thr Asn Thr Val Thr Ile Asn Lys
        450                 455                 460

Asp Gly Ser Gly Gln Phe His Val Ser Gly Gly Ser Val Ser Ile Tyr
465                 470                 475                 480

Val Gln Gln
```

-continued

<210> SEQ ID NO 20
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 20
catcacaatg gcacaaacgg taccatgatg caatattttg agtggtacct cccaaatgac      60
ggaaatcatt ggaacagatt gcgctctgat gcaagcaacc ttaaagataa gggcataaca     120
gctgtttgga ttccgccagc atggaaaggc gccagtcaaa acgacgtcgg atatggagcg     180
tacgatctgt atgatttagg cgagtttaat cagaaaggca cagtaagaac gaaatatgga     240
accaggaatc aacttcaggc ggctgtgacg gccctcaagt ctaatggcat tcaggtgtat     300
ggcgacgttg tgatgaacca caaaggagga gctgatgcga cagaatgggt tagagcagtc     360
gaagtaaatc ctagcaatcg aaaccaggag gtgagcggtg attacacaat cgaggcatgg     420
accaaattcg actttcctgg acgtggcaac acacatagta attttaagtg gagatggtat     480
cacttcgatg gcgtagactg ggatcaatct agacagttac agaaccggat ctacaaattt     540
cgcggaaaag gctgggattg ggaagttgat acggagaacg gcaattatga ttacttgatg     600
tacgcagata tcgacatgga tcatccggaa gtggtcaatg agttacgtaa ttggggcgtc     660
tggtacacta acacactggg ccttgacgga ttccgcatta tgcgggttaa acatatcaaa     720
tattcgttta cgcgcgactg gttaactcat gtccggaata caacaggcaa gaatatgttt     780
gctgttgcag aattttggaa aaacgatatc ggcgcgattg aaaattatct ttcaaagact     840
aactggaatc attccgtatt cgacgtgcct ttgcactaca acctgtataa tgcgtcgcgc     900
tccggcggta actatgacat cgacaaaatc ttcaacggca cagtcgttca gcgtcacccc     960
acacacgctg ttacatttgt agacaaccat gacagccaac cggaggaagc tcttgaaagc    1020
ttcgtagaag aatggtttaa gcctctggcc tatgcgctga cgcttacgcg ggatcaagga    1080
tacccgagcg tgttttatgg agattactat ggcattccga cgcatggcgt gccagccatg    1140
aaatcaaaaa ttgatccgat actcgaagcc agacaaaaat atgcatatgg tactcaacgg    1200
gattatttgg accatccgga tgtcattggt tggacccgtg aaggagatag cgtacatgct    1260
aaatctggct tagccgcgct gatgtccgat ggtcctggag ctcaaaatg gatggatgtg    1320 ggtaagaaca atgcaggtga gtttggtat gatattaccg gcaatcagac gaatacggtt    1380
actattaata aagatggtag cggacaattt catgtctcag gcggctctgt ctcaatctat   1440
gttcagcag                                                           1449

<210> SEQ ID NO 21
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 21

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

```
Lys Gly Ala Ser Gln Asn Asp Val Gly Tyr Gly Ala Tyr Asp Leu Tyr
    50              55              60

Asp Leu Gly Glu Phe Asn Gln Lys Gly Thr Val Arg Thr Lys Tyr Gly
65              70              75              80

Thr Arg Asn Gln Leu Gln Ala Ala Val Thr Ala Leu Lys Ser Asn Gly
            85              90              95

Ile Gln Val Tyr Gly Asp Val Val Met Asn His Lys Gly Gly Ala Asp
            100             105             110

Ala Thr Glu Trp Val Arg Ala Val Glu Val Asn Pro Ser Asn Arg Asn
            115             120             125

Gln Glu Val Ser Gly Asp Tyr Thr Ile Glu Ala Trp Thr Lys Phe Asp
    130             135             140

Phe Pro Gly Arg Gly Asn Thr His Ser Asn Phe Lys Trp Arg Trp Tyr
145             150             155             160

His Phe Asp Gly Val Asp Trp Asp Gln Ser Arg Gln Leu Gln Asn Arg
            165             170             175

Ile Tyr Lys Phe Arg Gly Lys Gly Trp Asp Trp Glu Val Asp Thr Glu
            180             185             190

Asn Gly Asn Tyr Asp Tyr Leu Met Tyr Ala Asp Ile Asp Met Asp His
            195             200             205

Pro Glu Val Val Asn Glu Leu Arg Asn Trp Gly Val Trp Tyr Thr Asn
    210             215             220

Thr Leu Gly Leu Asp Gly Phe Arg Ile Asp Ala Val Lys His Ile Lys
225             230             235             240

Tyr Ser Phe Thr Arg Asp Trp Leu Thr His Val Arg Asn Thr Thr Gly
            245             250             255

Lys Asn Met Phe Ala Val Ala Glu Phe Trp Lys Asn Asp Ile Gly Ala
            260             265             270

Ile Glu Asn Tyr Leu Ser Lys Thr Asn Trp Asn His Ser Val Phe Asp
            275             280             285

Val Pro Leu His Tyr Asn Leu Tyr Asn Ala Ser Arg Ser Gly Gly Asn
    290             295             300

Tyr Asp Met Arg Gln Ile Phe Asn Gly Thr Val Val Gln Arg His Pro
305             310             315             320

Thr His Ala Val Thr Phe Val Asp Asn His Asp Ser Gln Pro Glu Glu
            325             330             335

Ala Leu Glu Ser Phe Val Glu Glu Trp Phe Lys Pro Leu Ala Tyr Ala
            340             345             350

Leu Thr Leu Thr Arg Asp Gln Gly Tyr Pro Ser Val Phe Tyr Gly Asp
            355             360             365

Tyr Tyr Gly Ile Pro Thr His Gly Val Pro Ala Met Lys Ser Lys Ile
    370             375             380

Asp Pro Ile Leu Glu Ala Arg Gln Lys Tyr Ala Tyr Gly Thr Gln Arg
385             390             395             400

Asp Tyr Leu Asp His Pro Asp Val Ile Gly Trp Thr Arg Glu Gly Asp
            405             410             415

Gly Val His Ala Asn Ser Gly Leu Ala Ala Leu Met Ser Asp Gly Pro
            420             425             430

Gly Gly Ser Lys Trp Met Asp Val Gly Lys Asn Asn Ala Gly Glu Val
            435             440             445

Trp Tyr Asp Ile Thr Gly Asn Gln Thr Asn Thr Val Thr Ile Asn Lys
    450             455             460

Asp Gly Trp Gly Gln Phe His Val Asn Gly Gly Ser Ala Ser Ile Tyr
```

-continued

```
465            470            475            480

Ile Gln Gln

<210> SEQ ID NO 22
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 22
catcacaatg gcacaaacgg taccatgatg caatattttg agtggtacct cccaaatgac      60
ggaaatcatt ggaacagatt gcgctctgat gcaagcaacc ttaaagataa gggcataaca     120
gctgtttgga ttccgccagc atggaaaggc gccagtcaaa cgacgtcgg atatggagcg      180 tacgatctgt atgatttagg cgagtttaat cagaaaggca cagtaagaac gaaatatgga     240
accaggaatc aacttcaggc ggctgtgacg gccctcaagt ctaatggcat tcaggtgtat     300
ggcgacgttg tgatgaacca caaaggagga gctgatgcga cagaatgggt tagagcagtc     360
gaagtaaatc ctagcaatcg aaaccaggag gtgagcggtg attacacaat cgaggcatgg     420
accaaattcg actttcctgg acgtggcaac acacatagta attttaagtg gagatggtat     480
cacttcgatg gcgtagactg ggatcaatct agacagttac agaaccggat ctacaaattt     540
cgcggaaaag gctgggattg ggaagttgat acggagaacg gcaattatga ttacttgatg     600
tacgcagata tcgacatgga tcatccggaa gtggtcaatg agttacgtaa ttggggcgtc     660
tggtacacta cacactgggg ccttgacgga ttccgcattg atgcggttaa acatatcaaa     720
tattcgttta cgcgcgactg gttaactcat gtccggaata caacaggcaa gaatatgttt     780
gctgttgcag aattttggaa aaacgatatc ggcgcgattg aaaattatct ttcaaagact     840
aactggaatc attccgtatt cgacgtgcct ttgcactaca acctgtataa tgcgtcgcgc     900
tccggcggta actatgacat gcgacaaatc ttcaacggca cagtcgttca gcgtcacccc     960
acacacgctg ttacatttgt agacaaccat gacagccaac cggaggaagc tcttgaaagc    1020
ttcgtagaag aatggtttaa gcctctggcc tatgcgctga cgcttacgcg ggatcaagga    1080
tacccgagcg tgttttatgg agattactat ggcattccga cgcatggcgt gccagccatg    1140
aaatcaaaaa ttgatccgat actcgaagcc agacaaaaat atgcatatgg tactcaacgg    1200
gattatttgg accatccgga tgtcattggt tggacccgtg aaggagatgg agtacatgct    1260
aactctggct tagccgcgct gatgtccgat ggtcctggag ctcaaaatg gatggatgtg     1320 ggtaagaaca atgcaggtga agtttggtat gatattaccg gcaatcagac gaatacggtt    1380
actattaata aagatggttg gggacaattt catgtcaacg gcggctctgc gtcaatctat    1440
atccagcag                                                           1449

<210> SEQ ID NO 23
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 23

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30
```

```
Asn Leu Lys Asp Lys Gly Ile Thr Ala Val Trp Ile Pro Pro Ala Trp
    35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
                100                 105                 110

Ala Thr Glu Trp Val Arg Ala Val Glu Val Asn Pro Ser Asn Arg Asn
            115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
            195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
                245                 250                 255

Lys Asn Met Phe Ala Val Ala Glu Phe Trp Lys Asn Asp Ile Gly Ala
                260                 265                 270

Ile Glu Asn Tyr Leu Ser Lys Thr Asn Trp Asn His Ser Val Phe Asp
            275                 280                 285

Val Pro Leu His Tyr Asn Leu Tyr Asn Ala Ser Arg Ser Gly Gly Asn
    290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
                340                 345                 350

Leu Thr Leu Thr Arg Asp Gln Gly Tyr Pro Ser Val Phe Tyr Gly Asp
            355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Thr Gln Arg
385                 390                 395                 400

Asp Tyr Leu Asp His Pro Asp Val Ile Gly Trp Thr Arg Glu Gly Asp
            405                 410                 415

Gly Val His Ala Asn Ser Gly Leu Ala Thr Leu Met Ser Asp Gly Pro
            420                 425                 430

Gly Gly Ser Lys Trp Met Asp Val Gly Lys Asn Asn Ala Gly Glu Val
    435                 440                 445
```

```
Trp Tyr Asp Ile Thr Gly Asn Gln Thr Asn Thr Val Thr Ile Asn Lys
    450                 455                 460

Asp Gly Trp Gly Gln Phe His Val Asn Gly Gly Ser Ala Ser Ile Tyr
465                 470                 475                 480

Ile Gln Gln
```

```
<210> SEQ ID NO 24
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 24
catcacaatg gcacaaacgg taccatgatg caatattttg agtggtacct cccaaatgac      60
ggaaatcatt ggaacagatt gcgctctgat gcaagcaacc ttaaagataa gggcataaca     120
gctgtttgga ttccgccagc atggaaaggc gccagtcaaa cgacgtcgg atatggagcg      180 tacgatctgt atgatttagg cgagtttaat cagaaaggca cagtaagaac gaaatatgga     240
accaggaatc aacttcaggc ggctgtgacg gccctcaagt ctaatggcat tcaggtgtat     300
ggcgacgttg tgatgaacca caaggagga gctgatgcga cagaatgggt tagagcagtc      360
gaagtaaatc ctagcaatcg aaaccaggag gtgagcggtg attacacaat cgaggcatgg     420
accaaattcg actttcctgg acgtggcaac acacatagta attttaagtg gagatggtat     480
cacttcgatg gcgtagactg ggatcaatct agacagttac agaaccggat ctacaaattt     540
cgcggaaaag gctgggattg ggaagttgat acggagaacg gcaattatga ttacttgatg     600
tacgcagata tcgacatgga tcatccggaa gtggtcaatg agttacgtaa ttggggcgtc     660
tggtacacta cacactgggg ccttgacgga ttccgcattg atgcggttaa acatatcaaa     720
tattcgttta cgcgcgactg gttaactcat gtccggaata caacaggcaa gaatatgttt     780
gctgttgcag aattttggaa aaacgatatc ggcgcgattg aaaattatct ttcaaagact     840
aactggaatc attccgtatt cgacgtgcct ttgcactaca acctgtataa tgcgtcgcgc     900
tccggcggta actatgacat gcgacaaatc ttcaacggca cagtcgttca gcgtcacccc     960
acacacgctg ttacatttgt agacaaccat gacagccaac cggaggaagc tcttgaaagc    1020
ttcgtagaag aatggtttaa gcctctggcc tatgcgctga cgcttacgcg ggatcaagga    1080
tacccgagcg tgttttatgg agattactat ggcattccga cgcatggcgt gccagccatg    1140
aaatcaaaaa ttgatccgat actcgaagcc agacaaaaat atgcatatgg tactcaacgg    1200
gattatttgg accatccgga tgtcattggt tggacccgtg aaggagatgg agtacatgct    1260
aactctggct tagccacact gatgtccgat ggtcctggag gctcaaaatg gatggatgtg    1320
ggtaagaaca atgcaggtga gtttggtat gatattaccg gcaatcagac gaatacggtt     1380
actattaata agatggttg gggacaattt catgtcaacg gcggctctgc gtcaatctat    1440
atccagcag                                                           1449
```

```
<210> SEQ ID NO 25
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 25

His His Asn Gly Thr Asn Gly Thr Met Met Gln Tyr Phe Glu Trp Tyr
```

```
1                5                10               15

Leu Pro Asn Asp Gly Asn His Trp Asn Arg Leu Arg Ser Asp Ala Ser
            20               25               30

Asn Leu Lys Asp Lys Gly Ile Thr Ala Val Trp Ile Pro Pro Ala Trp
            35               40               45

Lys Gly Ala Ser Gln Asn Asp Val Gly Tyr Gly Ala Tyr Asp Leu Tyr
        50               55               60

Asp Leu Gly Glu Phe Asn Gln Lys Gly Thr Val Arg Thr Lys Tyr Gly
65               70               75               80

Thr Arg Asn Gln Leu Gln Ala Ala Val Thr Ala Leu Lys Ser Asn Gly
                85               90               95

Ile Gln Val Tyr Gly Asp Val Val Met Asn His Lys Gly Gly Ala Asp
                100              105              110

Ala Thr Glu Trp Val Arg Ala Val Glu Val Asn Pro Ser Asn Arg Asn
            115              120              125

Gln Glu Val Ser Gly Asp Tyr Thr Ile Glu Ala Trp Thr Lys Phe Asp
        130              135              140

Phe Pro Gly Arg Gly Asn Thr His Ser Asn Phe Lys Trp Arg Trp Tyr
145              150              155              160

His Phe Asp Gly Val Asp Trp Asp Gln Ser Arg Gln Leu Gln Asn Arg
                165              170              175

Ile Tyr Lys Phe Arg Gly Lys Gly Trp Asp Trp Glu Val Asp Thr Glu
                180              185              190

Asn Gly Asn Tyr Asp Tyr Leu Met Tyr Ala Asp Ile Asp Met Asp His
            195              200              205

Pro Glu Val Val Asn Glu Leu Arg Asn Trp Gly Val Trp Tyr Thr Asn
    210              215              220

Thr Leu Gly Leu Asp Gly Phe Arg Ile Asp Ala Val Lys His Ile Lys
225              230              235              240

Tyr Ser Phe Thr Arg Asp Trp Leu Thr His Val Arg Asn Thr Thr Gly
                245              250              255

Lys Asn Met Phe Ala Val Ala Glu Phe Trp Lys Asn Asp Ile Gly Ala
            260              265              270

Ile Glu Asn Tyr Leu Ser Lys Thr Asn Trp Asn His Ser Val Phe Asp
            275              280              285

Val Pro Leu His Tyr Asn Leu Tyr Asn Ala Ser Arg Ser Gly Gly Asn
    290              295              300

Tyr Asp Met Arg Gln Ile Phe Asn Gly Thr Val Val Gln Arg His Pro
305              310              315              320

Thr His Ala Val Thr Phe Val Asp Asn His Asp Ser Gln Pro Glu Glu
            325              330              335

Ala Leu Glu Ser Phe Val Glu Glu Trp Phe Lys Pro Leu Ala Tyr Ala
            340              345              350

Leu Thr Leu Thr Arg Asp Gln Gly Tyr Pro Ser Val Phe Tyr Gly Asp
        355              360              365

Tyr Tyr Gly Ile Pro Thr His Gly Val Pro Ala Met Lys Ser Lys Ile
    370              375              380

Asp Pro Ile Leu Glu Ala Arg Gln Lys Tyr Ala Tyr Gly Thr Gln Arg
385              390              395              400

Asp Tyr Leu Asp His Pro Asp Val Ile Gly Trp Thr Arg Glu Gly Asp
            405              410              415

Gly Val His Val Asn Ser Gly Leu Ala Thr Leu Met Ser Asp Gly Pro
        420              425              430
```

```
Gly Gly Ser Lys Trp Met Asp Val Gly Lys Asn Asn Ala Gly Glu Val
        435                 440                 445

Trp His Asp Ile Thr Gly Asn Gln Thr Asn Thr Val Thr Ile Asn Arg
    450                 455                 460

Asp Gly Trp Gly Gln Phe His Val Ser Gly Gly Ser Val Ser Ile Tyr
465                 470                 475                 480

Val Gln Gln
```

<210> SEQ ID NO 26
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 26

```
catcacaatg gcacaaacgg taccatgatg caatattttg agtggtacct cccaaatgac     60
ggaaatcatt ggaacagatt gcgctctgat gcaagcaacc ttaaagataa gggcataaca    120
gctgtttgga ttccgccagc atggaaaggc gccagtcaaa cgacgtcgg atatggagcg     180 tacgatctgt atgatttagg cgagtttaat cagaaaggca cagtaagaac gaaatatgga    240
accaggaatc aacttcaggc ggctgtgacg gccctcaagt ctaatggcat tcaggtgtat    300
ggcgacgttg tgatgaacca caaaggagga gctgatgcga cagaatgggt tagagcagtc    360
gaagtaaatc ctagcaatcg aaaccaggag gtgagcggtg attacacaat cgaggcatgg    420
accaaattcg actttcctgg acgtggcaac acacatagta attttaagtg gagatggtat    480
cacttcgatg gcgtagactg ggatcaatct agacagttac agaaccggat ctacaaattt    540
cgcggaaaag gctgggattg ggaagttgat acggagaacg gcaattatga ttacttgatg    600
tacgcagata tcgacatgga tcatccggaa gtggtcaatg agttacgtaa ttggggcgtc    660
tggtacacta acacactggg ccttgacgga ttccgcattg atgcggttaa acatatcaaa    720
tattcgttta cgcgcgactg gttaactcat gtccggaata caacaggcaa gaatatgttt    780
gctgttgcag aattttggaa aaacgatatc ggcgcgattg aaaattatct ttcaaagact    840
aactggaatc attccgtatt cgacgtgcct ttgcactaca acctgtataa tgcgtcgcgc    900
tccggcggta actatgacat gcgacaaatc ttcaacggca cagtcgttca gcgtcaccc     960 acacacgctg ttacatttgt agacaaccat gacagccaac cggaggaagc tcttgaaagc   1020
ttcgtagaag aatggtttaa gcctctggcc tatgcgctga cgcttacgcg ggatcaagga   1080
tacccgagcg tgttttatgg agattactat ggcattccga cgcatggcgt gccagccatg   1140
aaatcaaaaa ttgatccgat actcgaagcc agacaaaaat atgcatatgg tactcaacgg   1200
gattatttgg accatccgga tgtcattggt tggacccgtg aaggagatgg agtacatgtc   1260
aactctggct tagccacact gatgtccgat ggtcctggag ctcaaaatg gatggatgtg    1320 ggtaagaaca atgcaggtga agtttggcat gatattaccg gcaatcagac gaatacggtt   1380
actattaatc gcgatggttg gggacaattt catgtctcag gcggctctgt ctcaatctat   1440
gttcagcag                                                          1449
```

<210> SEQ ID NO 27
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 27

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
                100                 105                 110

Ala Thr Glu Trp Val Arg Ala Val Glu Val Asn Pro Ser Asn Arg Asn
            115                 120                 125

Gln Glu Val Ser Gly Asp Tyr Thr Ile Glu Ala Trp Thr Lys Phe Asp
        130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
            195                 200                 205

Pro Glu Val Val Asn Glu Leu Arg Asn Trp Gly Val Trp Tyr Thr Asn
        210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
                245                 250                 255

Lys Asn Met Phe Ala Val Ala Glu Phe Trp Lys Asn Asp Ile Gly Ala
            260                 265                 270

Ile Glu Asn Tyr Leu Ser Lys Thr Asn Trp Asn His Ser Val Phe Asp
            275                 280                 285

Val Pro Leu His Tyr Asn Leu Tyr Asn Ala Ser Arg Ser Gly Gly Asn
        290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Asp Gln Gly Tyr Pro Ser Val Phe Tyr Gly Asp
            355                 360                 365

Tyr Tyr Gly Ile Pro Thr His Gly Val Pro Ala Met Lys Ser Lys Ile
        370                 375                 380

Asp Pro Ile Leu Glu Ala Arg Gln Lys Tyr Ala Tyr Gly Thr Gln Arg
385                 390                 395                 400

Asp Tyr Leu Asp His Pro Asp Val Ile Gly Trp Thr Arg Glu Gly Asp

-continued

```
                   405              410              415
Ser Val His Ala Asn Ser Gly Leu Ala Thr Leu Met Ser Asp Gly Pro
            420              425              430

Gly Gly Ala Lys Trp Met Asp Val Gly Lys Asn Asn Ala Gly Glu Val
         435              440              445

Trp Tyr Asp Ile Thr Gly Asn Gln Thr Asn Thr Val Thr Ile Asn Lys
      450              455              460

Asp Gly Trp Gly Gln Phe Gln Val Ser Gly Gly Ser Val Ser Ile Tyr
465              470              475              480

Val Gln Gln
```

```
<210> SEQ ID NO 28
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 28
catcacaatg gcacaaacgg taccatgatg caatattttg agtggtacct cccaaatgac      60
ggaaatcatt ggaacagatt gcgctctgat gcaagcaacc ttaaagataa gggcataaca     120
gctgtttgga ttccgccagc atggaaaggc gccagtcaaa cgacgtcgg atatggagcg      180 tacgatctgt atgatttagg cgagtttaat cagaaaggca cagtaagaac gaaatatgga     240
accaggaatc aacttcaggc ggctgtgacg gccctcaagt ctaatggcat tcaggtgtat     300
ggcgacgttg tgatgaacca caaaggagga gctgatgcga cagaatgggt tagagcagtc     360
gaagtaaatc ctagcaatcg aaaccaggag gtgagcggtg attacacaat cgaggcatgg     420
accaaattcg actttcctgg acgtggcaac acacatagta atttttaagtg gagatggtat     480 cacttcgatg gcgtagactg ggatcaatct agacagttac agaaccggat ctacaaattt     540
cgcggaaaag gctgggattg ggaagttgat acggagaacg gcaattatga ttacttgatg     600
tacgcagata tcgacatgga tcatccggaa gtggtcaatg agttacgtaa ttggggcgtc     660
tggtacacta cacactgggg ccttgacgga ttccgcattg atgcggttaa acatatcaaa     720
tattcgttta cgcgcgactg gttaactcat gtccggaata caacaggcaa gaatatgttt     780
gctgttgcag aatttttggaa aaacgatatc ggcgcgattg aaaattatct ttcaaagact     840
aactggaatc attccgtatt cgacgtgcct ttgcactaca acctgtataa tgcgtcgcgc     900
tccggcggta actatgacat cgacaaaatc ttcaacggca cagtcgttca gcgtcacccc     960
acacacgctg ttacatttgt agacaaccat gacagccaac cggaggaagc tcttgaaagc    1020
ttcgtagaag aatggtttaa gcctctggcc tatgcgctga cgcttacgcg ggatcaagga    1080
tacccgagcg tgtttttatgg agattactat ggcattccga cgcatggcgt gccagccatg    1140
aaatcaaaaa ttgatccgat actcgaagcc agacaaaaat atgcatatgg tactcaacgg    1200
gattatttgg accatccgga tgtcattggt tggacccgtg aaggagatag cgtacatgct    1260
aactctggct tagccacact gatgtccgat ggtcctggag gcgcgaaatg gatggatgtg    1320
ggtaagaaca atgcaggtga agtttggtat gatattaccg gcaatcagac gaatacggtt    1380
actattaata aagatggttg gggacaattt caggtctcag gcggctctgt ctcaatctat    1440
gttcagcag                                                            1449
```

```
<210> SEQ ID NO 29
<211> LENGTH: 483
```

<212> TYPE: PRT
<213> ORGANISM: Artificial Sequence
<220> FEATURE:
<223> OTHER INFORMATION: recombinant amylase variant

<400> SEQUENCE: 29

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
            115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
            195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
            245                 250                 255

Lys Asn Met Phe Ala Val Ala Glu Phe Trp Lys Asn Asp Ile Gly Ala
            260                 265                 270

Ile Glu Asn Tyr Leu Ser Lys Thr Asn Trp Asn His Ser Val Phe Asp
            275                 280                 285

Val Pro Leu His Tyr Asn Leu Tyr Asn Ala Ser Arg Ser Gly Gly Asn
    290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
            325                 330                 335

Ala Leu Glu Ser Phe Val Glu Glu Trp Phe Lys Pro Leu Ala Tyr Ala
            340                 345                 350

Leu Thr Leu Thr Arg Asp Gln Gly Tyr Pro Ser Val Phe Tyr Gly Asp
        355                 360                 365

Tyr Tyr Gly Ile Pro Thr His Gly Val Pro Ala Met Lys Ser Lys Ile
    370                 375                 380

```
Asp Pro Ile Leu Glu Ala Arg Gln Lys Tyr Ala Tyr Gly Thr Gln His
385             390             395             400

Asp Tyr Leu Asp His Pro Asp Val Ile Gly Trp Thr Arg Glu Gly Asp
            405             410             415

Ser Ile His Ala Asn Ser Gly Leu Ala Thr Leu Met Ser Asp Gly Pro
            420             425             430

Gly Gly Ser Lys Trp Met Asn Val Gly Lys Asn Asn Ala Gly Glu Ile
        435             440             445

Trp Tyr Asp Ile Thr Gly Asn Gln Thr Asn Thr Val Thr Ile Asn Lys
    450             455             460

Asp Gly Trp Gly Gln Phe His Val Asn Gly Gly Ser Val Ser Ile Tyr
465             470             475             480

Val Gln Lys
```

```
<210> SEQ ID NO 30
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 30
catcacaatg gcacaaacgg taccatgatg caatattttg agtggtacct cccaaatgac      60
ggaaatcatt ggaacagatt gcgctctgat gcaagcaacc ttaaagataa gggcataaca     120
gctgtttgga ttccgccagc atggaaaggc gccagtcaaa acgacgtcgg atatggagcg     180
tacgatctgt atgatttagg cgagtttaat cagaaaggca cagtaagaac gaaatatgga     240
accaggaatc aacttcaggc ggctgtgacg gccctcaagt ctaatggcat tcaggtgtat     300
ggcgacgttg tgatgaacca caaaggagga gctgatgcga cagaatgggt tagagcagtc     360
gaagtaaatc ctagcaatcg aaaccaggag gtgagcggtg attacacaat cgaggcatgg     420
accaaattcg actttcctgg acgtggcaac acacatagta attttaagtg gagatggtat     480
cacttcgatg gcgtagactg ggatcaatct agacagttac agaaccggat ctacaaattt     540
cgcggaaaag gctgggattg ggaagttgat acggagaacg gcaattatga ttacttgatg     600
tacgcagata tcgacatgga tcatccggaa gtggtcaatg agttacgtaa ttggggcgtc     660
tggtacacta acacactggg ccttgacgga ttccgcattg atgcggttaa acatatcaaa     720 tattcgtttta cgcgcgactg gttaactcat gtccggaata caacaggcaa gaatatgttt     780
gctgttgcag aattttggaa aaacgatatc ggcgcgattg aaaattatct ttcaaagact     840
aactggaatc attccgtatt cgacgtgcct ttgcactaca acctgtataa tgcgtcgcgc     900
tccggcggta actatgacat gcgacaaatc ttcaacggca cagtcgttca gcgtcacccc     960
acacacgctg ttacatttgt agacaaccat gacagccaac cggaggaagc tcttgaaagc    1020
ttcgtagaag aatggtttaa gcctctggcc tatgcgctga cgcttacgcg ggatcaagga    1080
tacccgagcg tgttttatgg agattactat ggcattccga cgcatggcgt gccagccatg    1140
aaatcaaaaa ttgatccgat actcgaagcc agacaaaaat atgcatatgg tactcaacat    1200
gattatttgg accatccgga tgtcattggt tggacccgtg aaggagatag catccatgct    1260
aactctggct tagccacact gatgtccgat ggtcctggag gctcaaaatg gatgaacgtg    1320
ggtaagaaca atgcaggtga aatctggtat gatattaccg gcaatcagac gaatacggtt    1380
actattaata aagatggttg gggacaattt catgtcaacg gcggctctgt ctcaatctat    1440
gttcagaaa                                                           1449
```

```
<210> SEQ ID NO 31
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 31

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
            115                 120                 125

Gln Glu Val Ser Gly Asp Tyr Thr Ile Glu Ala Trp Thr Lys Phe Asp
        130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
            195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
                245                 250                 255

Lys Asn Met Phe Ala Val Ala Glu Phe Trp Lys Asn Asp Ile Gly Ala
            260                 265                 270

Ile Glu Asn Tyr Leu Ser Lys Thr Asn Trp Asn His Ser Val Phe Asp
            275                 280                 285

Val Pro Leu His Tyr Asn Leu Tyr Asn Ala Ser Arg Ser Gly Gly Asn
    290                 295                 300

Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Asp Gln Gly Tyr Pro Ser Val Phe Tyr Gly Asp
            355                 360                 365
```

```
Tyr Tyr Gly Ile Pro Thr His Gly Val Pro Ala Met Lys Ser Lys Ile
    370               375               380

Asp Pro Ile Leu Glu Ala Arg Gln Lys Tyr Ala Tyr Gly Thr Gln Arg
385               390               395               400

Asp Tyr Leu Asp His Pro Asp Val Ile Gly Trp Thr Arg Glu Gly Asp
            405               410               415

Gly Val His Ala Asn Ser Gly Leu Ala Thr Leu Met Ser Asp Gly Pro
            420               425               430

Gly Gly Ser Lys Trp Met Asp Val Gly Lys Asn Asn Ala Gly Glu Val
            435               440               445

Trp Tyr Asp Ile Thr Gly Asn Gln Thr Asn Thr Val Thr Ile Asn Lys
    450               455               460

Asp Gly Trp Gly Gln Phe His Val Asn Gly Gly Ser Val Ser Ile Tyr
465               470               475               480

Ile Gln Gln
```

<210> SEQ ID NO 32
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 32

```
catcacaatg gcacaaacgg taccatgatg caatattttg agtggtacct cccaaatgac      60
ggaaatcatt ggaacagatt gcgctctgat gcaagcaacc ttaaagataa gggcataaca     120
gctgtttgga ttccgccagc atggaaaggc gccagtcaaa cgacgtcgg atatggagcg      180 tacgatctgt atgatttagg cgagtttaat cagaaaggca cagtaagaac gaaatatgga     240
accaggaatc aacttcaggc ggctgtgacg gccctcaagt ctaatggcat tcaggtgtat     300
ggcgacgttg tgatgaacca caaaggagga gctgatgcga cagaatgggt tagagcagtc     360
gaagtaaatc ctagcaatcg aaaccaggag gtgagcggtg attacacaat cgaggcatgg     420
accaaattcg actttcctgg acgtggcaac acacatagta attttaagtg gagatggtat     480
cacttcgatg gcgtagactg ggatcaatct agacagttac agaaccggat ctacaaattt     540
cgcggaaaag gctgggattg ggaagttgat acggagaacg gcaattatga ttacttgatg     600
tacgcagata tcgacatgga tcatccggaa gtggtcaatg agttacgtaa ttggggcgtc     660
tggtacacta acactgggc ccttgacgga ttccgcattg atgcggttaa acatatcaaa       720
tattcgttta cgcgcgactg gttaactcat gtccggaata caacaggcaa gaatatgttt     780
gctgttgcag aattttggaa aaacgatatc ggcgcgattg aaaattatct ttcaaagact     840
aactggaatc attccgtatt cgacgtgcct ttgcactaca acctgtataa tgcgtcgcgc     900
tccggcggta actatgacat gcgacaaatc ttcaacggca cagtcgttca gcgtcacccc     960
acacacgctg ttacatttgt agacaaccat gacagccaac cggaggaagc tcttgaaagc    1020
ttcgtagaag aatggtttaa gcctctggcc tatgcgctga cgcttacgcg ggatcaagga    1080
tacccgagcg tgttttatgg agattactat ggcattccga cgcatggcgt gccagccatg    1140
aaatcaaaaa ttgatccgat actcgaagcc agacaaaaat atgcatatgg tactcaacgg    1200
gattatttgg accatccgga tgtcattggt tggacccgtg aaggagatgg agtacatgct    1260
aactctggct tagccacact gatgtccgat ggtcctggag ctcaaaatg gatggatgtg     1320 ggtaagaaca atgcaggtga agtttggtat gatattaccg gcaatcagac gaatacggtt    1380
```

-continued

```
actattaata aagatggttg gggacaattt catgtcaacg gcggctctgt ctcaatctat    1440
atccagcag                                                           1449
```

<210> SEQ ID NO 33
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 33

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
            115                 120                 125

Gln Glu Val Thr Gly Glu Tyr Thr Ile Glu Ala Trp Thr Arg Phe Asp
        130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly Lys Ala Trp Asp Trp Glu Val Asp Thr Glu
                180                 185                 190

Asn Gly Asn Tyr Asp Tyr Leu Met Tyr Ala Asp Ile Asp Met Asp His
                195                 200                 205

Pro Glu Val Val Asn Glu Leu Arg Asn Trp Gly Val Trp Tyr Thr Asn
        210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
                260                 265                 270

Ile Glu Asn Tyr Leu Gln Lys Thr Asn Trp Asn His Ser Val Phe Asp
                275                 280                 285

Val Pro Leu His Tyr Asn Leu Tyr Asn Ala Ser Lys Ser Gly Gly Asn
        290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
```

-continued

```
                340             345             350
Leu Thr Leu Thr Arg Glu Gln Gly Tyr Pro Ser Val Phe Tyr Gly Asp
        355             360             365
Tyr Tyr Gly Ile Pro Thr His Gly Val Pro Ala Met Arg Ser Lys Ile
    370             375             380
Asp Pro Ile Leu Glu Ala Arg Gln Lys Tyr Ala Tyr Gly Thr Gln Arg
385             390             395             400
Asp Tyr Leu Asp His Pro Asp Val Ile Gly Trp Thr Arg Glu Gly Asp
            405             410             415
Gly Val His Ala Asp Ser Gly Leu Ala Thr Leu Met Ser Asp Gly Pro
            420             425             430
Gly Gly Ser Lys Trp Met Glu Val Gly Lys Asn Asn Ala Gly Glu Val
        435             440             445
Trp Tyr Asp Ile Thr Gly Asn Gln Thr Asn Thr Val Thr Ile Asn Lys
    450             455             460
Asp Gly Trp Gly Gln Phe His Val Ser Gly Gly Ser Val Ser Ile Tyr
465             470             475             480
Val Gln Gln
```

<210> SEQ ID NO 34
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 34

```
caccataacg gcacgaatgg aacgatgatg caatattttg agtggtactt acctaatgac    60
ggcaaccatt ggaaccggtt gaactcggac gcatcaaatc ttaaaagcaa gggtattacg   120
gcggtttgga ttccgcctgc gtggaaaggg gcgagccaga atgatgtagg ctacggcgca   180
tatgatctgt atgatcttgg ggaattcaac caaaaaggaa ctgttcgaac gaaatacggt   240
acacggtcgc agttgcaggc ggccgtcacc agtctgaaga ataacggaat ccaggtatat   300
ggagatgtgg ttatgaatca caaagggggga gcagacgcaa ccgaaatggt cagggccgtt   360
gaagtcaatc caaacaatcg caaccaggaa gtcacaggcg aatatactat tgaggcctgg   420
acgcgcttcg attttcccgg aagaggcaat acacatagct cgtttaaatg gcgttggtat   480
cattttgacg gcgtggattg ggatcaatcc agaaggctca ataaccgcat ctacaaattt   540
cggggcaagg cctgggattg ggaagtggat acagagaacg gtaactatga ctatttaatg   600
tatgcggata tagacatgga tcaccccgaa gtcgtgaacg aacttaggaa ttggggtgtc   660
tggtacacga acacattagg cctgatggga tttcgcatcg atgcagttaa acacataaaa   720
tactctttca cccgggactg gatcaatcat gtaagaagcg cgaccggaaa aaacatgttt   780
gctgtagccg agttttggaa aaacgaccta ggagccatcg aaaattacct ccaaaaaaca   840
aactggaacc actcagtctt cgatgtcccg cttcattaca acttgtataa tgctagcaag   900
tcaggaggca attatgatat gcgcaatatt tttaacggca cggttgtgca acgtcacccg   960
tctcatgcgg tgacgttcgt ggacaaccac gactcccagc cggaagaggc gctcgaatct  1020
ttcgttgaag agtggtttaa accgttggcg tatgccctga ctcttacgcg tgaacaaggg  1080
tatccgtcag ttttttatgg agactactat ggcatcccta cacatggcgt ccctgctatg  1140
agatccaaga ttgatccaat cctggaagcc cgccaaaaat acgcatatgg tacccagaga  1200
gattacctcg accatcctga cgtcattggc tggacacgag aagggggacgg agttcatgct  1260
```

-continued

```
gattctgggc ttgcaacact gatgtcagac ggaccgggag ggtcgaaatg gatggaggtc      1320
ggcaagaata acgctggcga ggtgtggtat gatatcaccg gtaatcagac aaacacggtg      1380
acgattaata aggatggctg ggggcagttt catgtaagcg gtggatccgt cagcatctat      1440
gtccagcaa                                                              1449

<210> SEQ ID NO 35
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 35

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Gln Ile Phe Asn Gly Thr Val Val Gln Arg His Pro
305                 310                 315                 320
```

-continued

```
Met His Ala Val Thr Phe Val Asp Asn His Asp Ser Gln Pro Glu Glu
             325                 330                 335

Ala Leu Glu Ser Phe Val Glu Glu Trp Phe Lys Pro Leu Ala Tyr Ala
             340                 345                 350

Leu Thr Leu Thr Arg Glu Gln Gly Tyr Pro Ser Val Phe Tyr Gly Asp
             355                 360                 365

Tyr Tyr Gly Ile Pro Thr His Gly Val Pro Ala Met Lys Ser Lys Ile
     370                 375                 380

Asp Pro Ile Leu Glu Ala Arg Gln Lys Tyr Ala Tyr Gly Thr Gln Arg
385                 390                 395                 400

Asp Tyr Leu Asp His Pro Asp Val Ile Gly Trp Thr Arg Glu Gly Asp
             405                 410                 415

Gly Val His Ala Asp Ser Gly Leu Ala Thr Leu Met Ser Asp Gly Pro
             420                 425                 430

Gly Gly Ser Lys Trp Met Glu Val Gly Lys Asn Asn Ala Gly Glu Val
             435                 440                 445

Trp Tyr Asp Ile Thr Gly Asn Gln Thr Asn Thr Val Thr Ile Asn Lys
     450                 455                 460

Asp Gly Trp Gly Gln Phe His Val Ser Gly Gly Ser Val Ser Ile Tyr
465                 470                 475                 480

Val Gln Gln
```

<210> SEQ ID NO 36
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 36

```
caccataacg gcacgaatgg aacgatgatg caatattttg agtggtactt acctaatgac      60
ggcaaccatt ggaaccggtt gcgctcggac gcatcaaatc ttaaagataa gggtattagc     120
gcggtttgga ttccgcctgc gtggaaaggg gcgagccaga atgatgtagg ctacggcgca     180
tatgatctgt atgatcttgg ggaattcaac caaaaaggaa ctatccgaac gaaatacggt     240
acacggaacc agttgcaggc ggccgtcaac gccctgaaga gcaacggaat ccaggtatat     300
ggagatgtgg ttatgaatca caaaggggga gcagacgcaa ccgaaatggt cagggccgtt     360
gaagtcaatc caaacaatcg caaccaggaa gtcagcggcg aatatactat tgaggcctgg     420
acgaaattcg attttcccgg aagaggcaat acacatagca actttaaatg gcgttggtat     480
cattttgacg gcgtggattg ggatcaatcc agaaaactca ataaccgcat ctacaaattt     540
cggggcaagg gctgggattg ggaagtggat acagagaacg gtaactatga ctatttaatg     600
tatgcggata tagacatgga tcaccccgaa gtcgtgaacg aacttaggaa ttggggtgtc     660
tggtacacga acacattagg cctggatgga tttcgcatcg atgcagttaa acacataaaa     720
tactctttca cccgggactg gatcaatcat gtaagaagcg cgaccggaaa aaacatgttt     780
gctgtagccg agttttggaa aaacgaccta ggagccatcg aaaattacct caacaaaaca     840
aactggaacc actcagtctt cgatgtcccg cttcattaca acttgtataa tgctagcaag     900
tcaggaggca attatgatat cgccagatt tttaacggca cggttgtgca acgtcacccg     960
atgcatgcgg tgacgttcgt ggacaaccac gactcccagc cggaagaggc gctcgaatct    1020
ttcgttgaag agtggtttaa accgttggcg tatgccctga ctcttacgcg tgaacaaggg    1080
tatccgtcag tttttatgg agactactat ggcatcccta cacatggcgt ccctgctatg    1140
```

-continued

```
aaatccaaga ttgatccaat cctggaagcc cgccaaaaat acgcatatgg tacccagaga    1200
gattacctcg accatcctga cgtcattggc tggacacgag aaggggacgg agttcatgct    1260
gattctgggc ttgcaacact gatgtcagac ggaccgggag ggtcgaaatg gatggaggtc    1320
ggcaagaata acgctggcga ggtgtggtat gatatcaccg gtaatcagac aaacacggtg    1380
acgattaata aggatggctg ggggcagttt catgtaagcg gtggatccgt cagcatctat    1440
gtccagcaa                                                             1449
```

```
<210> SEQ ID NO 37
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 37

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
                245                 250                 255

Lys Asn Met Phe Ala Val Ala Glu Phe Trp Lys Asn Asp Ile Gly Ala
            260                 265                 270

Ile Glu Asn Tyr Leu Ser Lys Thr Asn Trp Asn His Ser Val Phe Asp
        275                 280                 285

Val Pro Leu His Tyr Asn Leu Tyr Asn Ala Ser Arg Ser Gly Gly Asn
    290                 295                 300
```

```
Tyr Asp Met Arg Gln Ile Phe Asn Gly Thr Val Val Gln Arg His Pro
305                 310                 315                 320

Thr His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
                340                 345                 350

Leu Thr Leu Thr Arg Asp Gln Gly Tyr Pro Ser Val Phe Tyr Gly Asp
                355                 360                 365

Tyr Tyr Gly Ile Pro Thr His Gly Val Pro Ala Met Lys Ser Lys Ile
        370                 375                 380

Asp Pro Ile Leu Glu Ala Arg Gln Lys Tyr Ala Tyr Gly Thr Gln Arg
385                 390                 395                 400

Asp Tyr Leu Asp His Pro Asp Val Ile Gly Trp Thr Arg Glu Gly Asp
                405                 410                 415

Ser Val His Ala Asn Ser Gly Leu Ala Thr Leu Met Ser Asp Gly Pro
                420                 425                 430

Gly Gly Ser Lys Trp Met Asp Val Gly Lys Asn Asn Ala Gly Glu Val
                435                 440                 445

Trp Arg Asp Ile Thr Gly Asn Gln Thr Asn Thr Val Thr Ile Asn Lys
        450                 455                 460

Asp Gly Trp Gly Gln Phe His Val Ser Gly Gly Ser Val Ser Ile Tyr
465                 470                 475                 480

Val Gln Gln
```

<210> SEQ ID NO 38
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 38

```
catcacaacg ggacgaatgg aacgatgatg cagtattttg agtggtattt gcctaacgac      60
ggtaatcact ggaaccgatt gcggtcggat gctagcaacc tcaaagataa aggtattaca     120
gccgtgtgga taccgcctgc gtggaaagga gcgtctcaga acgacgtggg ttatggagcg     180
tatgatttat atgacttagg ggaattcaac cagaaaggca cagttcgcac caagtacggc     240
actaggaatc aactccaggc tgcggtgact gcgctgaaat caaatggaat ccaagtgtat     300
ggcgatgtcg taatgaacca taaggaggc gcagatgcca cagaatgggt gagggccgtc     360
gaggttaatc catccaaccg caatcaggaa gtaagcgggg actacactat agaggcatgg     420
acaaaatttg attttccagg acgtggaaac acgcatagca atttcaaatg gagatggtat     480
cacttcgatg gtgtggactg ggaccaatct agacaactgc aaaaccgcat ctacaaattt     540
aggggaaaag gctgggattg ggaggtggac acagaaaatg gaactacgga ctatcttatg     600
tatgcggaca tcgatatgga ccatcctgaa gtggttaatg aactccgcaa ttggggcgtc     660
tggtacacga acacactggg cctggatggg tttcgcatcg acgcggttaa acacattaaa     720
tattcattca cgagagactg gttgacgcat gtccgtaaca ccacagggaa gaacatgttt     780
gcagtcgcgg aattttggaa aaacgatatt ggagcaatcg aaaactatct ttcaaagacg     840
aattggaatc attctgtatt cgatgttccg ctacattata atctgtataa tgctagccgt     900
agcggtggaa actatgatat gcggcaaatt tttaatggaa cggttgtcca aagacatccg     960
acacacgccg tcacatttgt tgataatcac gattcgcaac cggaagaggc actcgaatcg    1020
```

-continued

```
tttgtcgaag agtggtttaa gcctcttgct tatgcgctta cacttacgcg ggatcagggc    1080
tatccctccg ttttctatgg cgattactat ggaattccga cgcacggggt gccggccatg    1140
aaatcgaaga tcgaccccat cctggaagct cgccagaagt acgcctacgg cacgcagcga    1200
gattacttag accatccgga tgtaattggc tggaccagag aaggcgatag cgttcatgcc    1260
aattcaggac ttgcaacctt gatgagtgac ggccctggag ctccaagtg atggatgtc    1320 ggcaaaaaca atgccggcga agtctggcgg gacatcacgg gtaatcagac caacaccgtc    1380
acaattaata aagatggatg gggccaattt catgtatccg ggggttcagt ctctatctac    1440
gtccagcaa                                                            1449
```

<210> SEQ ID NO 39
<211> LENGTH: 485
<212> TYPE: PRT
<213> ORGANISM: Artificial Sequence
<220> FEATURE:
<223> OTHER INFORMATION: recombinant amylase variant

<400> SEQUENCE: 39

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
```

-continued

```
                275                 280                 285

Phe Asp Val Pro Leu His Tyr Asn Leu Tyr Asn Ala Ser Arg Ser Gly
    290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Asp Gln Gly Tyr Pro Ser Val Phe Tyr
                355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
                420                 425                 430

Gly Pro Gly Gly Asn Lys Trp Met Tyr Val Gly Arg Asn Lys Ala Gly
                435                 440                 445

Gln Val Trp Arg Asp Ile Thr Gly Asn Arg Ser Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Asn
                485
```

<210> SEQ ID NO 40
<211> LENGTH: 486
<212> TYPE: PRT
<213> ORGANISM: Artificial Sequence
<220> FEATURE:
<223> OTHER INFORMATION: recombinant amylase variant

<400> SEQUENCE: 40

```
Ala Thr Ile Asn Asn Gly Thr Leu Met Gln Tyr Phe Glu Trp Tyr Ala
1               5                   10                  15

Pro Asn Asp Gly Asn His Trp Lys Arg Leu His Thr Asp Ala Gly Asn
                20                  25                  30

Leu Ala Gln Lys Gly Ile Thr Ser Val Trp Ile Pro Pro Ala Tyr Lys
            35                  40                  45

Gly Thr Thr Gln Asn Asp Val Gly Tyr Gly Ala Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Leu Lys Ser Ala Ile Glu Ala Leu His Lys Gln Asn Ile
                85                  90                  95

Asn Val Tyr Gly Asp Val Val Met Asn His Lys Gly Gly Ala Asp Tyr
                100                 105                 110

Thr Glu Thr Val Thr Ala Val Glu Val Asp Arg Asn Asn Arg Asn Ile
            115                 120                 125

Glu Val Ser Gly Asp Tyr Glu Ile Asn Ala Trp Thr Gly Phe Asn Phe
    130                 135                 140

Pro Gly Arg Gly Asp Thr His Ser Asn Phe Lys Trp Lys Trp Tyr His
```

```
145                 150                 155                 160

Phe Asp Gly Thr Asp Trp Asp Glu Gly Arg Lys Leu Asn Arg Ile Tyr
                165                 170                 175

Lys Phe Arg Gly Ile Gly Lys Ala Trp Asp Trp Glu Val Ser Ser Glu
                180                 185                 190

Asn Gly Asn Tyr Asp Tyr Leu Met Tyr Ala Asp Leu Asp Phe Asp His
                195                 200                 205

Pro Asp Val Ala Asn Glu Met Lys Asn Trp Gly Thr Trp Tyr Ala Asn
    210                 215                 220

Glu Leu Asn Leu Asp Gly Phe Arg Leu Asp Ala Val Lys His Ile Asp
225                 230                 235                 240

His Glu Tyr Leu Arg Asp Trp Val Asn His Val Arg Gln Gln Thr Gly
                245                 250                 255

Lys Glu Met Phe Thr Val Ala Glu Tyr Trp Gln Asn Asp Ile Gln Thr
                260                 265                 270

Leu Asn Asn Tyr Leu Ala Lys Val Asn Tyr Asn Gln Ser Val Phe Asp
                275                 280                 285

Ala Pro Leu His Tyr Asn Phe His Tyr Ala Ser Lys Gly Asn Gly Asn
    290                 295                 300

Tyr Asp Met Arg Asn Ile Leu Asn Gly Thr Val Met Gln Asn His Pro
305                 310                 315                 320

Ala Leu Ala Val Thr Leu Val Glu Asn His Asp Ser Gln Pro Gly Gln
                325                 330                 335

Ser Leu Glu Ser Val Val Ser Pro Trp Phe Lys Pro Leu Ala Tyr Ala
                340                 345                 350

Phe Ile Leu Thr Arg Ala Glu Gly Tyr Pro Ser Val Phe Tyr Gly Asp
                355                 360                 365

Tyr Tyr Gly Thr Ser Gly Asn Ser Ser Tyr Glu Ile Pro Ala Leu Lys
    370                 375                 380

Asp Lys Ile Asp Pro Ile Leu Met Ala Arg Lys Asn Phe Ala Tyr Gly
385                 390                 395                 400

Thr Gln Arg Asp Tyr Leu Asp His Pro Asp Val Ile Gly Trp Thr Arg
                405                 410                 415

Glu Gly Asp Gly Val His Ala Asp Ser Gly Leu Ala Thr Leu Ile Ser
                420                 425                 430

Asp Gly Pro Gly Gly Ser Lys Trp Met Glu Val Gly Lys Asn Asn Ala
                435                 440                 445

Gly Glu Val Trp Tyr Asp Met Thr Gly Asn Gln Thr Asn Thr Val Thr
    450                 455                 460

Ile Asn Lys Asp Gly Trp Gly Gln Phe His Val Ser Gly Gly Ser Val
465                 470                 475                 480

Ser Ile Tyr Val Gln Gln
                485
```

<210> SEQ ID NO 41
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 41

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
```

```
                20              25              30

Asn Leu Lys Asp Lys Gly Ile Thr Ala Val Trp Ile Pro Pro Ala Trp
        35              40              45

Lys Gly Ala Ser Gln Asn Asp Val Gly Tyr Gly Ala Tyr Asp Leu Tyr
        50              55              60

Asp Leu Gly Glu Phe Asn Gln Lys Gly Thr Val Arg Thr Lys Tyr Gly
65              70              75              80

Thr Arg Asn Gln Leu Gln Ala Ala Val Thr Ala Leu Lys Ser Asn Gly
                85              90              95

Ile Gln Val Tyr Gly Asp Val Val Met Asn His Lys Gly Gly Ala Asp
                100             105             110

Ala Thr Glu Trp Val Arg Ala Val Glu Val Asn Pro Ser Asn Arg Asn
        115             120             125

Gln Glu Val Ser Gly Asp Tyr Thr Ile Glu Ala Trp Thr Lys Phe Asp
        130             135             140

Phe Pro Gly Arg Gly Asn Thr His Ser Asn Phe Lys Trp Arg Trp Tyr
145             150             155             160

His Phe Asp Gly Val Asp Trp Asp Gln Ser Arg Gln Leu Gln Asn Arg
                165             170             175

Ile Tyr Lys Phe Arg Gly Lys Gly Trp Asp Trp Glu Val Asp Thr Glu
                180             185             190

Asn Gly Asn Tyr Asp Tyr Leu Met Tyr Ala Asp Ile Asp Met Asp His
                195             200             205

Pro Glu Val Val Asn Glu Leu Arg Asn Trp Gly Val Trp Tyr Thr Asn
        210             215             220

Thr Leu Gly Leu Asp Gly Phe Arg Ile Asp Ala Val Lys His Ile Lys
225             230             235             240

Tyr Ser Phe Thr Arg Asp Trp Leu Thr His Val Arg Asn Thr Thr Gly
                245             250             255

Lys Asn Met Phe Ala Val Ala Glu Phe Trp Lys Asn Asp Ile Gly Ala
                260             265             270

Ile Glu Asn Tyr Leu Ser Lys Thr Asn Trp Asn His Ser Val Phe Asp
        275             280             285

Val Pro Leu His Tyr Asn Leu Tyr Asn Ala Ser Arg Ser Gly Gly Asn
        290             295             300

Tyr Asp Met Arg Gln Ile Phe Asn Gly Thr Val Val Gln Arg His Pro
305             310             315             320

Thr His Ala Val Thr Phe Val Asp Asn His Asp Ser Gln Pro Glu Glu
                325             330             335

Ala Leu Glu Ser Phe Val Glu Glu Trp Phe Lys Pro Leu Ala Tyr Ala
                340             345             350

Leu Thr Leu Thr Arg Asp Gln Gly Tyr Pro Ser Val Phe Tyr Gly Asp
                355             360             365

Tyr Tyr Gly Ile Pro Thr His Gly Val Pro Ala Met Lys Ser Lys Ile
        370             375             380

Asp Pro Ile Leu Glu Ala Arg Gln Lys Tyr Ala Tyr Gly Lys Gln Asn
385             390             395             400

Asp Tyr Leu Asp His His Asn Met Ile Gly Trp Thr Arg Glu Gly Asn
                405             410             415

Thr Ala His Pro Asn Ser Gly Leu Ala Thr Ile Met Ser Asp Gly Pro
                420             425             430

Gly Gly Asn Lys Trp Met Tyr Val Gly Arg Asn Lys Ala Gly Gln Val
        435             440             445
```

-continued

```
Trp Arg Asp Ile Thr Gly Asn Arg Ser Gly Thr Val Thr Ile Asn Ala
    450             455             460

Asp Gly Trp Gly Asn Phe Ser Val Asn Gly Gly Ser Val Ser Ile Trp
465             470             475             480

Val Asn Asn

<210> SEQ ID NO 42
<211> LENGTH: 399
<212> TYPE: PRT
<213> ORGANISM: Artificial Sequence
<220> FEATURE:
<223> OTHER INFORMATION: domain AB variant

<400> SEQUENCE: 42

His His Asn Gly Thr Asn Gly Thr Met Met Gln Tyr Phe Glu Trp Tyr
1               5               10              15

Leu Pro Asn Asp Gly Asn His Trp Asn Arg Leu Arg Ser Asp Ala Ser
                20              25              30

Asn Leu Lys Asp Lys Gly Ile Thr Ala Val Trp Ile Pro Pro Ala Trp
            35              40              45

Lys Gly Ala Ser Gln Asn Asp Val Gly Tyr Gly Ala Tyr Asp Leu Tyr
        50              55              60

Asp Leu Gly Glu Phe Asn Gln Lys Gly Thr Val Arg Thr Lys Tyr Gly
65              70              75              80

Thr Arg Asn Gln Leu Gln Ala Ala Val Thr Ala Leu Lys Ser Asn Gly
                85              90              95

Ile Gln Val Tyr Gly Asp Val Val Met Asn His Lys Gly Gly Ala Asp
            100             105             110

Ala Thr Glu Trp Val Arg Ala Val Glu Val Asn Pro Ser Asn Arg Asn
        115             120             125

Gln Glu Val Ser Gly Asp Tyr Thr Ile Glu Ala Trp Thr Lys Phe Asp
    130             135             140

Phe Pro Gly Arg Gly Asn Thr His Ser Asn Phe Lys Trp Arg Trp Tyr
145             150             155             160

His Phe Asp Gly Val Asp Trp Asp Gln Ser Arg Gln Leu Gln Asn Arg
            165             170             175

Ile Tyr Lys Phe Arg Gly Asp Gly Lys Gly Trp Asp Trp Glu Val Asp
            180             185             190

Thr Glu Asn Gly Asn Tyr Asp Tyr Leu Met Tyr Ala Asp Ile Asp Met
        195             200             205

Asp His Pro Glu Val Val Asn Glu Leu Arg Asn Trp Gly Val Trp Tyr
    210             215             220

Thr Asn Thr Leu Gly Leu Asp Gly Phe Arg Ile Asp Ala Val Lys His
225             230             235             240

Ile Lys Tyr Ser Phe Thr Arg Asp Trp Leu Thr His Val Arg Asn Thr
            245             250             255

Thr Gly Lys Asn Met Phe Ala Val Ala Glu Phe Trp Lys Asn Asp Ile
        260             265             270

Gly Ala Ile Glu Asn Tyr Leu Ser Lys Thr Asn Trp Asn His Ser Val
        275             280             285

Phe Asp Val Pro Leu His Tyr Asn Leu Tyr Asn Ala Ser Arg Ser Gly
    290             295             300

Gly Asn Tyr Asp Met Arg Gln Ile Phe Asn Gly Thr Val Val Gln Arg
305             310             315             320
```

```
His Pro Thr His Ala Val Thr Phe Val Asp Asn His Asp Ser Gln Pro
            325                 330                 335

Glu Glu Ala Leu Glu Ser Phe Val Glu Glu Trp Phe Lys Pro Leu Ala
            340                 345                 350

Tyr Ala Leu Thr Leu Thr Arg Asp Gln Gly Tyr Pro Ser Val Phe Tyr
            355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly
385                 390                 395

<210> SEQ ID NO 43
<211> LENGTH: 86
<212> TYPE: PRT
<213> ORGANISM: Artificial Sequence
<220> FEATURE:
<223> OTHER INFORMATION: domain C variant

<400> SEQUENCE: 43

Lys Gln Asn Asp Tyr Leu Asp His His Asn Met Ile Gly Trp Thr Arg
1               5                   10                  15

Glu Gly Asn Thr Ala His Pro Asn Ser Gly Leu Ala Thr Ile Met Ser
            20                  25                  30

Asp Gly Pro Gly Gly Asn Lys Trp Met Tyr Val Gly Arg Asn Lys Ala
            35                  40                  45

Gly Gln Val Trp Arg Asp Ile Thr Gly Asn Arg Ser Gly Thr Val Thr
    50                  55                  60

Ile Asn Ala Asp Gly Trp Gly Asn Phe Ser Val Asn Gly Gly Ser Val
65                  70                  75                  80

Ser Ile Trp Val Asn Asn
                85

<210> SEQ ID NO 44
<211> LENGTH: 86
<212> TYPE: PRT
<213> ORGANISM: Artificial Sequence
<220> FEATURE:
<223> OTHER INFORMATION: domain C variant

<400> SEQUENCE: 44

Thr Gln Arg Asp Tyr Leu Asp His Pro Asp Val Ile Gly Trp Thr Arg
1               5                   10                  15

Glu Gly Asp Gly Val His Ala Asp Ser Gly Leu Ala Thr Leu Ile Ser
            20                  25                  30

Asp Gly Pro Gly Gly Ser Lys Trp Met Glu Val Gly Lys Asn Asn Ala
            35                  40                  45

Gly Glu Val Trp Tyr Asp Met Thr Gly Asn Gln Thr Asn Thr Val Thr
    50                  55                  60

Ile Asn Lys Asp Gly Trp Gly Gln Phe His Val Ser Gly Gly Ser Val
65                  70                  75                  80

Ser Ile Tyr Val Gln Gln
                85

<210> SEQ ID NO 45
<211> LENGTH: 484
<212> TYPE: PRT
<213> ORGANISM: Artificial Sequence
<220> FEATURE:
<223> OTHER INFORMATION: recombinant amylase variant
```

```
<400> SEQUENCE: 45

Asp Thr Val Asn Asn Gly Thr Leu Met Gln Tyr Phe Glu Trp Tyr Ala
1               5                   10                  15

Pro Asn Asp Gly Asp His Trp Asn Arg Leu Arg Thr Asp Ala Glu Asn
                20                  25                  30

Leu Ala Gln Lys Gly Ile Thr Ser Val Trp Ile Pro Pro Ala Tyr Lys
            35                  40                  45

Gly Thr Thr Gln Asn Asp Val Gly Tyr Gly Ala Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Leu Lys Ser Ala Ile Asp Ala Leu His Lys Lys Asn Ile
                85                  90                  95

Asn Val Tyr Gly Asp Val Val Met Asn His Lys Gly Gly Ala Asp Tyr
            100                 105                 110

Thr Glu Thr Val Thr Ala Val Glu Val Asp Pro Ser Asn Arg Asn Ile
            115                 120                 125

Glu Val Ser Gly Asp Tyr Glu Ile Ser Ala Trp Thr Gly Phe Asn Phe
        130                 135                 140

Pro Gly Arg Gly Asp Ser Tyr Ser Asn Phe Lys Trp Lys Trp Tyr His
145                 150                 155                 160

Phe Asp Gly Thr Asp Trp Asp Glu Gly Arg Lys Leu Asn Arg Ile Tyr
                165                 170                 175

Lys Phe Ile Gly Lys Ala Trp Asp Trp Glu Val Ser Ser Glu Asn Gly
            180                 185                 190

Asn Tyr Asp Tyr Leu Met Tyr Ala Asp Leu Asp Phe Asp His Pro Asp
            195                 200                 205

Val Ala Asn Glu Met Lys Lys Trp Gly Thr Trp Tyr Ala Asn Glu Leu
        210                 215                 220

Asn Leu Asp Gly Phe Arg Leu Asp Ala Val Lys His Ile Asp His Glu
225                 230                 235                 240

Tyr Leu Arg Asp Trp Val Asn His Val Arg Gln Gln Thr Gly Lys Glu
                245                 250                 255

Met Phe Thr Val Ala Glu Tyr Trp Gln Asn Asp Ile Gln Thr Leu Asn
                260                 265                 270

Asn Tyr Leu Ala Lys Val Asn Tyr Asn Gln Ser Val Phe Asp Ala Pro
            275                 280                 285

Leu His Tyr Asn Phe His Tyr Ala Ser Thr Gly Asn Gly Asn Tyr Asp
        290                 295                 300

Met Arg Asn Ile Leu Lys Gly Thr Val Val Ala Asn His Pro Thr Leu
305                 310                 315                 320

Ala Val Thr Leu Val Glu Asn His Asp Ser Gln Pro Gly Gln Ser Leu
                325                 330                 335

Glu Ser Val Val Ser Pro Trp Phe Lys Pro Leu Ala Tyr Ala Phe Ile
            340                 345                 350

Leu Thr Arg Ala Glu Gly Tyr Pro Ser Val Phe Tyr Gly Asp Tyr Tyr
            355                 360                 365

Gly Thr Lys Gly Asn Ser Asn Tyr Glu Ile Pro Ala Leu Lys Asp Lys
        370                 375                 380

Ile Asp Pro Ile Leu Thr Ala Arg Lys Asn Phe Ala Tyr Gly Thr Gln
385                 390                 395                 400

Arg Asp Tyr Phe Asp His Pro Asp Val Ile Gly Trp Thr Arg Glu Gly
                405                 410                 415
```

-continued

Asp Ser Val His Ala Asn Ser Gly Leu Ala Thr Leu Ile Ser Asp Gly
          420                     425                     430

Pro Gly Gly Ser Lys Trp Met Asp Val Gly Lys Asn Asn Ala Gly Glu
          435                     440                     445

Val Trp Tyr Asp Ile Thr Gly Asn Gln Thr Asn Thr Val Thr Ile Asn
          450                     455                     460

Lys Asp Gly Trp Gly Gln Phe Gln Val Ser Gly Gly Ser Val Ser Ile
465                     470                     475                     480

Tyr Val Gln Arg

<210> SEQ ID NO 46
<211> LENGTH: 86
<212> TYPE: PRT
<213> ORGANISM: Artificial Sequence
<220> FEATURE:
<223> OTHER INFORMATION: domain C variant

<400> SEQUENCE: 46

Thr Gln Arg Asp Tyr Phe Asp His Pro Asp Val Ile Gly Trp Thr Arg
1                     5                      10                      15

Glu Gly Asp Ser Val His Ala Asn Ser Gly Leu Ala Thr Leu Ile Ser
          20                     25                      30

Asp Gly Pro Gly Gly Ser Lys Trp Met Asp Val Gly Lys Asn Asn Ala
          35                     40                      45

Gly Glu Val Trp Tyr Asp Ile Thr Gly Asn Gln Thr Asn Thr Val Thr
          50                     55                      60

Ile Asn Lys Asp Gly Trp Gly Gln Phe Gln Val Ser Gly Gly Ser Val
65                     70                      75                      80

Ser Ile Tyr Val Gln Arg
                85

<210> SEQ ID NO 47
<211> LENGTH: 486
<212> TYPE: PRT
<213> ORGANISM: Artificial Sequence
<220> FEATURE:
<223> OTHER INFORMATION: recombinant amylase variant

<400> SEQUENCE: 47

Asp Thr Val Asn Asn Gly Thr Leu Met Gln Tyr Phe Glu Trp Tyr Ala
1                     5                      10                      15

Pro Asn Asp Gly Asn His Trp Asn Arg Leu Arg Thr Asp Ala Glu Asn
          20                     25                      30

Leu Ala Gln Lys Gly Ile Thr Ser Val Trp Ile Pro Pro Ala Tyr Lys
          35                     40                      45

Gly Thr Thr Gln Asn Asp Val Gly Tyr Gly Ala Tyr Asp Leu Tyr Asp
          50                     55                      60

Leu Gly Glu Phe Asn Gln Lys Gly Thr Val Arg Thr Lys Tyr Gly Thr
65                     70                      75                      80

Lys Ala Gln Leu Lys Ser Ala Ile Asp Ala Leu His Lys Lys Asn Ile
          85                     90                      95

Asp Val Tyr Gly Asp Val Val Met Asn His Lys Gly Gly Ala Asp Tyr
          100                    105                     110

Thr Glu Thr Val Thr Ala Val Glu Val Asp Pro Ser Asn Arg Asn Val
          115                    120                     125

Glu Val Ser Gly Asp Tyr Glu Ile Ser Ala Trp Thr Gly Phe Asn Phe
          130                    135                     140

-continued

```
Pro Gly Arg Gly Asp Ser Tyr Ser Asn Phe Lys Trp Lys Trp Tyr His
145                 150                 155                 160

Phe Asp Gly Thr Asp Trp Asp Glu Gly Arg Lys Leu Asn Arg Ile Tyr
                165                 170                 175

Lys Phe Arg Gly Ile Gly Lys Ala Trp Asp Trp Glu Val Ser Ser Glu
                180                 185                 190

Asn Gly Asn Tyr Asp Tyr Leu Met Tyr Ala Asp Leu Asp Phe Asp His
                195                 200                 205

Pro Asp Val Ala Asn Glu Met Lys Lys Trp Gly Thr Trp Tyr Ala Asn
    210                 215                 220

Glu Leu Asn Leu Asp Gly Phe Arg Leu Asp Ala Val Lys His Ile Asp
225                 230                 235                 240

His Glu Tyr Leu Arg Asp Trp Val Asn His Val Arg Gln Gln Thr Gly
                245                 250                 255

Lys Glu Met Phe Ala Val Ala Glu Tyr Trp Gln Asn Asp Ile Gln Thr
                260                 265                 270

Leu Asn Asn Tyr Leu Ala Lys Val Asn Tyr Asn Gln Ser Val Phe Asp
                275                 280                 285

Ala Pro Leu His Tyr Asn Phe His Tyr Ala Ser Lys Gly Asn Gly Asn
    290                 295                 300

Tyr Asp Met Arg Asn Ile Leu Lys Gly Thr Val Val Ala Asn His Pro
305                 310                 315                 320

Thr Leu Ala Val Thr Leu Val Glu Asn His Asp Ser Gln Pro Gly Gln
                325                 330                 335

Ser Leu Glu Ser Val Val Ser Pro Trp Phe Lys Pro Leu Ala Tyr Ala
                340                 345                 350

Phe Ile Leu Thr Arg Ala Glu Gly Tyr Pro Ser Val Phe Tyr Gly Asp
                355                 360                 365

Tyr Tyr Gly Thr Lys Gly Asn Ser Asn Tyr Glu Ile Pro Ala Leu Lys
    370                 375                 380

Asp Lys Ile Asp Pro Ile Leu Thr Ala Arg Lys Asn Tyr Ala Tyr Gly
385                 390                 395                 400

Thr Gln Arg Asp Tyr Phe Asp His Pro Asp Val Ile Gly Trp Thr Arg
                405                 410                 415

Glu Gly Asp Ser Val His Ala Asn Ser Gly Leu Ala Thr Leu Ile Ser
                420                 425                 430

Asp Gly Pro Gly Gly Ala Lys Trp Met Asp Val Gly Lys Asn Asn Ala
                435                 440                 445

Gly Glu Ile Trp Tyr Asp Ile Thr Gly Asn Gln Thr Asn Thr Val Thr
    450                 455                 460

Ile Asn Lys Asp Gly Trp Gly Gln Phe Gln Val Ser Gly Gly Ser Val
465                 470                 475                 480

Ser Ile Tyr Val Gln Arg
                485
```

```
<210> SEQ ID NO 48
<211> LENGTH: 86
<212> TYPE: PRT
<213> ORGANISM: Artificial Sequence
<220> FEATURE:
<223> OTHER INFORMATION: domain C variant

<400> SEQUENCE: 48

Thr Gln Arg Asp Tyr Phe Asp His Pro Asp Val Ile Gly Trp Thr Arg
1               5                   10                  15
```

```
Glu Gly Asp Ser Val His Ala Asn Ser Gly Leu Ala Thr Leu Ile Ser
        20                  25                  30

Asp Gly Pro Gly Gly Ala Lys Trp Met Asp Val Gly Lys Asn Asn Ala
        35                  40                  45

Gly Glu Ile Trp Tyr Asp Ile Thr Gly Asn Gln Thr Asn Thr Val Thr
    50                  55                  60

Ile Asn Lys Asp Gly Trp Gly Gln Phe Gln Val Ser Gly Gly Ser Val
65                  70                  75                  80

Ser Ile Tyr Val Gln Arg
                85
```

```
<210> SEQ ID NO 49
<211> LENGTH: 485
<212> TYPE: PRT
<213> ORGANISM: Artificial Sequence
<220> FEATURE:
<223> OTHER INFORMATION: recombinant amylase variant

<400> SEQUENCE: 49
```

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
        20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
            165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
            245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
    275                 280                 285
```

```
Phe Asp Val Pro Leu His Tyr Asn Leu Tyr Asn Ala Ser Arg Ser Gly
    290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Asp Gln Gly Tyr Pro Ser Val Phe Tyr
                355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Thr
385                 390                 395                 400

Gln Arg Asp Tyr Phe Asp His Pro Asp Val Ile Gly Trp Thr Arg Glu
                405                 410                 415

Gly Asp Ser Val His Ala Asn Ser Gly Leu Ala Thr Leu Ile Ser Asp
                420                 425                 430

Gly Pro Gly Gly Ser Lys Trp Met Asp Val Gly Lys Asn Asn Ala Gly
                435                 440                 445

Glu Val Trp Tyr Asp Ile Thr Gly Asn Gln Thr Asn Thr Val Thr Ile
    450                 455                 460

Asn Lys Asp Gly Trp Gly Gln Phe Gln Val Ser Gly Gly Ser Val Ser
465                 470                 475                 480

Ile Tyr Val Gln Arg
                485
```

```
<210> SEQ ID NO 50
<211> LENGTH: 485
<212> TYPE: PRT
<213> ORGANISM: Artificial Sequence
<220> FEATURE:
<223> OTHER INFORMATION: recombinant amylase variant

<400> SEQUENCE: 50

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
                100                 105                 110

Ala Thr Glu Trp Val Arg Ala Val Glu Val Asn Pro Ser Asn Arg Asn
            115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160
```

```
His Phe Asp Gly Val Asp Trp Asp Gln Ser Arg Gln Leu Gln Asn Arg
            165             170             175

Ile Tyr Lys Phe Arg Gly Asp Gly Lys Gly Trp Asp Trp Glu Val Asp
            180             185             190

Thr Glu Asn Gly Asn Tyr Asp Tyr Leu Met Tyr Ala Asp Ile Asp Met
            195             200             205

Asp His Pro Glu Val Val Asn Glu Leu Arg Asn Trp Gly Val Trp Tyr
    210             215             220

Thr Asn Thr Leu Gly Leu Asp Gly Phe Arg Ile Asp Ala Val Lys His
225             230             235             240

Ile Lys Tyr Ser Phe Thr Arg Asp Trp Leu Thr His Val Arg Asn Thr
            245             250             255

Thr Gly Lys Asn Met Phe Ala Val Ala Glu Phe Trp Lys Asn Asp Ile
            260             265             270

Gly Ala Ile Glu Asn Tyr Leu Ser Lys Thr Asn Trp Asn His Ser Val
            275             280             285

Phe Asp Val Pro Leu His Tyr Asn Leu Tyr Asn Ala Ser Arg Ser Gly
    290             295             300

Gly Asn Tyr Asp Met Arg Gln Ile Phe Asn Gly Thr Val Val Gln Arg
305             310             315             320

His Pro Thr His Ala Val Thr Phe Val Asp Asn His Asp Ser Gln Pro
            325             330             335

Glu Glu Ala Leu Glu Ser Phe Val Glu Glu Trp Phe Lys Pro Leu Ala
            340             345             350

Tyr Ala Leu Thr Leu Thr Arg Asp Gln Gly Tyr Pro Ser Val Phe Tyr
            355             360             365

Gly Asp Tyr Tyr Gly Ile Pro Thr His Gly Val Pro Ala Met Lys Ser
    370             375             380

Lys Ile Asp Pro Ile Leu Glu Ala Arg Gln Lys Tyr Ala Tyr Gly Thr
385             390             395             400

Gln Arg Asp Tyr Phe Asp His Pro Asp Val Ile Gly Trp Thr Arg Glu
            405             410             415

Gly Asp Ser Val His Ala Asn Ser Gly Leu Ala Thr Leu Ile Ser Asp
            420             425             430

Gly Pro Gly Gly Ala Lys Trp Met Asp Val Gly Lys Asn Asn Ala Gly
            435             440             445

Glu Ile Trp Tyr Asp Ile Thr Gly Asn Gln Thr Asn Thr Val Thr Ile
    450             455             460

Asn Lys Asp Gly Trp Gly Gln Phe Gln Val Ser Gly Gly Ser Val Ser
465             470             475             480

Ile Tyr Val Gln Arg
            485
```

```
<210> SEQ ID NO 51
<211> LENGTH: 400
<212> TYPE: PRT
<213> ORGANISM: Artificial Sequence
<220> FEATURE:
<223> OTHER INFORMATION: domain AB variant

<400> SEQUENCE: 51
```

```
Ala Thr Ile Asn Asn Gly Thr Leu Met Gln Tyr Phe Glu Trp Tyr Ala
1               5               10              15

Pro Asn Asp Gly Asn His Trp Lys Arg Leu His Thr Asp Ala Gly Asn
            20              25              30
```

```
Leu Ala Gln Lys Gly Ile Thr Ser Val Trp Ile Pro Pro Ala Tyr Lys
        35                  40                  45

Gly Thr Thr Gln Asn Asp Val Gly Tyr Gly Ala Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Leu Lys Ser Ala Ile Glu Ala Leu His Lys Gln Asn Ile
                85                  90                  95

Asn Val Tyr Gly Asp Val Val Met Asn His Lys Gly Gly Ala Asp Tyr
                100                 105                 110

Thr Glu Thr Val Thr Ala Val Glu Val Asp Arg Asn Asn Arg Asn Ile
                115                 120                 125

Glu Val Ser Gly Asp Tyr Glu Ile Asn Ala Trp Thr Gly Phe Asn Phe
        130                 135                 140

Pro Gly Arg Gly Asp Thr His Ser Asn Phe Lys Trp Lys Trp Tyr His
145                 150                 155                 160

Phe Asp Gly Thr Asp Trp Asp Glu Gly Arg Lys Leu Asn Arg Ile Tyr
                165                 170                 175

Lys Phe Arg Gly Ile Gly Lys Ala Trp Asp Trp Glu Val Ser Ser Glu
                180                 185                 190

Asn Gly Asn Tyr Asp Tyr Leu Met Tyr Ala Asp Leu Asp Phe Asp His
                195                 200                 205

Pro Asp Val Ala Asn Glu Met Lys Asn Trp Gly Thr Trp Tyr Ala Asn
        210                 215                 220

Glu Leu Asn Leu Asp Gly Phe Arg Leu Asp Ala Val Lys His Ile Asp
225                 230                 235                 240

His Glu Tyr Leu Arg Asp Trp Val Asn His Val Arg Gln Gln Thr Gly
                245                 250                 255

Lys Glu Met Phe Thr Val Ala Glu Tyr Trp Gln Asn Asp Ile Gln Thr
                260                 265                 270

Leu Asn Asn Tyr Leu Ala Lys Val Asn Tyr Asn Gln Ser Val Phe Asp
        275                 280                 285

Ala Pro Leu His Tyr Asn Phe His Tyr Ala Ser Lys Gly Asn Gly Asn
        290                 295                 300

Tyr Asp Met Arg Asn Ile Leu Asn Gly Thr Val Met Gln Asn His Pro
305                 310                 315                 320

Ala Leu Ala Val Thr Leu Val Glu Asn His Asp Ser Gln Pro Gly Gln
                325                 330                 335

Ser Leu Glu Ser Val Val Ser Pro Trp Phe Lys Pro Leu Ala Tyr Ala
                340                 345                 350

Phe Ile Leu Thr Arg Ala Glu Gly Tyr Pro Ser Val Phe Tyr Gly Asp
        355                 360                 365

Tyr Tyr Gly Thr Ser Gly Asn Ser Ser Tyr Glu Ile Pro Ala Leu Lys
        370                 375                 380

Asp Lys Ile Asp Pro Ile Leu Met Ala Arg Lys Asn Phe Ala Tyr Gly
385                 390                 395                 400
```

<210> SEQ ID NO 52
<211> LENGTH: 485
<212> TYPE: PRT
<213> ORGANISM: Artificial Sequence
<220> FEATURE:
<223> OTHER INFORMATION: recombinant amylase variant

<400> SEQUENCE: 52

-continued

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
            115                 120                 125

Gln Glu Val Ser Gly Asp Tyr Thr Ile Glu Ala Trp Thr Lys Phe Asp
        130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
        210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
        290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Asp Gln Gly Tyr Pro Ser Val Phe Tyr
            355                 360                 365

Gly Asp Tyr Tyr Gly Ile Pro Thr His Gly Val Pro Ala Met Lys Ser
        370                 375                 380

Lys Ile Asp Pro Ile Leu Glu Ala Arg Gln Lys Tyr Ala Tyr Gly Thr
385                 390                 395                 400

Gln Arg Asp Tyr Leu Asp His Pro Asp Val Ile Gly Trp Thr Arg Glu
                405                 410                 415
```

-continued

```
Gly Asp Gly Val His Ala Asp Ser Gly Leu Ala Thr Leu Ile Ser Asp
            420                 425                 430

Gly Pro Gly Gly Ser Lys Trp Met Glu Val Gly Lys Asn Asn Ala Gly
            435                 440                 445

Glu Val Trp Tyr Asp Met Thr Gly Asn Gln Thr Asn Thr Val Thr Ile
            450                 455                 460

Asn Lys Asp Gly Trp Gly Gln Phe His Val Ser Gly Gly Ser Val Ser
465                 470                 475                 480

Ile Tyr Val Gln Gln
                485

<210> SEQ ID NO 53
<211> LENGTH: 485
<212> TYPE: PRT
<213> ORGANISM: Artificial Sequence
<220> FEATURE:
<223> OTHER INFORMATION: recombinant amylase variant

<400> SEQUENCE: 53

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
            50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
                100                 105                 110

Ala Thr Glu Trp Val Arg Ala Val Glu Val Asn Pro Ser Asn Arg Asn
            115                 120                 125

Gln Glu Val Ser Gly Asp Tyr Thr Ile Glu Ala Trp Thr Lys Phe Asp
            130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
                180                 185                 190

Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
            210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
            275                 280                 285
```

```
Phe Asp Val Pro Leu His Tyr Asn Leu Tyr Asn Ala Ser Arg Ser Gly
    290             295             300

Gly Asn Tyr Asp Met Arg Gln Ile Phe Asn Gly Thr Val Val Gln Arg
305             310             315             320

His Pro Thr His Ala Val Thr Phe Val Asp Asn His Asp Ser Gln Pro
            325             330             335

Glu Glu Ala Leu Glu Ser Phe Val Glu Glu Trp Phe Lys Pro Leu Ala
            340             345             350

Tyr Ala Leu Thr Leu Thr Arg Asp Gln Gly Tyr Pro Ser Val Phe Tyr
            355             360             365

Gly Asp Tyr Tyr Gly Ile Pro Thr His Gly Val Pro Ala Met Lys Ser
    370             375             380

Lys Ile Asp Pro Ile Leu Glu Ala Arg Gln Lys Tyr Ala Tyr Gly Thr
385             390             395             400

Gln Arg Asp Tyr Leu Asp His Pro Asp Val Ile Gly Trp Thr Arg Glu
            405             410             415

Gly Asp Gly Val His Ala Asp Ser Gly Leu Ala Thr Leu Met Ser Asp
            420             425             430

Gly Pro Gly Gly Ser Lys Trp Met Glu Val Gly Lys Asn Asn Ala Gly
            435             440             445

Glu Val Trp Tyr Asp Ile Thr Gly Asn Gln Thr Asn Thr Val Thr Ile
    450             455             460

Asn Lys Asp Gly Trp Gly Gln Phe His Val Ser Gly Gly Ser Val Ser
465             470             475             480

Ile Tyr Val Gln Gln
                485

<210> SEQ ID NO 54
<211> LENGTH: 483
<212> TYPE: PRT
<213> ORGANISM: Artificial Sequence
<220> FEATURE:
<223> OTHER INFORMATION: recombinant amylase variant

<400> SEQUENCE: 54

His His Asn Gly Thr Asn Gly Thr Met Met Gln Tyr Phe Glu Trp Tyr
1               5               10              15

Leu Pro Asn Asp Gly Asn His Trp Asn Arg Leu Arg Ser Asp Ala Ser
            20              25              30

Asn Leu Lys Asp Lys Gly Ile Thr Ala Val Trp Ile Pro Pro Ala Trp
            35              40              45

Lys Gly Ala Ser Gln Asn Asp Val Gly Tyr Gly Ala Tyr Asp Leu Tyr
    50              55              60

Asp Leu Gly Glu Phe Asn Gln Lys Gly Thr Val Arg Thr Lys Tyr Gly
65              70              75              80

Thr Arg Asn Gln Leu Gln Ala Ala Val Thr Ala Leu Lys Ser Asn Gly
            85              90              95

Ile Gln Val Tyr Gly Asp Val Val Met Asn His Lys Gly Gly Ala Asp
            100             105             110

Ala Thr Glu Trp Val Arg Ala Val Glu Val Asn Pro Ser Asn Arg Asn
            115             120             125

Gln Glu Val Ser Gly Asp Tyr Thr Ile Glu Ala Trp Thr Lys Phe Asp
    130             135             140

Phe Pro Gly Arg Gly Asn Thr His Ser Asn Phe Lys Trp Arg Trp Tyr
145             150             155             160
```

```
His Phe Asp Gly Val Asp Trp Asp Gln Ser Arg Gln Leu Gln Asn Arg
            165             170             175

Ile Tyr Lys Phe Arg Gly Lys Gly Trp Asp Trp Glu Val Asp Thr Glu
            180             185             190

Asn Gly Asn Tyr Asp Tyr Leu Met Tyr Ala Asp Ile Asp Met Asp His
            195             200             205

Pro Glu Val Val Asn Glu Leu Arg Asn Trp Gly Val Trp Tyr Thr Asn
    210             215             220

Thr Leu Gly Leu Asp Gly Phe Arg Ile Asp Ala Val Lys His Ile Lys
225             230             235             240

Tyr Ser Phe Thr Arg Asp Trp Leu Thr His Val Arg Asn Thr Thr Gly
            245             250             255

Lys Asn Met Phe Ala Val Ala Glu Phe Trp Lys Asn Asp Ile Gly Ala
            260             265             270

Ile Glu Asn Tyr Leu Ser Lys Thr Asn Trp Asn His Ser Val Phe Asp
            275             280             285

Val Pro Leu His Tyr Asn Leu Tyr Asn Ala Ser Arg Ser Gly Gly Asn
    290             295             300

Tyr Asp Met Arg Gln Ile Phe Asn Gly Thr Val Val Gln Arg His Pro
305             310             315             320

Thr His Ala Val Thr Phe Val Asp Asn His Asp Ser Gln Pro Glu Glu
            325             330             335

Ala Leu Glu Ser Phe Val Glu Glu Trp Phe Lys Pro Leu Ala Tyr Ala
            340             345             350

Leu Thr Leu Thr Arg Asp Gln Gly Tyr Pro Ser Val Phe Tyr Gly Asp
            355             360             365

Tyr Tyr Gly Ile Pro Thr His Gly Val Pro Ala Met Lys Ser Lys Ile
    370             375             380

Asp Pro Ile Leu Glu Ala Arg Gln Lys Tyr Ala Tyr Gly Thr Gln Arg
385             390             395             400

Asp Tyr Leu Asp His Pro Asp Val Ile Gly Trp Thr Arg Glu Gly Asp
            405             410             415

Gly Val His Ala Asp Ser Gly Leu Ala Thr Leu Met Ser Asp Gly Pro
            420             425             430

Gly Gly Ser Lys Trp Met Glu Val Gly Lys Asn Asn Ala Gly Glu Val
            435             440             445

Trp Tyr Asp Ile Thr Gly Asn Gln Thr Asn Thr Val Thr Ile Asn Lys
    450             455             460

Asp Gly Trp Gly Gln Phe His Val Ser Gly Gly Ser Val Ser Ile Tyr
465             470             475             480

Val Gln Gln
```

<210> SEQ ID NO 55
<211> LENGTH: 1449
<212> TYPE: DNA
<213> ORGANISM: Artificial Sequence
<220> FEATURE:
<223> OTHER INFORMATION: recombinant amylase variant

<400> SEQUENCE: 55

```
catcacaatg gcacaaacgg taccatgatg caatattttg agtggtacct cccaaatgac        60
ggaaatcatt ggaacagatt gcgctctgat gcaagcaacc ttaaagataa gggcataaca        120
gctgtttgga ttccgccagc atggaaaggc gccagtcaaa acgacgtcgg atatggagcg        180
tacgatctgt atgatttagg cgagtttaat cagaaaggca cagtaagaac gaaatatgga        240
```

-continued

```
accaggaatc aacttcaggc ggctgtgacg gccctcaagt ctaatggcat tcaggtgtat      300
ggcgacgttg tgatgaacca caaaggagga gctgatgcga cagaatgggt tagagcagtc      360
gaagtaaatc ctagcaatcg aaaccaggag gtgagcggtg attacacaat cgaggcatgg      420
accaaattcg actttcctgg acgtggcaac acacatagta attttaagtg gagatggtat      480
cacttcgatg gcgtagactg ggatcaatct agacagttac agaaccggat ctacaaattt      540
cgcggaaaag gctgggattg ggaagttgat acggagaacg gcaattatga ttacttgatg      600
tacgcagata tcgacatgga tcatccggaa gtggtcaatg agttacgtaa ttggggcgtc      660
tggtacacta acacactggg ccttgacgga ttccgcattg atgcggttaa acatatcaaa      720
tattcgttta cgcgcgactg gttaactcat gtccggaata caacaggcaa gaatatgttt      780
gctgttgcag aattttggaa aaacgatatc ggcgcgattg aaaattatct ttcaaagact      840
aactggaatc attccgtatt cgacgtgcct ttgcactaca acctgtataa tgcgtcgcgc      900
tccggcggta actatgacat gcgacaaatc ttcaacggca cagtcgttca gcgtcacccc      960
acacacgctg ttacatttgt agacaaccat gacagccaac cggaggaagc tcttgaaagc     1020
ttcgtagaag aatggtttaa gcctctggcc tatgcgctga cgcttacgcg ggatcaagga     1080
tacccgagcg tgttttatgg agattactat ggcattccga cgcatggcgt gccagccatg     1140
aaatcaaaaa ttgatccgat actcgaagcc agacaaaaat atgcatatgg tactcaacgg     1200
gattatttgg accatccgga tgtcattggt tggacccgtg aaggagatgg agtacatgct     1260
gactctggct tagccacact gatgtccgat ggtcctggag gctcaaaatg gatggaagtg     1320
ggtaagaaca atgcaggtga agtttggtat gatattaccg gcaatcagac gaatacggtt     1380
actattaata aagatggttg gggacaattt catgtctcag gcggctctgt ctcaatctat     1440
gttcagcag                                                             1449
```

<210> SEQ ID NO 56
<211> LENGTH: 86
<212> TYPE: PRT
<213> ORGANISM: Artificial Sequence
<220> FEATURE:
<223> OTHER INFORMATION: domain C motif
<220> FEATURE:
<221> NAME/KEY: misc_feature
<222> LOCATION: (3)..(3)
<223> OTHER INFORMATION: Xaa can be any proteinogenic amino acid
<220> FEATURE:
<221> NAME/KEY: misc_feature
<222> LOCATION: (20)..(21)
<223> OTHER INFORMATION: Xaa can be any proteinogenic amino acid
<220> FEATURE:
<221> NAME/KEY: misc_feature
<222> LOCATION: (23)..(24)
<223> OTHER INFORMATION: Xaa can be any proteinogenic amino acid
<220> FEATURE:
<221> NAME/KEY: misc_feature
<222> LOCATION: (29)..(29)
<223> OTHER INFORMATION: Xaa can be any proteinogenic amino acid
<220> FEATURE:
<221> NAME/KEY: misc_feature
<222> LOCATION: (36)..(36)
<223> OTHER INFORMATION: Xaa can be any proteinogenic amino acid
<220> FEATURE:
<221> NAME/KEY: misc_feature
<222> LOCATION: (38)..(38)
<223> OTHER INFORMATION: Xaa can be any proteinogenic amino acid
<220> FEATURE:
<221> NAME/KEY: misc_feature
<222> LOCATION: (42)..(42)
<223> OTHER INFORMATION: Xaa can be any proteinogenic amino acid
<220> FEATURE:

```
<221> NAME/KEY: misc_feature
<222> LOCATION: (51)..(51)
<223> OTHER INFORMATION: Xaa can be any proteinogenic amino acid
<220> FEATURE:
<221> NAME/KEY: misc_feature
<222> LOCATION: (53)..(53)
<223> OTHER INFORMATION: Xaa can be any proteinogenic amino acid
<220> FEATURE:
<221> NAME/KEY: misc_feature
<222> LOCATION: (67)..(67)
<223> OTHER INFORMATION: Xaa can be any proteinogenic amino acid
<220> FEATURE:
<221> NAME/KEY: misc_feature
<222> LOCATION: (70)..(70)
<223> OTHER INFORMATION: Xaa can be any proteinogenic amino acid
<220> FEATURE:
<221> NAME/KEY: misc_feature
<222> LOCATION: (74)..(74)
<223> OTHER INFORMATION: Xaa can be any proteinogenic amino acid
<220> FEATURE:
<221> NAME/KEY: misc_feature
<222> LOCATION: (76)..(77)
<223> OTHER INFORMATION: Xaa can be any proteinogenic amino acid
<220> FEATURE:
<221> NAME/KEY: misc_feature
<222> LOCATION: (80)..(80)
<223> OTHER INFORMATION: Xaa can be any proteinogenic amino acid
<220> FEATURE:
<221> NAME/KEY: misc_feature
<222> LOCATION: (84)..(84)
<223> OTHER INFORMATION: Xaa can be any proteinogenic amino acid
<220> FEATURE:
<221> NAME/KEY: misc_feature
<222> LOCATION: (86)..(86)
<223> OTHER INFORMATION: Xaa can be any proteinogenic amino acid

<400> SEQUENCE: 56

Thr Gln Xaa Asp Tyr Leu Asp His Pro Asp Val Ile Gly Trp Thr Arg
1               5                   10                  15

Glu Gly Asp Xaa Xaa His Xaa Xaa Ser Gly Leu Ala Xaa Leu Met Ser
            20                  25                  30

Asp Gly Pro Xaa Gly Xaa Lys Trp Met Xaa Val Gly Lys Asn Asn Ala
        35                  40                  45

Gly Glu Xaa Trp Xaa Asp Ile Thr Gly Asn Gln Thr Asn Thr Val Thr
    50                  55                  60

Ile Asn Xaa Asp Gly Xaa Gly Gln Phe Xaa Val Xaa Xaa Gly Ser Xaa
65                  70                  75                  80

Ser Ile Tyr Xaa Gln Xaa
                85
```

AMYLASE VARIANTS

CROSS REFERENCE TO RELATED APPLICATIONS

This is the U.S. national phase of International Application No. PCT/EP2020/073514, filed Aug. 22, 2020, which claims priority to U.S. Patent Application Nos. 62/890,325, filed Aug. 22, 2019; 62/905,893, filed Sep. 25, 2019; and 62/930,806, filed Nov. 5, 2019.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "191304_Seqlisting.txt", which was created on Feb. 3, 2022 and is 177,551 bytes in size. The subject matter of the Sequence Listing is incorporated herein in its entirety by reference.

TECHNICAL FIELD

In the present invention new amylase enzymes are provided. More specifically, genetically engineered amylase enzymes, compositions comprising the enzymes, and methods of using the enzymes or compositions comprising the enzymes. The genetically engineered amylase enzymes are useful in many different applications such as laundry detergents, dish washing detergents, and cleaning products for homes, industry, vehicle care, baking, animal feed, pulp and paper processing, starch processing, and ethanol production. Amylases have been employed in the removal of starch stains and have been added to various compositions such as cleaning products. A lot of these applications require the use of the amylases being either stable at elevated temperatures or within a denaturing condition. Thus, the need exists for genetically engineered amylase enzymes with improved properties, in particular with improved stability and improved performance.

SUMMARY OF THE INVENTION

The present invention refers to an isolated, synthetic, or recombinant polypeptide having alpha-amylase activity comprising an A and B domain and a C domain wherein the amino acid sequence of the A and B domain is at least 75% identical to the amino acid sequence of SEQ ID NO: 42 and the amino acid sequence of the C domain is at least 75% identical to the amino acid sequence of SEQ ID NO: 44.

Preferably, the polypeptide having alpha-amylase activity consists of an A and B domain and a C domain wherein the amino acid sequence of the A and B domain is at least 75% identical to the amino acid sequence of SEQ ID NO: 42 and the amino acid sequence of the C domain is at least 75% identical to the amino acid sequence of SEQ ID NO: 44.

Preferably, the A and B domain of the polypeptide having alpha-amylase activity has at least 80%, at least 85%, at least 90%, at least 91%, at least 92%, at least 93%, at least 94%, at least 95%, at least, 96%, at least 97%, at least 98%, at least 99% or 100% sequence identity to the A and B domain having the amino acid sequence of SEQ ID NO: 42.

Preferably, the C domain of the polypeptide having alpha-amylase activity has at least 80%, at least 85%, at least 90%, at least 91%, at least 92%, at least 93%, at least 94%, at least 95%, at least 96%, at least 97%, at least 98%, at least 99% or 100% sequence identity to the C domain having the amino acid sequence of SEQ ID NO: 44.

Preferably, the isolated, synthetic, or recombinant polypeptide having alpha-amylase activity comprises a substitution, deletion, and/or insertion at one or more positions.

Preferably, the isolated, synthetic, or recombinant polypeptide having alpha-amylase activity comprises the sequence TQXDYLDHPDVIGWTREGDXX HXXSGLAXLMSDGPXGXKWMXVGKN-NAGEXWXDITGNQTNTVTINXDGXGQF XVXXGSXSIYXQX (SEQ ID NO: 56), wherein X can be any amino acid.

Preferably, the isolated, synthetic, or recombinant polypeptide having alpha-amylase activity has one or more amino acid residues selected from the group consisting of 402R, H; 419S, G, D; 420V, I; 422A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K according to the numbering of SEQ ID NO: 39, preferably selected from the group consisting of 402R; 419D; 420V; 422A; 423D; 428A, T; 435R; 437S; 441E; 444K; 450V; 452Y; 466K; 469W; 473R; 475S; 476G; 479V; 483V; and 485Q according to the numbering of SEQ ID NO: 39.

Preferably, the isolated, synthetic, or recombinant polypeptide having alpha-amylase activity comprises a substitution at one or more positions selected from the group consisting of 430 and 454, preferably the amylase of the present invention comprises amino acid residues 430M and/or 430I, preferably the substitution resulting in 430M and/or 454I, preferably the substitution being selected from the group consisting of I430M and M454I, according to the numbering of SEQ ID NO: 39. Preferably, the isolated, synthetic, or recombinant polypeptide having alpha-amylase activity comprises an amino acid residue at one or more of the amino acid positions selected from the group consisting of 401, 403, 405, 411, 413, 415, 424, 426, 428, 432, 455, 477, 479 and 481 (according to the numbering of SEQ ID NO: 39) as present in SEQ ID NO: 39.

Preferably, the isolated, synthetic, or recombinant polypeptide having alpha-amylase activity comprises an amino acid residue at one or more of the amino acid positions selected from the group consisting of 309, 313, 347, 348, 350, 351, 354, 355, 358, 359, 388, 389, 392 and 396 (according to the numbering of SEQ ID NO: 39) as present in SEQ ID NO: 40.

Preferably, the isolated, synthetic, or recombinant polypeptide having alpha-amylase activity comprises a deletion of one or more amino acids corresponding to positions 181, 182, 183 and 184 corresponding to the numbering of SEQ ID NO: 39, preferably a deletion of two or more amino acids corresponding to positions 181, 182, 183 and 184, preferably a deletion of amino acids corresponding to positions 181 and 182, 182 and 183, or 183 and 184 (according to the numbering of SEQ ID NO: 39).

Preferably, the isolated, synthetic, or recombinant polypeptide having alpha-amylase activity comprises a substitution at one or more positions selected from the group consisting of 9, 130, 195, 206, 244, 202, 179, 181, 186, and 190 according to the numbering of SEQ ID NO: 39, preferably one or more substitutions selected from the group consisting of M9L, E130V, N195F, I206L, S244Q, M202L, K179L, R181E, G186E/N/Q/S and E190P according to the numbering of SEQ ID NO: 39.

Preferably, the isolated, synthetic, or recombinant polypeptide having alpha-amylase activity comprises:

(a) an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37;

(b) an amino acid sequence encoded by a polynucleotide having at least at least 80%, at least 85%, at least 90%, at least 91%, at least 92%, at least 93%, at least 94%, at least 95%, at least, 96%, at least 97%, at least 98%, at least 99% or 100% sequence identity with SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, (c) an amino acid sequence encoded by a polynucleotide that hybridizes under high stringency conditions with the complement of
  (i) a coding sequence of SEQ ID NO:54, SEQ 1D NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37; or
  (ii) a polynucleotide shown in SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38; or
(d) a fragment of (a), (b), or (c) having amylase activity.

Preferably, the isolated, synthetic, or recombinant polypeptide having alpha-amylase activity comprises an increase in expression, activity, thermostability, stability, performance in laundry, specific activity, substrate specificity, pH-dependent activity, pH-dependent stability, oxidative stability, Ca2+ dependency, or any combination thereof compared to the amylase shown in SEQ ID NO: 39 or SEQ ID NO: 40, preferably, the amylase has an increase in thermostability compared to the amylase shown in SEQ ID NO: 39 or SEQ ID NO: 40.

The present invention also refers to an isolated, a synthetic, or a recombinant nucleic acid comprising:
  (a) a nucleic acid sequence having at least at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, wherein the nucleic acid encodes a polypeptide having amylase activity;

(b) a nucleic acid sequence encoding a polypeptide having at least at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the polypeptide has amylase activity or any polypeptide described herein having amylase activity;

(c) a polynucleotide that hybridizes under high stringency conditions with the complement of
  (i) a coding sequence of SEQ ID NO:54, SEQ 1D NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37; or
  (ii) a polynucleotide shown in SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38;
(d) a fragment of (a), (b), or (c), wherein the fragment encodes a polypeptide having amylase activity; or
(e) a nucleic acid sequence fully complementary to any of (a) to (d).

The present invention also refers to a nucleic acid construct comprising the polynucleotide as described herein.

The present invention also refers to an expression vector comprising the polynucleotide or the nucleic acid construct as described herein.

The present invention also refers to a host cell comprising the polynucleotide as described herein, the nucleic acid construct as described herein, or the expression vector as described herein.

The present invention also refers to a composition comprising the isolated, synthetic, or recombinant polypeptide having alpha-amylase activity as described herein.

Preferably, the composition further comprising at least one second enzyme selected from the group consisting of: a second amylase, a lipase, a protease, a cellulase, a laccase, a mannanase, a pectinase, xylanase, and a nuclease.

The present invention also refers to a method of making the isolated, synthetic, or recombinant polypeptide having alpha-amylase as described herein, comprising: providing a nucleic acid sequence encoding the polypeptide, transforming the nucleic acid sequence into an expression host, cultivating the expression host to produce the polypeptide, and optionally purifying the polypeptide.

The present invention also refers to a method of preparing a dough or a baked product prepared from the dough, the method comprising adding the isolated, synthetic, or recombinant polypeptide having alpha-amylase activity as described herein to the dough and baking it.

The present invention also refers to a method of use of the isolated, synthetic, or recombinant polypeptide having alpha-amylase activity as described herein, for processing starch, for cleaning or washing textiles, hard surfaces, or dishes, for making ethanol, for processing pulp or paper, or for feeding an animal.

The present invention also refers to a method of making an isolated, synthetic, or recombinant polypeptide having alpha-amylase activity comprising the step of making a hybrid from at least two different amylases, wherein the hybrid comprises an A and B domain and a C domain and wherein the amino acid sequence of the A and B domain is at least 75% identical to the amino acid sequence of SEQ ID NO: 42 and the amino acid sequence of the C domain is at least 75% identical to the amino acid sequence of SEQ ID NO: 44.

The present invention also refers to a method of use of a C domain of a first amylase said C domain having an amino acid sequence which has at least 75% identity to the amino acid sequence of SEQ ID NO: 44 for improving one or more properties selected from the group consisting of stability, pH profile, expression, activity, thermostability, specific activity, substrate specificity, pH-dependent activity, pH-dependent stability, oxidative stability, Ca2+ dependency, performance in laundry, processing starch, cleaning textiles, cleaning hard surfaces, cleaning dishes, making ethanol, processing pulp or paper, and feeding an animal of a second alpha amylase having an A and B domain with at least 75% identity to the amino acid sequence of SEQ ID NO: 42 said use comprising replacing the C domain of the second alpha-amylase with the C domain of the first alpha-amylase.

BRIEF DESCRIPTION OF THE DRAWINGS

FIG. 1 shows the results of an enzyme heat challenge (80°C.) experiment descriped in Example 3 herein. The figure illustrates that replacing the C domain of SEQ ID NO:41 with the C domain of SEQ ID NO:40 resulting in amylase having SEQ ID NO:54 (with additional mutations at the positons 430 and 454) greatly increases the thermostability and that using closely related C domains (like closely related to the C domain of the SEQ ID NO: 40) gives rise to hybrids being also more stable than SEQ ID NO: 41, underlined by the results obtained with SEQ ID: 9.

DETAILED DESCRIPTION OF THE INVENTION

An enzyme is a biological molecule (polypeptide) comprising a sequence of amino acid residues, wherein the enzyme can catalyze a reaction. Hence, enzymes are catalytically active proteins or polypeptides. Enzyme names are determined based on the recommendations of the Nomenclature Committee of the International Union of Biochemistry and Molecular Biology (IUBMB). Enzymes are defined by an EC (Enzyme Commission) number, recommended name, alternative names (if any), catalytic activity, and other factors. Enzymes herein may be identified by polypeptide sequences (also called amino acid sequences herein). The polypeptide sequence specifies the three-dimensional structure including the "active site" of an enzyme which in turn determines the catalytic activity of the same. Polypeptide sequences may be identified by a SEQ ID NO.

Enzymes are obtained from or derived from many different sources including: plants; animals; bacteria, archaea, fungi, yeast, environmental samples containing DNA that encodes an enzyme, or enzymes can be synthetic generated in a laboratory. For example, bacterial sources of enzymes include enzymes derived from *Bacillus, Streptomyces, E. coli* and *Pseudomonas*; fungal sources of enzymes include enzymes derived from *Aspergillus, Fusarium, Thermomyces* and *Trichoderma*; yeast sources of enzymes include enzymes derived from *Pichia*, and *Saccharomyces*.

The World Intellectual Property Office (WIPO) Standard ST.25 (1998) provides that the amino acid residues should be represented in the sequence listing using the following three-letter symbols with the first letter as a capital. The table below provides an overview of the amino acid identifiers as well as the corresponding DNA codons that encode the amino acid using the standard genetic standard.

The DNA codons that encode amino acid residues can be different depending organism that is used and slightly different tables for translation of the genetic code may apply. A compilation of such non-standard code translation tables is maintained at the NCBI.

A "parent" polypeptide amino acid sequence is the starting sequence for introduction of mutations (e.g. by introducing one or more (fragments) amino acid substitutions, insertions, deletions, or a combination thereof) to the sequence, resulting in "variants" of the parent polypeptide amino acid sequences. A parent includes: A wild-type polypeptide amino acid sequence or synthetically generated polypeptide amino acid sequence that is used as starting sequence for introduction of (further) changes.

A "variant polypeptide" refers to an enzyme that differs from its parent in its amino acid sequence. The differences between the parent polypeptide and variant polypeptide can be one single amino acid residue, or more than one amino acid residue. The more than one amino acid residue and be consecutive amino acid residues or non-consecutive amino acid residues. The consecutive amino acid residues can be four consecutive amino acid residues; five consecutive amino acid residues; eight consecutive amino acid residues; nine consecutive amino acid residues; eleven consecutive amino acid residues; thirteen consecutive amino acid residues; or fourteen consecutive amino acid residues. While the definition below describes variants in the context of amino acid changes, nucleic acids may be similarly modified, e.g. by substitutions.

A "mature polypeptide" means an enzyme in its final form including any post-translational modifications, glycosylation, phosphorylation, truncation, N-terminal modifications, C-terminal modifications, signal sequence deletion. A mature polypeptide can vary depending upon the expression system, vector, promoter, and/or production process.

A "synthetic" or "artificial" compound is produced by in vitro chemical or enzymatic synthesis.

The term "non-naturally occurring" refers to a (poly) nucleotide, amino acid, (poly)peptide, enzyme, protein, cell, organism, or other material that is not present in its original naturally occurring environment or source. Preferably, the amylase of the present invention is a non-naturally occurring amylase.

Variant polynucleotide and variant polypeptide sequences may be defined by their sequence identity when compared to a parent sequence. Sequence identity usually is provided as "% sequence identity" or "% identity". For calculation of sequence identities, in a first step a sequence alignment is produced. According to this invention, a pairwise global alignment is produced, meaning that two sequences are aligned over their complete length, which is usually produced by using a mathematical approach, called alignment algorithm.

According to the invention, the alignment is generated by using the algorithm of Needleman and Wunsch (J. Mol. Biol. (1979) 48, p. 443-453). Preferably, the program "NEEDLE" (The European Molecular Biology Open Software Suite (EMBOSS)) is used for the purposes of the current invention, with using the programs default parameter (polynucleotides: gap open=10.0, gap extend=0.5 and matrix=EDNAFULL; polypeptides: gap open=10.0, gap extend=0.5 and matrix=EBLOSUM62).

After aligning two sequences, in a second step, an identity value is determined from the alignment produced.

For this purpose, the %-identity is calculated by dividing the number of identical residues by the length of the alignment region which is showing the respective sequence of the present invention over its complete length multiplied with 100: %-identity=(identical residues/length of the alignment region which is showing the respective sequence of the present invention over its complete length) *100.

For calculating the percent identity of two nucleic acid sequences the same applies as for the calculation of percent identity of two amino acid sequences with some specifications. For nucleic acid sequences encoding for a protein the pairwise alignment shall be made over the complete length of the coding region of the sequence of this invention from start to stop codon excluding introns. Introns present in the other sequence, to which the sequence of this invention is compared, may also be removed for the pairwise alignment. Percent identity is then calculated by %-identity=(identical residues/length of the alignment region which is showing the sequence of the invention from start to stop codon excluding introns over their complete length)*100. After aligning two sequences, in a second step, an identity value is determined from the alignment produced.

Moreover, the preferred alignment program for nucleic acid sequences implementing the Needleman and Wunsch algorithm (J. Mol. Biol. (1979) 48, p. 443-453) is "NEEDLE" (The European Molecular Biology Open Software Suite (EMBOSS)) with the programs default parameters (gapopen=10.0, gapextend=0.5 and matrix=EDNAFULL).

Sequences, having identical or similar regions with a sequence of this invention, and which shall be compared with a sequence of this invention to determine % identity, can easily be identified by various ways that are within the skill in the art, for instance, using publicly available computer methods and programs such as BLAST, BLAST-2, available for example at NCBI.

Variant polypeptides may be defined by their sequence similarity when compared to a parent sequence. Sequence similarity usually is provided as "% sequence similarity" or "%-similarity". % sequence similarity takes into account that defined sets of amino acids share similar properties, e.g. by their size, by their hydrophobicity, by their charge, or by other characteristics. Herein, the exchange of one amino acid with a similar amino acid may be called "conservative mutation". Similar amino acids according to the invention are defined as follows, which shall also apply for determination of %-similarity according to this invention, which is also in accordance with the BLOSUM62 matrix as for example used by program "NEEDLE", which is one of the most used amino acids similarity matrix for database searching and sequence alignments:

Amino acid A is similar to amino acids S
Amino acid D is similar to amino acids E; N
Amino acid E is similar to amino acids D; K; Q
Amino acid F is similar to amino acids W; Y
Amino acid H is similar to amino acids N; Y
Amino acid I is similar to amino acids L; M; V
Amino acid K is similar to amino acids E; Q; R
Amino acid L is similar to amino acids I; M; V
Amino acid M is similar to amino acids I; L; V
Amino acid N is similar to amino acids D; H; S
Amino acid Q is similar to amino acids E; K; R
Amino acid R is similar to amino acids K; Q Amino acid S is similar to amino acids A; N; T
Amino acid T is similar to amino acids S
Amino acid V is similar to amino acids I; L; M
Amino acid W is similar to amino acids F; Y
Amino acid Y is similar to amino acids F; H; W Conservative amino acid substitutions may occur over the full length of the sequence of a polypeptide sequence of a functional protein such as an enzyme. In one embodiment, such mutations are not pertaining the functional domains of an enzyme. In one embodiment, conservative mutations are not pertaining the catalytic centers of an enzyme.

For calculation of sequence similarity, in a first step a sequence alignment is produced as described above. After aligning two sequences, in a second step, a similarity value is determined from the alignment produced.

For this purpose, the %-similarity is calculated by dividing the number of identical residues plus the number of similar residues by the length of the alignment region which is showing the sequence of the invention over its complete length multiplied with 100: %-similarity=[(identical residues+ similar residues)/length of the alignment region which is showing the sequence of the invention over its complete length]*100.

The invention relates to a polypeptide having amylase activity comprising an amino acid sequence that is at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to any one of the full length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37.

The invention further relates to a polynucleotide encoding a variant polypeptide of the invention. The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length. A "gene" is a DNA segment carrying a certain genetic information.

A "parent" polynucleotide acid sequence is the starting sequence for introduction of mutations to the sequence, resulting in "variants" of said parent polynucleotide sequence. A "variant polynucleotide" refers to a polynucleotide that encodes an enzyme and the variant polynucleotide differs from its parent polynucleotide in its nucleic acid sequence.

The polynucleotide of the invention in one aspect has a nucleic acid sequence which is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical when compared to any one of the full length polynucleotide sequence of SEQ ID NO:55, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38.

Preferably, the polynucleotide is a codon-optimized polynucleotide for improving expression in a specific host cell.

"Substitutions" are described by providing the original amino acid followed by the number of the position within the amino acid sequence, followed by the substituted amino acid. A specific amino acid residue may be substituted with any of the 19 amino acid residues different from the original one. For example, the substitution of histidine at position 120 with alanine is designated as "His120Ala" or "H120A". Alternative substitutions at an amino acid position are indicated as follows "His120Ala, Leu" or "H120A, L". It is understood herein that instead of the indicated specific substitutions alternative substitutions using conservative amino acid alternatives can be used.

Amino acid deletions are described by providing the original amino acid of the parent enzyme followed by the number of the position within the amino acid sequence, followed by *. Accordingly, the deletion of glycine at position 150 is designated as "Gly150*" or G150*". Alternatively, deletions are indicated by e.g. "deletion of D183 and G184".

Amino acid insertions are described by providing the original amino acid of the parent enzyme followed by the number of the position within the amino acid sequence, followed by the original amino acid and the additional amino acid. For example, an insertion at position 180 of lysine next to glycine is designated as "Gly180GlyLys" or "G180GK". When more than one amino acid residue is inserted, such as e.g. a Lys and Ala after Gly180 this may be indicated as: Gly180GlyLysAla or G195GKA.

In cases where a substitution and an insertion occur at the same position, this may be indicated as S99SD+S99A or in short S99AD.

The one or more amino acid substitution of the variant polypeptides can be one or more conservative amino acid substitution. A "conservative amino acid substitution" or "related amino acid" means replacement of one amino acid residue in an amino acid sequence with a different amino acid residue having a similar property at the same position compared to the parent amino acid sequence. Some examples of a conservative amino acid substitution include but are not limited to replacing a positively charged amino acid residue with a different positively charged amino acid residue; replacing a polar amino acid residue with a different polar amino acid residue; replacing a non-polar amino acid residue with a different non-polar amino acid residue, replacing a basic amino acid residue with a different basic amino acid residue, or replacing an aromatic amino acid residue with a different aromatic amino acid residue.

"Enzymatic activity" means at least one catalytic effect exerted by an enzyme. Enzymatic activity is expressed as units per milligram of enzyme (specific activity) or molecules of substrate transformed per minute per molecule of enzyme (molecular activity). Enzymatic activity can be specified by the enzymes actual function, e.g. proteases exerting proteolytic activity by catalyzing hydrolytic cleavage of peptide bonds, lipases exerting lipolytic activity by hydrolytic cleavage of ester bonds, amylases activity involves (endo)hydrolysis of glucosidic linkages in polysaccharides, etc.

Enzymatic activity may change during storage or operational use of the enzyme. The term "enzyme stability" relates to the retention of enzymatic activity as a function of time during storage or operation. The term "storage" herein means to indicate the fact of products or compositions or formulations being stored from the time of being manufactured to the point in time of being used in final application.

Retention of enzymatic activity as a function of time during storage may be called "storage stability" herein.

To determine and quantify changes in catalytic activity of enzymes stored or used under certain conditions over time, the "initial enzymatic activity" is measured under defined conditions at time zero (100%) and at a certain point in time later (x %). By comparison of the values measured, a potential loss of enzymatic activity can be determined in its extent. The extent of enzymatic activity loss determines an enzymes stability or non-stability.

Parameters influencing the enzymatic activity of an enzyme and/or storage stability and/or operational stability are for example pH, temperature, chelators, and presence of oxidative substances.

A variant polypeptide may be active over a broad pH at any single point within the range from about pH 4.0 to about pH 12.0. The variant polypeptides enzyme may be active over a range of pH 5.0 to pH 11.0, pH 6.0 to pH 10.0, and pH 7.0 to pH 9.0. In another embodiment, the variant polypeptides enzyme may be active over a pH 7.1 to pH 8.9, pH 7.2 to pH 8.8, pH 7.3 to pH 8.7, pH 7.4 to pH 8.6, pH 7.5 to pH 8.5. The variant polypeptides may be active at pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6 pH 8.7, pH 8.8 pH 8.9, pH 9.0, pH 9.1, pH 9.2, pH 9.3, pH 9.4, pH 9.5, pH 9.6, pH 9.7, pH 9.8, pH 9.9, pH 10.0, pH 10.1, pH 10.2, pH 10.3, pH 10.4, pH 10.5, pH 10.6, pH 10.7, pH 10.8, pH 10.9, pH 11.0, pH 11.1, pH 11.2, pH 11.3, pH 11.4, pH 11.5, pH 11.6, pH 11.7, pH 11.8, pH 11.9, pH 12.0, pH 12.1, pH 12.2, pH 12.3, pH 12.4, and pH 12.5, pH 12.6, pH 12.7, pH 12.8, pH 12.9, or higher.

A "pH stability", refers to the ability of an enzyme to exert enzymatic activity at a specific pH range.

The variant polypeptides may be active over a broad temperature, wherein the temperature is any point in the range from about 10° C. to about 95° C. The variant polypeptides may be active at a temperature range from 10° C. to 55° C., 10° C. to 50° C., 10° C. to 45° C., 10° C. to 40° C., 10° C. to 35° C., 10° C. to 30° C., or 10° C. to 25° C. The variant polypeptides may be active at a temperature range from 20° C. to 55° C., 20° C. to 50° C., 20° C. to 45° C., 20° C. to 40° C., 20° C. to 35° C., 20° C. to 30° C., or 20° C. to 25° C. The variant polypeptides are active at a temperature of at least 10° C., 11 C, 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., or higher temperatures.

The terms "thermal stability" and "thermostability" refer to the ability of a protein to exert catalytic activity at a specific temperature range. Enzymes thermostability may be characterized by what is known as the Tso value (also called half-life, see above). The Tso indicates the temperature at which 50% residual enzymatic activity is still present after thermal inactivation for a certain time when compared with a reference sample which has not undergone thermal treatment.

In one embodiment, the variant polypeptides improve the thermostability compared to the parent molecule. In another embodiment the variant polypeptides improve the thermostability by 3° C., 4° C., 5° C., 6° C., 7° C., 8° C., 9° C., 10° C., 11 C, 12° C., 13° C., 14° C., 15° C., 16° C., 17° C., 18° C., 19° C., 20° C., or more degrees C. when compared to the parent polypeptide. In another embodiment, the thermostability increase is measured at a temperature between 65° C. and 100° C.

The thermostability increase can be measured at 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., and/or 100° C. In another embodiment, the thermostability increase is measured at a temperature of 70° C. In another embodiment, the thermostability increase is measured at a temperature of 80° C. In another embodiment, the thermostability increase is measured a temperature of 90° C. In one embodiment, the thermostability is improved at 70° C., at 80° C., or at 90° C., preferably at 70° C. In another embodiment, the thermostability is improved in a temperature range between 65° C. and 90° C., preferably between 70° C. and 85° C., preferably between 70° C. and 80° C.

In one embodiment, the variant polypeptide is a fragment of the full-length amino acid sequence and the fragment has amylase activity.

A "Fragment", or "subsequence" as used herein are a portion of a polynucleotide or an amino acid sequence.

The term "functional fragment" refers to any nucleic acid or amino acid sequence which comprises merely a part of the full-length amino acid sequence, respectively, but still has the same or similar activity and/or function. Preferably, the functional fragment is at least 75% identical, at least 76% identical, at least 77% identical, at least 78% identical, at least 79% identical, at least 80% identical, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, or at least 99.5% identical to the full length amino acid sequence original sequence. The functional fragment comprises contiguous nucleic acids or amino acids compared to the original nucleic acid or original amino acid sequence, respectively.

A-, B- and C-Domains:

The structure of alpha-amylases comprises three distinct domains A, B and C, see, e.g., Machius et al., 1995, *J. Mol. Biol.* 246: 545-559. The term "domain" means a region of a polypeptide that in itself forms a distinct and independent substructure of the whole molecule. Alpha-amylases consist of a beta/alpha-8 barrel harboring the active site residues, which is denoted the A-domain, a rather long loop between the beta-sheet and alpha-helix 3, which is denoted the B-domain (together; "A and B domain"), and a C-domain and in some cases also an additional carbohydrate binding domain (e.g., WO 2005/001064; Machius et al., supra).

The domains of an alpha-amylase can be determined by structure analysis such as using crystallographic techniques. An alternative method for determining the domains of an alpha-amylase is by sequence alignment of the amino acid sequence of the alpha-amylase with another alpha-amylase for which the domains have been determined. The sequence that aligns with, e.g., the C-domain sequence in the alpha-amylase for which the C-domain has been determined can be considered the C-domain for the given alpha-amylase.

A and B Domain:

The term "A and B domain" as used herein means these two domains taken as one unit, whereas the C domain is another unit of the alpha-amylases. Thus, the amino acid sequence of the "A and B domain" is understood as one consecutive sequence or one part of a sequence of an alpha-amylase comprising an "A and B domain" and other, additional domains (such as the C domain). Thus, the term "the A and B domain has at least 75% sequence identity to SEQ ID NO: 42" means that the amino acid sequence that form the A and B domain has at least 75% sequence identity to SEQ ID NO: 42. As used herein, the "A and B domain" of an alpha-amylase corresponds to amino acids 1-399 of SEQ ID NO: 39.

AB Domain Donor:

the term AB domain donor as used herein means the alpha-amylase from which the A and B domain is obtained. Thus, for the A and B domain having the amino acid sequence of SEQ ID NO: 42, the AB domain donor is the alpha-amylase of SEQ ID NO: 39.

C Domain:

As used herein, the "C domain" of an alpha-amylase corresponds to amino acids 400-485 of for example SEQ ID NO: 39. Thus, the C domain of an alpha amylase may be found by alignment of said alpha amylase with the alpha amylase of SEQ ID NO: 39 The part of said alpha amylase that aligns with amino acids 400-485 of SEQ ID NO: 39 is according to the present invention "the C domain" of the alpha amylase. Thus, for instance, the C domain of the alpha amylase having the amino acid sequence of SEQ ID NO: 40 is made up of amino acids 401-486 disclosed here as SEQ ID NO: 44.

Carbohydrate Binding Domain or Carbohydrate Binding Module (CBM):

The amylases comprised of catalytic modules (A, B and C domain) may further comprise one or more non-catalytic CBMs (carbohydrate-binding modules, also called carbohydrate binding domain or specifically for amylases starch binding domains). CBMs can improve the association of the enzyme with the substrate. CBMs are attached to the C-domain.

Alpha-amylases of the present invention comprise three domains; A, B and C domains. Preferably, the amylase of the present invention does not comprise a carbohydrate binding domain. Preferably, alpha-amylases of the present invention consists only of the three domains being A, B and C domain.

The inventors of the present invention have surprisingly found, that a polypeptide which is a hybrid of the A and B domain from a first alpha amylase (the "AB domain donor") of SEQ ID NO: 39 or variants thereof and the C domain from a second alpha amylase (the "C domain donor") of SEQ ID NO: 40 or variants thereof has improved properties, compared to the alpha-amylase of the AB domain donor (SEQ ID NO: 39 or variants thereof) and the alpha-amylase of the C domain donor (SEQ ID NO: 40 or variants thereof) and/or even the alpha-amylase of SEQ ID NO: 41, which is the alpha-amylase of SEQ ID NO: 39 having a stability improving mutation, i.e., a deletion at amino acid position 182 and 183 according to the numbering of SEQ ID NO: 39.

The A and B domain of the alpha-amylase having the amino acid sequence of SEQ ID NO: 39 were determined to correspond to amino acids 1-399. This sequence is also disclosed as SEQ ID NO: 42 herein. The C domain of the amino acid sequence of SEQ ID NO: 39 was determined to correspond to amino acids 400-485 (disclosed herein as SEQ ID NO: 43). The C domain of the alpha-amylase having the amino acid sequence of SEQ ID NO: 40 was determined to correspond to amino acids 401-486 of SEQ ID NO: 40 and is also disclosed as SEQ ID NO: 44 herein. Thus, in one embodiment of the present invention, the polypeptide having alpha-amylase activity is a hybrid of amino acids 1-399 of SEQ ID NO: 39 or variants thereof and amino acids 401-486 of SEQ ID NO: 40 or variants thereof.

AB Domain Donors:

In one embodiment, the A and B domain is obtained from the alpha-amylase comprising the amino acid sequence of SEQ ID NO: 39 which A and B domain is also disclosed herein as SEQ ID NO: 42. In one embodiment of the present invention, the amino acid sequence forming the A and B domain has at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 42.

Other suitable AB domain donors are alpha-amylases closely related to the alpha-amylase of SEQ ID NO: 39. Preferably, AB domain donors are alpha-amylases having at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase of SEQ ID NO: 39. Preferably, AB domain donors are alpha-amylases having at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase of SEQ ID NO: 41.

Alternatively, AB domain donors are alpha-amylases having at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase of SEQ ID NO: 40.

C Domain Donors:

The most preferred C domain donor is the alpha-amylase disclosed as SEQ ID NO: 40 from which the C domain is determined to correspond to amino acids 401-486 which is also disclosed as SEQ ID NO: 44 herein. Accordingly, the invention relates in the most preferred embodiments to the above disclosed A and B domains fused with the C domain disclosed as SEQ ID NO: 44 or a C domain having at least 75% sequence identity hereto. In another embodiment the invention relates to alpha-amylases comprising the above disclosed A and B domains fused with a C domain having a sequence which is at least 80% identical to the sequence of SEQ ID NO: 44. In another embodiment the invention relates to alpha-amylases comprising the above disclosed A and B domains fused with a C domain having a sequence which is at least 85% identical to the sequence of SEQ ID NO: 44. In another embodiment the invention relates to alpha-amylases comprising the above disclosed A and B domains fused with a C domain having a sequence which is at least 90% identical to the sequence of SEQ ID NO: 44. In another embodiment the invention relates to alpha-amylases comprising the above disclosed A and B domains fused with a C domain having a sequence which is at least 95% identical to the sequence of SEQ ID NO: 44. In another embodiment the invention relates to alpha-amylases comprising the above disclosed A and B domains fused with a C domain having a sequence which is at least 97% identical to the sequence of SEQ ID NO: 44. In another embodiment the invention relates to alpha-amylases comprising the above disclosed A and B domains fused with a C domain having a sequence which is at least 98% identical to the sequence of SEQ ID NO: 44. In another embodiment the invention relates to alpha-amylases comprising the above disclosed A and B domains fused with a C domain having a sequence which is at least 99% identical to the sequence of SEQ ID NO: 44. In another embodiment the invention relates to alpha-amylases comprising the above disclosed A and B domains fused with a C domain having a sequence which is 100% identical to the sequence of SEQ ID NO: 44.

Suitable C domains which are at least 75% identical to the C domain of SEQ ID NO: 44 are the two C domains disclosed as SEQ ID NOs 46 and 48 herein. Respective hybrid amylases hereof are shown in SEQ ID NO: 49 and 50.

Preferably, C domain donors are alpha-amylases having at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase of SEQ ID NO: 40.

Alternatively, C domain donors are alpha-amylases having at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase of SEQ ID NO: 39.

Thus, in an alternative embodiment, in case AB domain donors are alpha-amylases having at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase of SEQ ID NO: 40, then C domain donors are alpha-amylases having at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase of SEQ ID NO: 39.

Hybrids

The present invention refers to amylases (i.e., polypeptides having amylase activity), which can be considered as hybrids between the amylase shown in SEQ ID NO: 39 and the amylase shown in SEQ ID NO: 40 and variants thereof having amylase activity. In one embodiment, the invention refers to hybrid amylases comprising an A and B domain from the amylase shown in SEQ ID NO. 39 and the C domain of the amylase shown in SEQ ID NO: 40 and variants thereof having amylase activity.

In an alternative embodiment, the invention refers to hybrid amylases comprising an A and B domain from the amylase shown in SEQ ID NO. 40 and the C domain of the amylase shown in SEQ ID NO: 39 and variants thereof having amylase activity.

Thus, the polypeptide of the present invention may be described as a hybrid or a fusion polypeptide in which a region of one polypeptide is fused at the N-terminus or the C-terminus of a region of another polypeptide. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779). The polypeptide according to the invention may alternatively be produced by synthetic gene construction by means known to the skilled person. Thus, it is not necessary that the A and B domain on the one hand and the C domain on the other hand of the claimed polypeptides are derived from different alpha amylases and fused together. They may e.g. also be synthetically produced for instance by introducing the respective amino acid substitutions in a parent amylase sequence and thereby creating a variant amylase, which equals to a hybrid sequence. Thus, the amylase of the present invention can be obtained by a method of making an isolated, synthetic, or recombinant polypeptide having alpha-amylase activity comprising the step of making a hybrid from at least two different amylases, wherein the hybrid comprises an A and B domain and a C domain and wherein the amino acid sequence of the A and B domain is at least 75% identical to the amino acid sequence of SEQ ID NO: 42 and the amino acid sequence of the C domain is at least 75% identical to the amino acid sequence of SEQ ID NO: 44. Alternatively, the amylase of the present invention can be obtained by a method comprising the step of modifying a parent amylase (preferably as shown in SEQ ID NO: 39 or SEQ ID NO: 40 or variants thereof) and introducing into this parent amylase amino acid substitutions at certain position, preferably at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, or 123 positions, preferably 1-123, preferably, at 1-29 positions, more preferably, at 1-20 or even more preferably, 1-10 positions.

Preferably, the parent amylase is an amylase shown in SEQ ID NO: 39 and within the C domain of SEQ ID NO: 39 one or more amino acid substitutions are introduced, preferably at 1, 2, 3, 4, 5, 6, 7, 8, 9, 10, 11, 12, 13, 14, 15, 16, 17, 18, 19, 20, 21, 22, 23, 24, 25, 26, 27, 28, or 29 positions, preferably, at 1-29 positions, more preferably, at 1-10 positions, to convert the amino acid sequence at these positions to SEQ ID NO: 40.

Preferably, the alpha-amylase has at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase shown in SEQ ID NO: 39 and within the C domain of SEQ ID NO: 39 the amino acid residue at one or more of the amino acid positions selected from the group consisting of the positions 400, 402, 408, 409, 410, 418, 419, 420, 422, 423, 429, 430, 437, 441, 444, 446, 449, 452, 454, 458, 459, 460, 466, 471, 473, 475, 482, 484, and 485 according to the numbering of SEQ ID NO: 39 is exchanged, preferably to an amino acid residue present in SEQ ID NO: 40.

Preferably, the alpha-amylase has at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase shown in SEQ ID NO: 39 and within the C domain of SEQ ID NO: 39 the amino acid sequence comprises one or more substitutions selected from the group consisting of K400T, N402R, H408P, N409D, M410V, N418D, T419G, A420V, P422A, N423D, I429L, M430I, N437S, Y441E, R444K, K446N, Q449E, R452Y, I454M, R458Q, S459T, G460N, A466K, N471Q, S473H, N475S, W482Y, N484Q, and N485Q according to the numbering of SEQ ID NO: 39.

Alternatively, the parent amylase is an amylase shown in SEQ ID NO: 40 and within the AB domain of SEQ ID NO: 40 one or more amino acid substitutions are introduced, preferably at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, or 123 positions, preferably 1-123, more preferably 1-100, even more preferably 1-50 positions, to convert the amino acid sequence at these positions to SEQ ID NO: 39.

Preferably, the alpha-amylase has at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase shown in SEQ ID NO: 40 and within the A and B domain of SEQ ID NO: 40 the amino acid residue at one or more of the amino acid positions selected from the group consisting of the positions 1, 2, 3, 4, 5, 9, 17, 25, 28, 29, 32, 35, 36, 41, 48, 51, 52, 82, 83, 86, 87, 89, 90, 93, 94, 95, 96, 98, 113, 116, 118, 123, 124, 125, 129, 136, 138, 142, 144, 150, 158, 165, 169, 170, 172, 174, 183, 186, 192, 193, 206, 208, 212, 214, 217, 218, 222, 225, 227, 229, 235, 242, 243, 244, 245, 246, 250, 251, 255, 256, 260, 263, 267, 269, 273, 274, 275, 276, 280, 282, 284, 286, 291, 297, 298, 299, 302, 303, 304, 311, 313, 318, 320, 323, 324, 328, 330, 337, 338, 339, 343, 345, 346, 355, 356, 360, 361, 374, 375, 376, 377, 378, 379, 382, 384, 391, 394, 395, and 396 according to the numbering of SEQ ID NO: 39 is exchanged, preferably to an amino acid residue present in SEQ ID NO: 39.

Preferably, the alpha-amylase has at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% to the alpha-amylase shown in SEQ ID NO: 40 and within the A and B domain of SEQ ID NO: 40 the amino acid sequence comprises one or more substitutions selected from the group consisting of the positions A1HH, A2H, T3N, I4G, N5T, L9M, A17L, K25N, H28R, T29S, G32S, A35K, Q36D, S41A, Y48W, T51A, T52S, K82R, A83N, K86Q, S87A, I89V, E90T, H93K, K94S, Q95N, N96G, N98Q, Y113A, T116W, T118R, D123N, R124P, N125S, I129Q, E136T, N138E, G142K, N144D, D150N, K158R, T165V, E169Q, G170S, K172Q, L173LQ, I183D, A186G, S192D, S193T, L206I, F208M, D212E, A214V, M217L, K218R, T222V, A225T, E227T, N229G, L235I, D242K, H243Y, E244S, Y245F, L246T, V250L, N251T, Q255N, Q256T, E260N, T263A, Y267F, Q269K, Q273G, T274A, L275I, N276E, A280S, V282T, Y284W, Q286H, A291V, F297L, H298Y, Y299N, K302R, G303S, N304G, N311Q, L313F, M318V, N320R, A323T, L324H, L328F, E330D, G337E, Q338E, S339A, V343F, S345E, P346E, F355L, I356T, A360D, E361Q, TSGN374I, S375P, S376T, Y377H, E378G, I379V, L382M, D384S, M391E, K394Q, N395K, and F396Y according to the numbering of SEQ ID NO: 39.

In one embodiment, the hybrid amylase comprises the A and B domain from an amylase having an amino acid sequence with at least 75% sequence identity to an amylase shown in SEQ ID NO. 39 and the C domain from an amylase having an amino acid sequence with at least 75% sequence identity to the amylase shown in SEQ ID NO: 40.

In one embodiment of the present invention, the amino acid sequence forming the A and B domain has at least 75% identity, such as at least 78%, at least 80%, at least 85%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 42, and the amino acid sequence forming the C domain has at least 75% identity to SEQ ID NO: 44.

The alpha-amylases may be produced by substituting the C domain or a portion thereof of an alpha-amylase with the C domain or a portion thereof of another alpha-amylase. When producing a hybrid alpha-amylase, no amino acids should be deleted or inserted in the linker region, wherein the linker region is understood herein as amino acid positions 380-420 according to the numbering of SEQ ID NO: 39. Preferably, amino acid positions 380-420 according to the numbering of SEQ ID NO: 39 of the amylase comprises amino acid residues as present in either SEQ ID NO: 39 and/or SEQ ID NO: 40. Preferably, amino acid positions 390-410 according to the numbering of SEQ ID NO: 39 of the amylase comprises amino acid residues as present in either SEQ ID NO: 39 and/or SEQ ID NO: 40. Preferably, amino acid positions 395-405 according to the numbering of SEQ ID NO: 39 of the amylase comprises amino acid residues as present in either SEQ ID NO: 39 and/or SEQ ID NO: 40. Preferably, the amylase comprises at amino acid positions 380-399 (according to the numbering of SEQ ID NO: 39) the amino acid residues of SEQ ID NO: 39. Preferably, the amylase comprises at amino acid positions 400-420 (according to the numbering of SEQ ID NO: 39) the amino acid residues of SEQ ID NO: 40.

Preferably, the isolated, synthetic, or recombinant poly-peptide having alpha-amylase activity comprises a substi-tution, deletion, and/or insertion at one or more positions.

Preferably, the isolated, synthetic, or recombinant poly-peptide having alpha-amylase activity comprises the sequence TQXDYLDHPD-VIGWTREGDXXHXXSGLAXLMSDGPXGXKWMXV-GKNNAGEXWXDITG
NQTNTVTINXDGXGQFXVXXGSXSIYXQX (SEQ ID NO: 56), wherein X can be any amino acid.

Preferably, the isolated, synthetic, or recombinant poly-peptide having alpha-amylase activity has one or more amino acid residues selected from the group consisting of 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K according to the numbering of SEQ ID NO: 39, preferably selected from the group consisting of 402R; 419D; 420V; 422A; 423D; 428A, T; 435R; 437S; 441E; 444K; 450V; 452Y; 466K; 469W; 473R; 475S; 476G; 479V; 483V; and 485Q according to the numbering of SEQ ID NO: 39.

In a further embodiment, the invention relates to a variant of the polypeptides disclosed above. The amylase of the invention may comprise additional substitutions, deletions, and/or insertions at one or more positions. The polypeptides may be mutated (substitution, deletion, and/or an insertion) in the A and B domain only, or in the C domain only or in both the A and B domain and the C domain. The polypeptide may be mutated (substitution, deletion, and/or an insertion) outside the A and B domain and the C domain in case additional residues are present, e.g., a carbohydrate binding domain. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine sequence, an antigenic epitope or a binding domain.

In one embodiment, the variant of the amylase of SEQ ID NO:54, 1, 3, 5, 7, 9, 11, 13, 15, 17, 19, 21, 23, 25, 27, 29, 31, 33, 35, or 37 comprising a substitution at one or more positions and having amylase activity comprises 1, 2, 3, 4, 5, 6, 7, 8, 9, 10, 11, 12, 13, 14, 15, 16, 17, 18, 19 or 20 substitutions, preferably, at 1-20 positions, more preferably, at 1-10 positions, preferably conservative substitutions.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of puta-tive contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide. Essential amino acids in the sequence of amino acids of SEQ ID NO: 39 are located at positions D236, E266 and D333, which are the catalytic residues. These should preferable not be mutated. Single or multiple amino acid substitutions, dele-tions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sei. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Preferred mutations are deletions of at one or more, preferably at least 2, amino acids positions selected from 181, 182, 183 and 184, such as amino acids 181+182, or 182+183, or 181+183 or 181+184 of SEQ 1D NO: 39. Hereby the molecule is considerably stabilized. In a pre-ferred embodiment of the invention, the amino acids corre-sponding to 182 and 183 in SEQ ID NO: 39 are deleted. In one embodiment, the hybrid amylase of the present invention comprises the A and B domain of SEQ ID NO: 39, or a variant as disclosed herein, and the C domain from an alpha amylase of SEQ ID NO: 40, or a variant as disclosed herein, and further comprises a deletion of the amino acids corresponding to 182 and 183 in SEQ ID NO: 39. Such variant is disclosed for example as SEQ ID NO:54 herein.

In other embodiment of the invention, in the hybrid amylase comprises amino acid substitutions within the interface of the domain C and the A and B domain in order to avoiding steric clashes. In one embodiment preferred substitutions are substitutions within the C domain of the donor amylase (such as SEQ ID NO: 44) into the amino acid of the C domain to be replaced (such as SEQ ID NO: 43) at the equal position. Equal positions can be defined by aligning both sequences. Preferred positions for these mutations are analyzed by inspection of structural model. Preferred, but not restricted to, are substitutions at one or more of the following amino acid positions within the donor C domain: 401, 403, 405, 411, 413, 415, 424, 426, 428, 430, 432, 454, 455, 477, 479 and 481 (numbering according to SEQ ID NO: 39). Preferably, the polypeptide having amylase activity comprises an amino acid residue at one or more of the amino acid positions selected from the group consisting of 401, 403, 405, 411, 413, 415, 424, 426, 428, 430, 432, 454, 455, 477, 479 and 481 (according to the numbering of SEQ ID NO: 39) as present in SEQ ID NO: 39.

In another embodiment preferred substitutions are substitutions within the A and B domain of the C domain acceptor amylase (such as SEQ ID NO: 42) into the amino acid of the A and B domain of the C domain donor amylase (such as SEQ ID NO: 51) present at the equal position. Equal positions can be defined by aligning both sequences. Preferred positions for these mutations are analyzed by inspection of structural model. Preferred, but not restricted to, are substitutions at one or more of the following amino acid positions within the A and B domain of the C domain acceptor amylase; preferably within the A and B domain of SEQ ID NO: 39: 309, 313, 347, 348, 350, 351, 354, 355, 358, 359, 388, 389, 392 and 396 (numbering according to SEQ ID NO: 39). Preferably, the polypeptide having amylase activity comprises an amino acid residue at one or more of the amino acid positions selected from the group consisting of 309, 313, 347, 348, 350, 351, 354, 355, 358, 359, 388, 389, 392 and 396 (according to the numbering of SEQ ID NO: 39) as present in SEQ ID NO: 40. An example for the adaptation of the interface within a hybrid amylase consisting out of an A and B domain as given in SED ID NO: 42 and the C domain as given in SEQ ID NO: 44 resulting in a hybrid amylase as given in SEQ ID NO: 52 are the mutations I430M and M454I resulting in an amylase given as SEQ ID NO:53 or in SEQ ID NO:54 (numbering according to SEQ ID NO: 39). Thus, preferably, the amylase of the present invention comprises a substitution at one or more positions selected from the group consisting of 430 and 454, preferably, the amylase of the present invention comprises amino acid residues 430M and/or 430I, preferably the substitution resulting in 430M and/or 454I, preferably the substitution being selected from the group consisting of 1430M and M454I, according to the numbering of SEQ ID NO: 39.

The polypeptide having amylase activity of the present invention may further comprise a substitution at one or more positions selected from the group consisting of 9, 130, 195, 206, 244, 202, 179, 181, 186, and 190, preferably, at one or more positions selected from the group consisting of 9, 179, 186, 195, and 206, more preferably, one or more positions selected from the group consisting of 179, 195, and 206, according to the numbering of SEQ ID NO: 39, preferably one or more substitutions selected from the group consisting of M9L, E130V, N195F, I206L, S244Q, M202L, K179L, R181E, G186E/N/Q/S, and E190P, preferably, one or more substitutions selected from the group consisting of M9L, K179L, G186E/N/Q/S, N195F, and I206L, more preferably, one or more substitutions selected from the group consisting of K179L, G186E, N195F, and I206L, according to the numbering of SEQ ID NO: 39. In a further embodiment, the invention also relates to polynucleotides encoding the amylases of the present invention. In a further embodiment, the invention also relates to polypeptides which are encoded by a polynucleotide that hybridizes high stringency conditions with (i) the mature polypeptide coding sequence as described herein or (ii) the full-length complement of (i). The term "hybridisation" as defined herein is a process wherein substantially complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, sepharose beads or any other resin. The hybridisation process can furthermore occur with one of the complementary nucleic acids immobilised to a solid support such as a nitro-cellulose or nylon membrane or immobilised by e.g. photolithography to a carrier, including, but not limited to a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

This formation or melting of hybrids is dependent on various parameters, including but not limited thereto the temperature. An increase in temperature favours melting, while a decrease in temperature favours hybridisation. However, this hybrid forming process is not following an applied change in temperature in a linear fashion: the hybridisation process is dynamic, and already formed nucleotide pairs are supporting the pairing of adjacent nucleotides as well. So, with good approximation, hybridisation is a yes-or-no process, and there is a temperature, which basically defines the border between hybridisation and no hybridisation. This temperature is the melting temperature (Tm). Tm is the temperature in degrees Celsius, at which 50% of all molecules of a given nucleotide sequence are hybridised into a double strand, and 50% are present as single strands.

The melting temperature (Tm) is dependent from the physical properties of the analysed nucleic acid sequence and hence can indicate the relationship between two distinct sequences. However, the melting temperature (Tm) is also influenced by various other parameters, which are not directly related with the sequences, and the applied conditions of the hybridization experiment must be taken into account. For example, an increase of salts (e.g. monovalent cations) is resulting in a higher Tm. Tm for a given hybridisation condition can be determined by doing a physical hybridisation experiment, but Tm can also be estimated in silico for a given pair of DNA sequences. In this embodiment, the equation of Meinkoth and Wahl (Anal. Biochem., 138:267-284, 1984) is used for stretches having a length of 50 or more bases: $Tm = 81.5°\ C. + 16.6\ (\log M) + 0.41\ (\%\ GC) - 0.61\ (\%\ form) - 500/L$.

M is the molarity of monovalent cations, % GC is the percentage of guanosine and cytosine nucleotides in the DNA stretch, % form is the percentage of formamide in the hybridisation solution, and L is the length of the hybrid in base pairs. The equation is for salt ranges of 0.01 to 0.4 M and % GC in ranges of 30% to 75%.

While above Tm is the temperature for a perfectly matched probe, Tm is reduced by about 1° C. for each 1% of mismatching (Bonner et al., *J. Mol. Biol.* 81: 123-135, 1973): Tm=[81.5° C.+16.6 (log M)+0.41 (% GC)−0.61 (% formamide)−500/L]−% non-identity.

This equation is useful for probes having 35 or more nucleotides and is widely referenced in scientific method literature (e.g. in: "Recombinant DNA Principles and Methodologies", James Greene, Chapter "Biochemistry of Nucleic acids", Paul S. Miller, page 55; 1998, CRC Press), in many patent applications (e.g. in: U.S. Pat. No. 7,026, 149), and also in data sheets of commercial companies (e.g. "Equations for Calculating Tm" from www.genomics.agi-lent.com).

Other formulas for Tm calculations, which are less preferred in this embodiment, might be only used for the indicated cases:

For DNA-RNA hybrids (Casey, J. and Davidson, N. (1977) Nucleic Acids Res., 4:1539):

$$Tm=79.8° C.+18.5(\log M)+0.58(\% \ GC)+11.8(\% \ GC*\% \ GC)-0.5(\% \ form)-820/L.$$

For RNA-RNA hybrids (Bodkin, D. K. and Knudson, D. L. (1985) J. Virol. Methods, 10: 45):

$$Tm=79.8° C.+18.5(\log M)+0.58(\% \ GC)+11.8(\% \ GC*\% \ GC)-0.35(\% \ form)-820/L.$$

For oligonucleotide probes of less than 20 bases (Wallace, R. B., et al. (1979) Nucleic Acid Res. 6: 3535): Tm=2×n (A+T)+4×n(G+C), with n being the number of respective bases in the probe forming a hybrid.

For oligonucleotide probes of 20-35 nucleotides, a modified Wallace calculation could be applied: Tm=22+1.46 n(A+T)+2.92 n(G+C), with n being the number of respective bases in the probe forming a hybrid.

For other oligonucleotides, the nearest-neighbour model for melting temperature calculation should be used, together with appropriate thermodynamic data:

$$Tm=(\Sigma(\Delta Hd)+\Delta Hi)/(\Sigma(\Delta Sd)+\Delta Si+\Delta Sself+R\times\ln(cT/b))+16.6 \ \log[Na+]-273.15$$

(Breslauer, K. J., Frank, R., Blöcker, H., Marky, L. A. 1986 Predicting DNA duplex stability from the base sequence. Proc. Natl Acad. Sci. USA 833746-3750; Alejandro Panjk-ovich, Francisco Melo, 2005. Comparison of different melt-ing temperature calculation methods for short DNA sequences. Bioinformatics, 21 (6): 711-722)

where:
Tm is the melting temperature in degrees Celsius;
Σ(ΔHd) and Σ(ΔSd) are sums of enthalpy and entropy (correspondingly), calculated over all internal nearest-neighbor doublets;
ΔSself is the entropic penalty for self-complementary sequences;
ΔHi and ΔSi are the sums of initiation enthalpies and entropies, respectively;
R is the gas constant (fixed at 1.987 cal/K-mol);
cT is the total strand concentration in molar units;
constant b adopts the value of 4 for non-self-complemen-tary sequences or equal to 1 for duplexes of self-complementary strands or for duplexes when one of the strands is in significant excess.
The thermodynamic calculations assume that the anneal-ing occurs in a buffered solution at pH near 7.0 and that a two-state transition occurs.

Thermodynamic values for the calculation can be obtained from Table 1 in (Alejandro Panjkovich, Francisco Melo, 2005. Comparison of different melting temperature calculation methods for short DNA sequences. Bioinformat-ics, 21 (6): 711-722), or from the original research papers (Breslauer, K. J., Frank, R., Blöcker, H., Marky, L. A. 1986 Predicting DNA duplex stability from the base sequence. Proc. Natl Acad. Sci. USA 833746-3750; SantaLucia, J., Jr, Allawi, H. T., Seneviratne, P. A. 1996 Improved nearest-neighbor parameters for predicting DNA duplex stability. Biochemistry 353555-3562; Sugimoto, N., Nakano, S., Yoneyama, M., Honda, K. 1996 Improved thermodynamic parameters and helix initiation factor to predict stability of DNA duplexes. Nucleic Acids Res. 244501-4505).

For an in silico estimation of Tm according to this embodiment, first a set of bioinformatic sequence align-ments between the two sequences are generated. Such alignments can be generated by various tools known to a person skilled in the art, like programs "Blast" (NCBI), "Water" (EMBOSS) or "Matcher" (EMBOSS), which are producing local alignments, or "Needle" (EMBOSS), which is producing global alignments. Those tools should be applied with their default parameter setting, but also with some parameter variations. For example, program "MATCHER" can be applied with various parameter for gapopen/gapextend (like 14/4; 14/2; 14/5; 14/8; 14/10; 20/2; 20/5; 20/8; 20/10; 30/2; 30/5; 30/8; 30/10; 40/2; 40/5; 40/8; 40/10; 10/2; 10/5; 10/8; 10/10; 8/2; 8/5; 8/8; 8/10; 6/2; 6/5; 6/8; 6/10) and program "WATER" can be applied with various parameter for gapopen/gapextend (like 10/0.5; 10/1; 10/2; 10/3; 10/4; 10/6; 15/1; 15/2; 15/3; 15/4; 15/6; 20/1; 20/2; 20/3; 20/4; 20/6; 30/1; 30/2; 30/3; 30/4; 30/6; 45/1; 45/2; 45/3; 45/4; 45/6; 60/1; 60/2; 60/3; 60/4; 60/6), and also these programs shall be applied by using both nucleotide sequences as given, but also with one of the sequences in its reverse complement form. For example, BlastN (NCBI) can be applied with an increased e-value cut-off (e.g. e+1 or even e+10) to also identify very short alignments, especially in data bases of small sizes.

Important is that local alignments are considered, since hybridisation may not necessarily occur over the complete length of the two sequences, but may be best at distinct regions, which then are determining the actual melting temperature. Therefore, from all created alignments, the alignment length, the alignment % GC content (in a more accurate manner, the % GC content of the bases which are matching within the alignment), and the alignment identity has to be determined. Then the predicted melting tempera-ture (Tm) for each alignment has to be calculated. The highest calculated Tm is used to predict the actual melting temperature.

The term "hybridisation over the complete sequence of the invention" as defined herein means that for sequences longer than 300 bases when the sequence of the invention is fragmented into pieces of about 300 to 500 bases length, every fragment must hybridise. For example, a DNA can be fragmented into pieces by using one or a combination of restriction enzymes. A bioinformatic in silico calculation of Tm is then performed by the same procedure as described above, just done for every fragment. The physical hybridi-sation of individual fragments can be analysed by sta8ndard Southern analysis, or comparable methods, which are known to a person skilled in the art.

The term "stringency" as defined herein is describing the ease by which hybrid formation between two nucleotide sequences can take place. Conditions of a "higher strin-gency" require more bases of one sequence to be paired with the other sequence (the melting temperature Tm is lowered in conditions of "higher stringency"), conditions of "lower stringency" allow some more bases to be unpaired. Hence the degree of relationship between two sequences can be estimated by the actual stringency conditions at which they are still able to form hybrids. An increase in stringency can be achieved by keeping the experimental hybridisation temperature constant and lowering the salts concentrations, or by keeping the salts constant and increasing the experimental hybridisation temperature, or a combination of these parameter. Also an increase of formamide will increase the stringency. The skilled artisan is aware of additional parameters which may be altered during hybridisation and which will either maintain or change the stringency conditions (Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

A typical hybridisation experiment is done by an initial hybridisation step, which is followed by one to several washing steps. The solutions used for these steps may contain additional components, which are preventing the degradation of the analyzed sequences and/or prevent unspecific background binding of the probe, like EDTA, SDS, fragmented sperm DNA or similar reagents, which are known to a person skilled in the art (Sambrook et al. (2001) Molecular Cloning: a laboratory manual, $3^{rd}$ Edition, Cold Spring Harbor Laboratory Press, CSH, New York or to Current Protocols in Molecular Biology, John Wiley & Sons, N.Y. (1989 and yearly updates).

A typical probe for a hybridisation experiment is generated by the random-primed-labelling method, which was initially developed by Feinberg and Vogelstein (Anal. Biochem., 132 (1), 6-13 (1983); Anal. Biochem., 137 (1), 266-7 (1984) and is based on the hybridisation of a mixture of all possible hexanucleotides to the DNA to be labelled. The labelled probe product will actually be a collection of fragments of variable length, typically ranging in sizes of 100-1000 nucleotides in length, with the highest fragment concentration typically around 200 to 400 bp. The actual size range of the probe fragments, which are finally used as probes for the hybridisation experiment, can also be influenced by the used labelling method parameter, subsequent purification of the generated probe (e.g. agarose gel), and the size of the used template DNA which is used for labelling (large templates can e.g. be restriction digested using a 4 bp cutter, e.g. HaeII, prior labeling).

For the present invention, the sequence described herein is analysed by a hybridisation experiment, in which the probe is generated from the other sequence, and this probe is generated by a standard random-primed-labelling method. For the present invention, the probe is consisting of a set of labelled oligonucleotides having sizes of about 200-400 nucleotides. A hybridisation between the sequence of this invention and the other sequence means, that hybridisation of the probe occurs over the complete sequence of this invention, as defined above. The hybridisation experiment is done by achieving the highest stringency by the stringency of the final wash step. The final wash step has stringency conditions comparable to the stringency conditions of at least Wash condition 1: 1.06×SSC, 0.1% SDS, 0% formamide at 50° C., in another embodiment of at least Wash condition 2: 1.06×SSC, 0.1% SDS, 0% formamide at 55° C., in another embodiment of at least Wash condition 3: 1.06× SSC, 0.1% SDS, 0% formamide at 60° C., in another embodiment of at least Wash condition 4: 1.06×SSC, 0.1%

SDS, 0% formamide at 65° C., in another embodiment of at least Wash condition 5: 0.52×SSC, 0.1% SDS, 0% formamide at 65° C., in another embodiment of at least Wash condition 6: 0.25×SSC, 0.1% SDS, 0% formamide at 65° C., in another embodiment of at least Wash condition 7: 0.12× SSC, 0.1% SDS, 0% formamide at 65° C., in another embodiment of at least Wash condition 8: 0.07×SSC, 0.1% SDS, 0% formamide at 65° C.

A "low stringent wash" has stringency conditions comparable to the stringency conditions of at least Wash condition 1, but not more stringent than Wash condition 3, wherein the wash conditions are as described above.

A "high stringent wash" has stringency conditions comparable to the stringency conditions of at least Wash condition 4, in another embodiment of at least Wash condition 5, in another embodiment of at least Wash condition 6, in another embodiment of at least Wash condition 7, in another embodiment of at least Wash condition 8, wherein the wash conditions are as described above. The amylase of the present invention displays improved properties. Preferably, the improved property is relative to the property of an amylase shown in SEQ ID NO: 39 and/or SEQ ID NO: 40. It is preferred that the wash performance is improved at 15° C. In one embodiment the property that is improved is detergent stability. In another embodiment the property that is improved is specific activity. In another embodiment the property that is improved is thermal stability. In another embodiment the property that is improved is pH-dependent stability. In another embodiment the property that is improved is oxidative stability. In another embodiment the property that is improved is the reduction of Ca2+ dependency. In yet another embodiment the property that is improved is wash performance at low temperature. In one embodiment of the invention the polypeptides have an improved wash performance at low temperatures, such as at 40° C. or below 40° C., or at or below 30° C., or at or below 25° C. or at or below 20° C. or at or below 15° C., or at or below 10° C. In a preferred embodiment, the property that is improved is thermal stability Preferred polypeptides having amylase activity (amylases):

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44.

Preferably, the polypeptide having alpha-amylase activity consists of an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises the sequence TQXDYLDHPDVIGWTREGDXXHXXSGLA XLMSDGPXGXKWMXVGKNNAGEXWXDITG NQTNTVTINXDGXGQFXVXXGSXSIYXQX (SEQ ID NO: 56), wherein X can be any amino acid.

Preferably, the present invention refers to an isolated, synthetic, or recombinant polypeptide having alpha-amylase activity comprising an A and B domain and a C domain wherein the amino acid sequence of the A and B domain is at least at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises the sequence (SEQ ID NO: 56) TQXDYLDHPDVIGWTREGDXX HXXSGLAXLMSDGPXGXKWMXVGKN-NAGEXWXDITG NQTNTVTINXDGXGQFXVXXGSXSIYXQX, wherein X can be any amino acid.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity has one or more amino acid residues selected from the group consisting of 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K, preferably selected from the group consisting of 402R; 419D; 420V; 422A; 423D; 428A, T; 435R; 437S; 441E; 444K; 450V; 452Y; 466K; 469W; 473R; 475S; 476G; 479V; 483V; and 485Q according to the numbering of SEQ ID NO: 39, also preferred, selected from the group consisting of 435R, 437A, 441D, and 485K, according to the numbering of SEQ ID NO: 39.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all amino acid residues selected from the group consisting of 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K according to the numbering of SEQ ID NO: 39, preferably selected from the group consisting of 402R; 419D; 420V; 422A; 423D; 428A, T; 435R; 437S; 441E; 444K; 450V; 452Y; 466K; 469W; 473R; 475S; 476G; 479V; 483V; and 485Q according to the numbering of SEQ ID NO: 39.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises a substitution at one or more positions selected from the group consisting of 430 and 454, preferably the amylase comprises amino acid residues 430M and/or 430I, preferably the substitution is selected from the group consisting of I430M and M454I, preferably I430M and M454I, according to the numbering of SEQ ID NO: 39.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises a substitution at one or more positions selected from the group consisting of 430 and 454, preferably the amylase comprises amino acid residues 430M and/or 430I, preferably the substitution selected from the group consisting of I430M and M454I, preferably I430M and M454I, according to the numbering of SEQ ID NO: 39, wherein the polypeptide having alpha-amylase comprises a deletion of one or more amino acids corresponding to positions 181, 182, 183 and 184 corresponding to the numbering of SEQ ID NO: 39, preferably a deletion of two or more amino acids corresponding to positions 181, 182, 183 and 184, preferably a deletion of amino acids corresponding to positions 181 and 182, 182 and 183, or 183 and 184 (according to the numbering of SEQ ID NO: 39).

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises a substitution at one or more positions selected from the group consisting of 430 and 454, preferably the substitution selected from the group consisting of I430M and M454I, preferably I430M and M454I, according to the numbering of SEQ ID NO: 39, wherein the polypeptide having alpha-amylase comprises a deletion of one or more amino acids corresponding to positions 181, 182, 183 and 184 corresponding to the numbering of SEQ ID NO: 39, preferably a deletion of two or more amino acids corresponding to positions 181, 182, 183 and 184, preferably a deletion of amino acids corresponding to positions 181 and 182, 182 and 183, or 183 and 184 (according to the numbering of SEQ ID NO: 39) and wherein the isolated, synthetic, or recombinant polypeptide having alpha-amylase activity comprises the sequence TQXDYLDHPDVIGWTREGDXXHXXSGLAXL MSDGPXGXKWMXVGKNNAGEXWXDITG NQTNTVTINXDGXGQFXVXXGSXSIYXQX (SEQ ID NO: 56), wherein X can be any amino acid, preferably, wherein the polypeptide has one or more amino acid residues selected from the group consisting of 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K according to the numbering of SEQ ID NO: 39, preferably selected from the group consisting of 402R; 419D; 420V; 422A; 423D; 428A, T; 435R; 437S; 441E; 444K; 450V; 452Y; 466K; 469W; 473R; 475S; 476G; 479V; 483V; and 485Q according to the numbering of SEQ ID NO: 39.

Preferably, the present invention refers to an isolated, synthetic, or recombinant polypeptide having alpha-amylase activity comprising an A and B domain and a C domain wherein the amino acid sequence of the A and B domain is at least 95%, at least, 96%, at least 97%, at least 98%, at least 99% or 100% identical to the amino acid sequence of SEQ ID NO: 42 and the amino acid sequence of the C domain is at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises a substitution at one or more positions selected from the group consisting of 430 and 454, preferably the amylase comprises amino acid residues 430M and/or 4301, preferably the substitution selected from the group consisting of I430M and M454I, preferably I430M and M454I, according to the numbering of SEQ ID NO: 39, wherein the polypeptide having alpha-amylase comprises a deletion of one or more amino acids corresponding to positions 181, 182, 183 and 184 corresponding to the numbering of SEQ ID NO: 39, preferably a deletion of two or more amino acids corresponding to positions 181, 182, 183 and 184, preferably a deletion of amino acids corresponding to positions 181 and 182, 182 and 183, or 183 and 184 (according to the numbering of SEQ ID NO: 39).

Preferably, the present invention refers to an isolated, synthetic, or recombinant polypeptide having alpha-amylase activity comprising at least 95%, at least, 96%, at least 97%, at least 98%, at least 99% or 100% identical to the amino acid sequence of SEQ ID NO: 52, wherein the isolated, synthetic, or recombinant polypeptide having alpha-amylase activity comprises a substitution at one or more positions selected from the group consisting of 430 and 454, preferably the amylase comprises amino acid residues 430M and/or 4301, preferably the substitution resulting in 430M and/or 4541, preferably the substitution being selected from the group consisting of 1430M and M454I, preferably I430M and M454I, according to the numbering of SEQ ID NO: 39, wherein the polypeptide having alpha-amylase comprises a deletion of one or more amino acids corresponding to positions 181, 182, 183 and 184 corresponding to the numbering of SEQ ID NO: 39, preferably a deletion of two or more amino acids corresponding to positions 181, 182, 183 and 184, preferably a deletion of amino acids corresponding to positions 181 and 182, 182 and 183, or 183 and 184 (according to the numbering of SEQ ID NO: 39).

Preferably, the present invention refers to an isolated, synthetic, or recombinant polypeptide having alpha-amylase activity comprising at least 95%, at least, 96%, at least 97%, at least 98%, at least 99% or 100% identical to the amino acid sequence of SEQ ID NO: 53, wherein the polypeptide having alpha-amylase comprises a deletion of one or more amino acids corresponding to positions 181, 182, 183 and 184 corresponding to the numbering of SEQ ID NO: 39, preferably a deletion of two or more amino acids corresponding to positions 181, 182, 183 and 184, preferably a deletion of amino acids corresponding to positions 181 and 182, 182 and 183, or 183 and 184 (according to the numbering of SEQ ID NO: 39).

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises an amino acid residue at one or more of the amino acid positions selected from the group consisting of 401, 403, 405, 411, 413, 415, 424, 426, 428, 430, 432, 454, 455, 477, 479 and 481 (according to the numbering of SEQ ID NO: 39) as present in SEQ ID NO: 39.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises an amino acid residue at at least 1, at least 2, at least 3, at least 4, at least 5, at least 6, at least 7, at least 8, at least 9, at least 10, at least 11, at least 12, or at least 13, or all amino acid residues of the amino acid positions selected from the group consisting of 401, 403, 405, 411, 413, 415, 424, 426, 428, 430, 432, 454, 455, 477, 479 and 481 (according to the numbering of SEQ ID NO: 39) as present in SEQ ID NO: 39.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises an amino acid residue at one or more of the amino acid positions selected from the group consisting of 309, 313, 347, 348, 350, 351, 354, 355, 358, 359, 388, 389, 392 and 396 (according to the numbering of SEQ ID NO: 39) as present in SEQ ID NO: 40.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises an amino acid residue at at least 1, at least 2, at least 3, at least 4, at least 5, at least 6, at least 7, at least 8, at least 9, at least 10, at least 11, at least 12, at least 13, or all amino acid residues of the amino acid positions selected from the group consisting of 309, 313, 347, 348, 350, 351, 354, 355, 358, 359, 388, 389, 392 and 396 (according to the numbering of SEQ ID NO: 39) as present in SEQ ID NO: 40.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises a deletion of one or more amino acids corresponding to positions 181, 182, 183 and 184 corresponding to the numbering of SEQ ID NO: 39, preferably a deletion of two or more amino acids corresponding to positions 181, 182, 183 and 184, preferably a deletion of amino acids corresponding to positions 181 and 182, 182 and 183, or 183 and 184, preferably a deletion of amino acids corresponding to positions 182 and 183.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises a substitution at one or more positions selected from the group consisting of 9, 130, 195, 206, 244, 202, 179, 181, 186, and 190, preferably, at one or more positions selected from the group consisting of 9, 179, 186, 195, and 206, more preferably, one or more positions selected from the group consisting of 179, 195, and 206, according to the numbering of SEQ ID NO: 39, preferably one or more substitutions selected from the group consisting of M9L, E130V, N195F, I206L, S244Q, M202L, K179L, R181E, G186E/N/Q/S, and E190P, preferably, one or more substitutions selected from the group consisting of M9L, K179L, G186E/N/Q/S, N195F, and I206L, more preferably, one or more substitutions selected from the group consisting of K179L, G186E, N195F, and I206L, according to the numbering of SEQ ID NO: 39. Also disclosed herein is an isolated, synthetic, or recombinant polypeptide having alpha-amylase activity comprising at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 39 or SEQ ID NO: 40, wherein the isolated, synthetic, or recombinant polypeptide having alpha-amylase activity comprises a substitution at one or more positions, preferably at at least 1, at least 2, at least 3, at least 4, at least 5, at least 6, at least 7, at least 8, at least 9, or all amino acid residue positions, selected from the group consisting of 9, 130, 195, 206, 244, 202, 179, 181, 186, and 190 according to the numbering of SEQ ID NO: 39, preferably one or more substitutions selected from the group consisting of M9L, E130V, N195F, I206L, S244Q, M202L, K179L, R181E, G186E/N/Q/S, and E190P according to the numbering of SEQ ID NO: 39.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises a substitution at at least 1, at least 2, at least 3, at least 4, at least 5, at least 6, at least 7, at least 8, at least 9, or all amino acid residue positions selected from the group consisting of 9, 130, 195, 206, 244, 202, 179, 181, 186, and 190 according to the numbering of SEQ ID NO: 39, preferably at least 1, at least 2, at least 3, at least 4, at least 5, at least 6, at least 7, at least 8, at least 9, or all amino acid substitutions selected from the group consisting of M9L, E130V, N195F, I206L, S244Q, M202L, K179L, R181E, G186E/N/Q/S, and E190P according to the numbering of SEQ ID NO: 39.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises an increase in expression, activity, thermostability, stability, performance in laundry, specific activity, substrate specificity, pH-dependent activity, pH-dependent stability, oxidative stability, Ca2+ dependency, or any combination thereof compared to the amylase shown in SEQ ID NO: 39 or SEQ ID NO: 40, preferably, the amylase has an increase in thermostability compared to the amylase shown in SEQ ID NO: 39 or SEQ ID NO: 40.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises an increase in thermostability compared to the amylase shown in SEQ ID NO: 39 or SEQ ID NO: 40.

In one embodiment, the present invention refers to an isolated, synthetic, or recombinant polypeptide having alpha-amylase activity comprises:

(a) an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, preferably, SEQ ID NO:54, SEQ ID NO:5, SEQ ID NO:11, SEQ ID NO:17, or SEQ ID NO:27;

(b) an amino acid sequence encoded by a polynucleotide having at least at least 80%, at least 85%, at least 90%, at least 91%, at least 92%, at least 93%, at least 94%, at least 95%, at least, 96%, at least 97%, at least 98%, at least 99% or 100% sequence identity with SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, preferably, SEQ ID NO:55, SEQ ID NO:6, SEQ ID NO:12, SEQ ID NO:18, or SEQ ID NO:29, (c) an amino acid sequence encoded by a polynucleotide that hybridizes under high stringency conditions with the complement of (i) a coding sequence of SEQ ID NO:54, SEQ 1D NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, preferably, SEQ ID NO:54, SEQ ID NO:5, SEQ ID NO:11, SEQ ID NO:17, or SEQ ID NO:27; or (ii) a polynucleotide shown in SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, preferably, SEQ ID NO:55, SEQ ID NO:6, SEQ ID NO:12, SEQ ID NO:18, or SEQ ID NO:29;

or (d) a fragment of (a), (b), or (c) having amylase activity.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises the sequence TQXDYLDHPDVIGWTREGDXXHXXSG LAXLMSDGPXGXKWMXVGKNNAGEXWXDITG NQTNTVTINXDGXGQFXVXXGSXSIYXQX (SEQ ID NO: 56), wherein X can be any amino acid.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, or at least 99% sequence identity to SEQ ID NO: 39, wherein the isolated, synthetic, or recombinant polypeptide having alpha-amylase activity comprises the sequence TQXDYLDHPDVIGWTREGDXXHXXSGLAXLMSDGP XGXKWMXVGKNNAGEXWXDITG NQTNTVTINXDGXGQFXVXXGSXSIYXQX (SEQ ID NO: 56), wherein X can be any amino acid, preferably, wherein the polypeptide has one or more amino acid residues selected from the group consisting of 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K according to the numbering of SEQ ID NO: 39, preferably selected from the group consisting of 402R; 419D; 420V; 422A; 423D; 428A, T; 435R; 437S; 441E; 444K; 450V; 452Y; 466K; 469W; 473R; 475S; 476G; 479V; 483V; and 485Q according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises the sequence TQXDYLDHPDVIGWTREGDXXHXXSGLAXLMS DGPXGXKWMXVGKNNAGEXWXDITG NQTNTVTINXDGXGQFXVXXGSXSIYXQX (SEQ ID NO: 56), wherein X can be any amino acid.

Preferably, the amylase of the present invention comprises at least one amino acid substitution as described herein and comprises an amino acid sequence that is at least 80%, at least 85%, at least 90%, at least 95%, at least 96%, at least 97%, at least 97.5%, at least 98%, at least 98.5%, at least 99%, or at least 99.5% identical to the amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, preferably, SEQ ID NO:54, SEQ ID NO:5, SEQ ID NO:11, SEQ ID NO:17, or SEQ ID NO:27.

Preferably, the amylase of the present invention comprises at least one amino acid substitution as described herein and comprises an amino acid sequence that is at least 80%, at least 85%, at least 90%, at least 95%, at least 96%, at least 97%, at least 97.5%, at least 98%, at least 98.5%, at least 99%, or at least 99.5% identical to the amino acid sequence of: SEQ ID NO:54, preferably at least 95%, at least 96%, at least 97%, at least 97.5%, at least 98%, at least 98.5%, at least 99%, or at least 99.5% identical to the amino acid sequence of: SEQ ID NO:54.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity has one or more amino acid residues selected from the group consisting of 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K, preferably, selected from the group consisting of 435R, 437A, 441D, and 485K, according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:39, wherein the isolated, synthetic, or recombinant polypeptide having alpha-amylase activity has one or more amino acid residues selected from the group consisting of 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K, according to the numbering of SEQ ID NO: 39, preferably selected from the group consisting of 402R; 419D; 420V; 422A; 423D; 428A, T; 435R; 437S; 441E; 444K; 450V; 452Y; 466K; 469W; 473R; 475S; 476G; 479V; 483V; and 485Q according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity has one or more amino acid residues selected from the group consisting of 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K, preferably selected from the group consisting of 402R; 419D; 420V; 422A; 423D; 428A, T; 435R; 437S; 441E; 444K; 450V; 452Y; 466K; 469W; 473R; 475S; 476G; 479V; 483V; and 485Q according to the numbering of SEQ ID NO: 39, preferably, selected from the group consisting of 435R, 437S, A, 441E, D, and 485Q, K, according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity has at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all amino acid residues selected from the group consisting of 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K according to the numbering of SEQ ID NO: 39, preferably selected from the group consisting of 402R; 419D; 420V; 422A; 423D; 428A, T; 435R; 437S; 441E; 444K; 450V; 452Y; 466K; 469W;

473R; 475S; 476G; 479V; 483V; and 485Q according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity has amino acid residues 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K according to the numbering of SEQ ID NO: 39, preferably selected from the group consisting of 402R; 419D; 420V; 422A; 423D; 428A, T; 435R; 437S; 441E; 444K; 450V; 452Y; 466K; 469W; 473R; 475S; 476G; 479V; 483V; and 485Q according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises a substitution at one or more positions selected from the group consisting of 430 and 454, preferably the amylase comprises amino acid residues 430M and/or 430I, preferably the substitution resulting in 430M and/or 454I, preferably the substitution being selected from the group consisting of I430M and M454I, according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises a substitution at one or more positions selected from the group consisting of 430 and 454, preferably the amylase comprises amino acid residues 430M and/or 430I, preferably the substitution resulting in 430M and/or 454I, preferably the substitution being selected from the group consisting of I430M and M454I, according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises a substitution at position 430 and 454, preferably the substitution resulting in 430M and/or 454I, preferably the substitution being selected from the group consisting of I430M and M454I, according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises a substitution at position 430 and 454, preferably the substitution resulting in 430M and/or 454I, preferably the substitution being selected from the group consisting of I430M and M454I, according to the numbering of SEQ ID NO: 39, wherein the polypeptide having alpha-amylase activity comprises a deletion of one or more amino acids corresponding to positions 181, 182, 183 and 184 corresponding to the numbering of SEQ ID NO: 39, preferably a deletion of two or more amino acids corresponding to positions 181, 182, 183 and 184, preferably a deletion of amino acids corresponding to positions 181 and 182, 182 and 183, or 183 and 184 (according to the numbering of SEQ ID NO: 39).

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises an amino acid residue at one or more of the amino acid positions selected from the group consisting of 401, 403, 405, 411, 413, 415, 424, 426, 428, 430, 432, 454, 455, 477, 479 and 481 (according to the numbering of SEQ ID NO: 39) as present in SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises an amino acid residue at one or more of the amino acid positions selected from the group consisting of 401, 403, 405, 411, 413, 415, 424, 426, 428, 430, 432, 454, 455, 477, 479 and 481 (according to the numbering of SEQ ID NO: 39) as present in SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises an amino acid residue at at least 1, at least 2, at least 3, at least 4, at least 5, at least 6, at least 7, at least 8, at least 9, at least 10, at least 11, at least 12, or at least 13, or all amino acid residues of the amino acid positions selected from the group consisting of 401, 403, 405, 411, 413, 415, 424, 426, 428, 430, 432, 454, 455, 477, 479 and 481 (according to the numbering of SEQ ID NO: 39) as present in SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises an amino acid residue at at least 1, at least 2, at least 3, at least 4, at least 5, at least 6, at least 7, at least 8, at least 9, at least 10, at least 11, at least 12, or at least 13, or all amino acid residues of the amino acid positions selected from the group consisting of 401, 403, 405, 411, 413, 415, 424, 426, 428, 430, 432, 454, 455, 477, 479 and 481 (according to the numbering of SEQ ID NO: 39) as present in SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises an amino acid residue at one or more of the amino acid positions selected from the group consisting of 309, 313, 347, 348, 350, 351, 354, 355, 358, 359, 388, 389, 392 and 396 (according to the numbering of SEQ ID NO: 39) as present in SEQ ID NO: 40.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises an amino acid residue at one or more of the amino acid positions selected from the group consisting of 309, 313, 347, 348, 350, 351, 354, 355, 358, 359, 388, 389, 392 and 396 (according to the numbering of SEQ ID NO: 39) as present in SEQ ID NO: 40.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises an amino acid residue at least 1, at least 2, at least 3, at least 4, at least 5, at least 6, at least 7, at least 8, at least 9, at least 10, at least 11, at least 12, at least 13, or all amino acid residues of the amino acid positions selected from the group consisting of 309, 313, 347, 348, 350, 351, 354, 355, 358, 359, 388, 389, 392 and 396 (according to the numbering of SEQ ID NO: 39) as present in SEQ ID NO: 40.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises a deletion of one or more amino acids corresponding to positions 181, 182, 183 and 184 corresponding to the numbering of SEQ ID NO: 39, preferably a deletion of two or more amino acids corresponding to positions 181, 182, 183 and 184, preferably a deletion of amino acids corresponding to positions 181 and 182, 182 and 183, or 183 and 184 (according to the numbering of SEQ ID NO: 39).

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises a deletion of one or more amino acids corresponding to positions 182 and 183, preferably a deletion of both amino acids corresponding to positions 182 and 183 (according to the numbering of SEQ ID NO: 39).

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises a deletion of one or more amino acids corresponding to positions 181, 182, 183 and 184 corresponding to the numbering of SEQ ID NO: 39, preferably a deletion of two or more amino acids corresponding to positions 181, 182, 183 and 184, preferably a deletion of amino acids corresponding to positions 181 and 182, 182 and 183, or 183 and 184 (according to the numbering of SEQ ID NO: 39).

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises a deletion of one or more amino acids corresponding to positions 182 and 183, preferably a deletion of both amino acids corresponding to positions 182 and 183 (according to the numbering of SEQ ID NO: 39).

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises a deletion of both amino acids corresponding to positions 182 and 183 (according to the numbering of SEQ ID NO: 39).

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises a substitution at one or more positions selected from the group consisting of 9, 130, 195, 206, 244, 202, 179, 181, 186, and 190 according to the numbering of SEQ ID NO: 39, preferably one or more substitutions selected from the group consisting of M9L, E130V, N195F, I206L, S244Q, M202L, K179L, R181E, G186E/N/Q/S, and E190P according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises a substitution at one or more positions selected from the group consisting of 9, 130, 195, 206, 244, 202, 179, 181, 186, and 190, preferably, at one or more positions selected from the group consisting of 9, 179, 186, 195, and 206, more preferably, one or more positions selected from the group consisting of 179, 195, and 206, according to the numbering of SEQ ID NO: 39, preferably one or more substitutions selected from the group consisting of M9L, E130V, N195F, I206L, S244Q, M202L, K179L, R181E, G186E/N/Q/S, and E190P, preferably, one or more substitutions selected from the group consisting of M9L, K179L, G186E/N/Q/S, N195F, and I206L, more preferably, one or more substitutions selected from the group consisting of K179L, G186E, N195F, and I206L, according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises a substitution at at least 1, at least 2, at least 3, at least 4, at least 5, at least 6, at least 7, at least 8, at least 9, or all amino acid residue positions selected from the group consisting of 9, 130, 195, 206, 244, 202, 179, 181, 186, and 190 according to the numbering of SEQ ID NO: 39, preferably at least 1, at least 2, at least 3, at least 4, at least 5, at least 6, at least 7, at least 8, at least 9, at least 10, or all amino acid substitutions selected from the group consisting of M9L, E130V, N195F, I206L, S244Q, M202L, K179L, R181E, G186E/N/Q/S, and E190P according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises a substitution at at least 1, at least 2, at least 3, at least 4, at least 5, at least 6, at least 7, at least 8, at least 9, at least 10, at least 11, at least 12, at least 13, or all amino acid residue positions selected from the group consisting of 9, 130, 195, 206, 244, 202, 179, 181, 186, and 190 according to the numbering of SEQ ID NO: 39, preferably at least 1, at least 2, at least 3, at least 4, at least 5, at least 6, at least 7, at least 8, at least 9, at least 10, at least 11, at least 12, at least 13, or all amino acid substitutions selected from the group consisting of M9L, E130V, N195F, I206L, S244Q, M202L, K179L, R181E, G186E/N/Q/S, and E190P according to the numbering of SEQ ID NO: 39.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the isolated, synthetic, or recombinant polypeptide having alpha-amylase activity comprises an increase in expression, activity, thermostability, stability, performance in laundry, specific activity, substrate specificity, pH-dependent activity, pH-dependent stability, oxidative stability, Ca2+ dependency, or any combination thereof compared to the amylase shown in SEQ ID NO: 39 or SEQ ID NO: 40, preferably, the amylase has an increase in thermostability compared to the amylase shown in SEQ ID NO: 39 or SEQ ID NO: 40.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises an increase in expression, activity, thermostability, stability, performance in laundry, specific activity, substrate specificity, pH-dependent activity, pH-dependent stability, oxidative stability, Ca2+ dependency, or any combination thereof compared to the amylase shown in SEQ ID NO: 39 or SEQ ID NO: 40, preferably, the amylase has an increase in thermostability compared to the amylase shown in SEQ ID NO: 39 or SEQ ID NO: 40.

Preferably, the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the isolated, synthetic, or recombinant polypeptide having alpha-amylase activity comprises an increase in thermostability compared to the amylase shown in SEQ ID NO: 39 or SEQ ID NO: 40.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37.

Preferably, the present invention refers to an isolated, synthetic, or recombinant polypeptide having alpha-amylase activity comprising an A and B domain and a C domain wherein the amino acid sequence of the A and B domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 42 and the amino acid sequence of the C domain is at least 75%, at least 80%, at least 85%, at least 90%, at least 91%, at least 92%, at least 93%, at least 94%, at least 95%, at least, 96%, at least 97%, at least 98%, at least 99% or 100% identical to the amino acid sequence of SEQ ID NO: 44, wherein the isolated, synthetic, or recombinant polypeptide having alpha-amylase activity comprises an amino acid sequence having at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54.

The present invention also refers to an isolated, a synthetic, or a recombinant nucleic acid comprising:

(a) a nucleic acid sequence having at least at least 80%, at least 85%, at least 90%, at least 91%, at least 92%, at least 93%, at least 94%, at least 95%, at least, 96%, at least 97%, at least 98%, at least 99%, or 100% sequence identity to SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, wherein the nucleic acid encodes a polypeptide having amylase activity;

(b) a nucleic acid sequence encoding a polypeptide having at least at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the polypeptide has amylase activity or any polypeptide described herein having amylase activity, preferably a polypeptide having alpha-amylase activity comprising an A and B domain and a C domain wherein the amino acid sequence of the A and B domain is at least 75% identical to the amino acid sequence of SEQ ID NO: 42 and the amino acid sequence of the C domain is at least 75% identical to the amino acid sequence of SEQ ID NO: 44;

(c) a polynucleotide that hybridizes under high stringency conditions with the complement of (i) a coding sequence of SEQ ID NO:54, SEQ 1D NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37; or (ii) a polynucleotide shown in SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38;

(d) a fragment of (a), (b), or (c), wherein the fragment encodes a polypeptide having amylase activity; or (e) a nucleic acid sequence fully complementary to any of (a) to (d).

Preferably, the isolated, a synthetic, or a recombinant nucleic acid comprises:

(a) a nucleic acid sequence having at least at least 80%, at least 85%, at least 90%, at least 91%, at least 92%, at least 93%, at least 94%, at least 95%, at least, 96%, at least 97%, at least 98%, at least 99%, or 100% sequence identity to SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, wherein the nucleic acid encodes a polypeptide having amylase activity;

(b) a nucleic acid sequence encoding a polypeptide having at least at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the polypeptide has amylase activity;

(c) a fragment of (a), or (b), wherein the fragment encodes a polypeptide having amylase activity; or (d) a nucleic acid sequence fully complementary to any of (a) to (d).

Further preferred herein is an isolated, a synthetic, or a recombinant nucleic acid comprising (a) a nucleic acid sequence having at least 80% sequence identity to SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, wherein the nucleic acid encodes a polypeptide having amylase activity;

(b) a nucleic acid sequence encoding a polypeptide having at least 90% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the polypeptide has amylase activity;

(c) a fragment of (a) or (b), wherein the fragment encodes a polypeptide having amylase activity; or (d) a nucleic acid sequence fully complementary to any of (a) to (c).

Further preferred herein is an isolated, a synthetic, or a recombinant nucleic acid comprising (a) a nucleic acid sequence having at least 90% sequence identity to SEQ ID NO:55, wherein the nucleic acid encodes a polypeptide having amylase activity;

(b) a nucleic acid sequence encoding a polypeptide having at least 80% sequence identity to SEQ ID NO:54, wherein the polypeptide has amylase activity;

(c) a fragment of (a) or (b), wherein the fragment encodes a polypeptide having amylase activity; or (d) a nucleic acid sequence fully complementary to any of (a) to (c).

Preferably, the isolated, a synthetic, or a recombinant nucleic acid comprises:

(a) a nucleic acid sequence having at least at least 80%, at least 85%, at least 90%, at least 91%, at least 92%, at least 93%, at least 94%, at least 95%, at least, 96%, at least 97%, at least 98%, at least 99%, or 100% sequence identity to SEQ ID NO:55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, wherein the nucleic acid encodes a polypeptide having amylase activity;

(b) a nucleic acid sequence encoding a polypeptide having at least at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the polypeptide has amylase activity.

Preferably, the isolated, a synthetic, or a recombinant nucleic acid comprises:

(a) a nucleic acid sequence having at least at least 80%, at least 85%, at least 90%, at least 91%, at least 92%, at least 93%, at least 94%, at least 95%, at least, 96%, at least 97%, at least 98%, at least 99%, or 100% sequence identity to SEQ ID NO:55, wherein the nucleic acid encodes a polypeptide having amylase activity;

(b) a nucleic acid sequence encoding a polypeptide having at least at least 80%, at least 85%, at least 90%, at least 91%, at least 92%, at least 93%, at least 94%, at least 95%, at least, 96%, at least 97%, at least 98%, at least 99% or 100% sequence identity to SEQ ID NO:54, wherein the polypeptide has amylase activity.

Further preferred herein is an amylase comprising an amino acid sequence that is at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37.

Further preferred herein is a polypeptide having amylase activity (i.e., an amylase) comprising an amino acid sequence that is at least 94%, at least 95%, at least 96%, at least 97%, at least 98%, at least 98.5%, at least 99%, at least 99.5%, or 100% identical to the full-length amino acid sequence of: SEQ ID NO:54.

Further preferred herein is an amylase comprising an amino acid sequence that is at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37.

Further preferred herein is an amylase comprising an amino acid sequence that is at least 99% or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37.

Further preferred herein is an amylase comprising an amino acid sequence that is 99.5% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37.

Further preferred herein is an amylase comprising an amino acid sequence that is 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37.

Further preferred herein is an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO: 52, SEQ ID NO: 53, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37.

Further preferred herein is an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54.

Further preferred herein is an amylase comprising an amino acid sequence that is at least 95%, at least 96%, at least 97%, at least 98%, at least 98.5%, at least 99%, at least 99.5%, or 100% identical to the full-length amino acid sequence of: SEQ ID NO:54.

Further preferred herein is an amylase comprising one or more amino acid residue insertions, deletions, substitutions, or any combinations thereof to the amino acid sequence of: SEQ ID NO:54, SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37.

Further preferred herein is an amylase comprising one or more amino acid residue substitution to the amino acid sequence of: SEQ ID NO:54, SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, preferably SEQ ID NO:54, preferably at 1, 2, 3, 4, 5, 6, 7, 8, 9, 10, 11, 12, 13, 14, 15, 16, 17, 18, 19, 20, 21, 22, 23, 24, or 25 positions, preferably, at 1-25 positions, more preferably, at 1-10 positions.

Further preferred herein is an amylase wherein the amino acid sequence is encoded by a polynucleotide having a nucleic acid sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full length polynucleotide sequence of SEQ ID NO: 55, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38.

Further preferred herein is an amylase wherein the amino acid sequence is encoded by a polynucleotide having a nucleic acid sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full length polynucleotide sequence of SEQ ID NO:55.

Further preferred herein is an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the amylase has an increase in expression; activity; thermostability; stability; performance in laundry; and any combination thereof.

Further preferred herein is an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the amylase has an increase in thermostability.

Further preferred herein is an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, wherein the amylase has an increase in thermostability.

Further preferred herein is an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, wherein the increase in thermostability is after a heat challenge at a temperature from 70 degrees C. to 100 degrees C., preferably, wherein the increase in thermostability is after a heat challenge at a temperature from 70 degrees C. to 90 degrees C., more preferably, between 75 degrees C. to 85 degrees C., most preferably at 80 degrees C.

Further preferred herein is an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, wherein the increase in thermostability is after a heat challenge at a temperature from 70 degrees C. to 100 degrees C., preferably, wherein the increase in thermostability is after a heat challenge at a temperature from 70 degrees C. to 90 degrees C., more preferably, between 75 degrees C. to 85 degrees C., most preferably at 80 degrees C.

Further preferred herein is an amylase comprising an amino acid sequence that is at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, wherein amylase comprises an increase in thermostability after a heat challenge at 80 degrees C.

In another aspect the present invention refers to a composition comprising the polypeptide described herein. A composition may comprise combinations of the polypeptides with another enzyme. The combination of enzymes can be of the same class, for example a composition comprising a first amylase and a second amylase. Combinations of enzymes can be from a different class of enzymes, for example, a composition comprising a lipase and an amylase. Combinations of enzymes can be compositions comprising at least one amylase of the invention and one or more second enzymes. In one embodiment, the composition comprises one second enzyme, two second enzymes, three second enzymes, four second enzymes, or more than four second enzymes. In an embodiment, the second enzyme is selected from the group consisting of: a second amylase, a lipase, a protease, a cellulase, a laccase, a pectinase, and a nuclease, or any combination thereof.

A compositions comprising an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37. In another embodiment, the composition further comprises a second enzyme selected from the group consisting of: a second amylase, a lipase, a protease, a cellulase, a laccase, a mannanase, a pectinase, xylanase, a nuclease, and any combination thereof. In preferred embodiment, the composition further comprises a second enzyme and the second enzyme is a different amylase. In another preferred embodiment, the composition further comprises a second enzyme and the second enzyme is a protease.

Preferably, a compositions comprising an amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54. In another embodiment, the composition further comprises a second enzyme selected from the group consisting of: a second amylase, a lipase, a protease, a cellulase, a laccase, a mannanase, a pectinase, xylanase, a nuclease, and any combination thereof. In preferred embodiment, the composition further comprises a second enzyme and the second enzyme is a different amylase. In another preferred embodiment, the composition further comprises a second enzyme and the second enzyme is a protease.

Additional enzymes suitable for the hybrid or the composition of the present invention are further described below. In one embodiment, suitable enzymes include enzyme variants having enzymatic activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical when compared to the full length polypeptide sequence of the parent enzyme as disclosed below.

Amylase

Alpha-amylase (E.C. 3.2.1.1) enzymes may perform endohydrolysis of (1→4)-alpha-D-glucosidic linkages in polysaccharides containing three or more (1→4)-alpha-linked D-glucose units.

Amylase enzymes act on starch, glycogen and related polysaccharides and oligosaccharides in a random manner; reducing groups are liberated in the alpha-configuration. Other examples of amylase enzymes include: Beta-amylase (E.C. 3.2.1.2), Glucan 1,4-alpha-maltotetraohydrolase (E.C. 3.2.1.60), Isoamylase (E.C. 3.2.1.68), Glucan 1,4-alpha-maltohexaosidase (E.C. 3.2.1.98), and Glucan 1,4-alpha-maltohydrolase (E.C. 3.2.1.133).

The amylases described below can be used as a parent amylase to create variant amylases by introducing one or more amino acid substitutions and/or deletions as described herein.

Many amylase enzymes have been described in patents and published patent applications including, but not limited to: WO 2002/068589, WO 2002/068597, WO 2003/083054, WO 2004/091544, and WO 2008/080093.

Amylases are known to be derived from *Bacillus licheniformis* having SEQ ID NO:2 as described in WO 95/10603. Suitable variants are those which are at least 90% identical to SEQ ID NO: 2 as described in WO 95/10603 and/or comprising one or more substitutions in the following positions: 15, 23, 105, 106, 124, 128, 133, 154, 156, 178, 179, 181, 188, 190, 197, 201, 202, 207, 208, 209, 211, 243, 264, 304, 305, 391, 408, and 444 which have amylolytic activity. Such variants are described in WO 94/02597, WO 94/018314, WO 97/043424 and SEQ ID NO:4 of WO 99/019467.

Amylases are known to be derived from *B. stearothermophilus* having SEQ ID NO:6 as described in WO 02/10355 or an amylase which is at least 90% identical thereto having amylolytic activity with optionally having a C-terminal truncation over the wildtype sequence. Suitable variants of SEQ ID NO:6 include those which is at least 90% identical thereto and/or further comprise a deletion in positions 181 and/or 182 and/or a substitution in position 193.

Amylases are known to be derived from *Bacillus* sp.707 having SEQ ID NO:6 as disclosed in WO 99/19467 or an amylase which is at least 90% identical thereto having amylolytic activity.

Amylases are known from *Bacillus halmapalus* having SEQ ID NO:2 or SEQ ID NO:7 as described in WO 96/23872, also described as SP-722, or an amylase which is at least 90% identical to one of the sequences which has amylolytic activity.

Amylases are known to be derived from *Bacillus* sp. DSM 12649 having SEQ ID NO:4 as disclosed in WO 00/22103 or an amylase which is at least 90% identical thereto having amylolytic activity.

Amylases are known from *Bacillus* strain TS-23 having SEQ ID NO:2 as disclosed in WO 2009/061380 or an amylase which is at least 90% identical thereto having amylolytic activity.

Amylases are known from *Cytophaga* sp. having SEQ ID NO:1 as disclosed in WO 2013/184577 or an amylase which is at least 90% identical thereto having amylolytic activity.

Amylases are known from *Bacillus megaterium* DSM 90 having SEQ ID NO:1 as disclosed in WO 2010/104675 or an amylase which is at least 90% identical thereto having amylolytic activity.

Amylases are known having amino acids 1 to 485 of SEQ ID NO:2 as described in WO 00/60060 or amylases comprising an amino acid sequence which is at least 96% identical with amino acids 1 to 485 of SEQ ID NO:2 which have amylolytic activity.

Amylases are also known having SEQ ID NO: 12 as described in WO 2006/002643 or amylases having at least 80% identity thereto and have amylolytic activity. Suitable amylases include those having at least 80% identity compared to SEQ ID NO:12 and/or comprising the substitutions at positions Y295F and M202LITV and have amylolytic activity.

Amylases are also known having SEQ ID NO:6 as described in WO 2011/098531 or amylases having at least 80% identity thereto having amylolytic activity. Suitable amylases include those having at least 80% identity compared to SEQ ID NO:6 and/or comprising a substitution at one or more positions selected from the group consisting of 193 [G, A, S, T or M], 195 [F, W, Y, L, I or V], 197 [F, W, Y, L, I or V], 198 [Q or N], 200 [F, W, Y, L, I or V], 203 [F, W, Y, L, I or V], 206 [F, W, Y, N, L, I, V, H, Q, D or E], 210 [F, W, Y, L, I or V], 212 [F, W, Y, L, I or V], 213 [G, A, S, T or M] and 243 [F, W, Y, L, I or V] and have amylolytic activity.

Amylases are known having SEQ ID NO:1 as described in WO 2013/001078 or amylases having at least 85% identity thereto having amylolytic activity. Suitable amylases include those having at least 85% identity compared to SEQ ID NO:1 and/or comprising an alteration at two or more (several) positions corresponding to positions G304, W140, W189, D134, E260, F262, W284, W347, W439, W469, G476, and G477 and having amylolytic activity.

Amylases are known having SEQ ID NO:2 as described in WO 2013/001087 or amylases having at least 85% identity thereto and having amylolytic activity. Suitable amylases include those having at least 85% identity compared to SEQ ID NO:2 and/or comprising a deletion of positions 181+182, or 182+183, or 183+184 according to the numbering of SEQ ID NO: 2 as described in WO 2013/001087, which have amylolytic activity. Suitable amylases include those having at least 85% identity compared to SEQ ID NO:2 and/or comprising a deletion of positions 181+182, or 182+183, or 183+184 according to the numbering of SEQ ID NO: 2 as described in WO 2013/001087, which comprise one or two or more modifications in any of positions corresponding to W140, W159, W167, Q169, W189, E194, N260, F262, W284, F289, G304, G305, R320, W347, W439, W469, G476 and G477 and have amylolytic activity. Amylases also include hybrid α-amylase from above mentioned amylases as for example as described in WO 2006/066594.

Commercially available amylase enzymes include: DURAMYL™, TERMAMYL™ TERMAMYL SC™, TERMAMYL Ultra™, FUNGAMYL™, STAINZYME™, STAINZYME Plus™, NATALASE™, LIQUOZYME X, SUPRAMYL™ AMPLIFY™, AMPLIFY Prime™ and BAN™ (from Novozymes A/S), and RAPIDASE™, PURASTAR™, PURASTAR OxAm™ POWERASE™, EFFECTENZ™ (M100 from DuPont), PREFERENZ™ (S1000, S110 and F1000; from DuPont), PRIMAGREEN™ (ALL; DuPont), OPTISIZE™ (DuPont) and KAM™ (Kao) and KEMZYME™ (Biozym).

Lipase

Lipase

"Lipases", "lipolytic enzyme", "lipid esterase", all refer to an enzyme of EC class 3.1.1 ("carboxylic ester hydrolase"). Lipases (E.C. 3.1.1.3, Triacylglycerol lipase) may hydrolyze triglycerides to more hydrophilic mono- and diglycerides, free fatty acids, and glycerol. Lipase enzymes usually includes also enzymes which are active on substrates different from triglycerides or cleave specific fatty acids, such as Phospholipase A (E.C. 3.1.1.4), Galactolipase (E.C. 3.1.1.26), cutinase (EC 3.1.1.74), and enzymes having sterol esterase activity (EC 3.1.1.13) and/or wax-ester hydrolase activity (EC 3.1.1.50).

Many lipase enzymes have been described in patents and published patent applications including, but not limited to: WO2000032758, WO2003/089620, WO2005/032496, WO2005/086900, WO200600976, WO2006/031699, WO2008/036863, WO2011/046812, and WO2014059360.

Lipases are used in detergent and cleaning products to remove grease, fat, oil, and dairy stains. Commercially available lipases include but are not limited to: LIPO-LASE™, LIPEX™, LIPOLEX™ and LIPOCLEAN™ (Novozymes A/S), LUMAFAST (originally from Genencor) and LIPOMAX (Gist-Brocades/now DSM).

The methods for determining lipolytic activity are well-known in the literature (see e.g. Gupta et al. (2003), Biotechnol. Appl. Biochem. 37, p. 63-71). E.g. the lipase activity may be measured by ester bond hydrolysis in the substrate para-nitrophenyl palmitate (pNP-Palmitate, C:16) and releases pNP which is yellow and can be detected at 405 nm.

Protease

Enzymes having proteolytic activity are called "proteases" or "peptidases". Proteases are active proteins exerting "protease activity" or "proteolytic activity".

Proteases are members of class EC 3.4. Proteases include aminopeptidases (EC 3.4.11), dipeptidases (EC 3.4.13), dipeptidyl-peptidases and tripeptidyl-peptidases (EC 3.4.14), peptidyl-dipeptidases (EC 3.4.15), serine-type carboxypeptidases (EC 3.4.16), metallocarboxypeptidases (EC 3.4.17), cysteine-type carboxypeptidases (EC 3.4.18), omega peptidases (EC 3.4.19), serine endopeptidases (EC 3.4.21), cysteine endopeptidases (EC 3.4.22), aspartic endopeptidases (EC 3.4.23), metallo-endopeptidases (EC 3.4.24), threonine endopeptidases (EC 3.4.25), endopeptidases of unknown catalytic mechanism (EC 3.4.99).

Commercially available protease enzymes include but are not limited to LAVERGY™ Pro (BASF); ALCALASE®, BLAZE®, DURALASE™, DURAZYM™, RELASE®, RELASE® Ultra, SAVINASE®, SAVINASE® Ultra, PRIMASE®, POLARZYME®, KANNASE®, LIQUANASE®, LIQUANASE® Ultra, OVOZYME®, CORONASE®, CORONASE® Ultra, NEUTRASE®, EVERLASE® and ESPERASE® (Novozymes A/S), those sold under the tradename MAXATASE®, MAXACAL®, MAXAPEM®, PURAFECT®, PURAFECT® Prime, PURAFECT MA®, PURAFECT Ox®, PURAFECT OxP®, PURAMAX®, PROSPERASE®, FN2®, FN3®, FN4®, EXCELLASE®, ERASER®, ULTIMASE®, OPTI-CLEAN®, EFFECTENZ®, PREFERENZ® and OPTI-MASE® (Danisco/DuPont), AXAPEM™ (Gist-Brocases N.V.), *Bacillus lentus* Alkaline Protease, and KAP (*Bacillus alkalophilus* subtilisin) from Kao.

At least one protease may be selected from serine proteases (EC 3.4.21). Serine proteases or serine peptidases (EC 3.4.21) are characterized by having a serine in the catalytically active site, which forms a covalent adduct with the substrate during the catalytic reaction. A serine protease may be selected from the group consisting of chymotrypsin (e.g., EC 3.4.21.1), elastase (e.g., EC 3.4.21.36), elastase (e.g., EC 3.4.21.37 or EC 3.4.21.71), granzyme (e.g., EC 3.4.21.78 or EC 3.4.21.79), kallikrein (e.g., EC 3.4.21.34, EC 3.4.21.35, EC 3.4.21.118, or EC 3.4.21.119,) plasmin (e.g., EC 3.4.21.7), trypsin (e.g., EC 3.4.21.4), thrombin (e.g., EC 3.4.21.5,) and subtilisin (also known as subtilopeptidase, e.g., EC 3.4.21.62), the latter hereinafter also being referred to as "subtilisin".

Cellulase

"Cellulases", "cellulase enzymes" or "cellulolytic enzymes" are enzymes involved in hydrolysis of cellulose. Three major types of cellulases are known, namely endo-ss-1,4-glucanase (endo-1,4-P-D-glucan 4-glucanohydrolase, E.C. 3.2.1.4; hydrolyzing 0-1,4-glucosidic bonds in cellulose), cellobiohydrolase (1,4-P-D-glucan cellobiohydrolase, EC 3.2.1.91), and ss-glucosidase (EC 3.2.1.21).

Cellulase enzymes have been described in patents and published patent applications including, but not limited to: WO1997/025417, WO1998/024799, WO2003/068910, WO2005/003319, and WO2009020459.

Commercially available cellulase enzymes include are CELLUZYME™, ENDOLASE™ CAREZYME™, CEL-LUSOFT™, RENOZYME™, CELLUCLEAN™ (from Novozymes A/S), ECOSTONE™, BIOTOUCH™, ECON-ASE™, ECOPULP™ (from AB Enzymes Finland), CLAZI-NASE™, and PURADAX HA™, Genencor detergent cellulase L, INDIAGE™ Neutra (from Genencor International Inc./DuPont), REVITALENZ™ (2000 from DuPont), PRI-MAFAST™ (DuPont) and KAC-500™ (from Kao Corporation).

Cellulases according to the invention have "cellulolytic activity" or "cellulase activity". Assays for measurement of cellulolytic activity are known to those skilled in the art. For example, cellulolytic activity may be determined by cellulase hydrolyses carboxymethyl cellulose to reducing carbohydrates, the reducing ability of which is determined colorimetrically by means of the ferricyanide reaction, according to Hoffman, W. S., J. Biol. Chem. 120, 51 (1937).

Mannanase

Mannanase (E.C. 3.2.1.78) enzymes hydrolyze internal 3-1,4 beta-D-mannosidic linkages in mannans, galactomannans and glucomannans. "Mannanase" may be an alkaline mannanase of Family 5 or 26. Mannanase are useful components of washing and/or cleaning formulations since mannanase remove part of hemicellulose containing stains. Insufficient removal of these types of stains may e.g. result in fabric graying. The major constituents of hemicellulose are hetero-1,4-D-xylans and herto-1,4-beta-mannans. Mannans are polysaccharides with a backbone of 0-1,4-linked D-mannopyranosyl residues, which can contain galactose or acetyl substitutions and may have glucose residues in the backbone. Mannanase enzymes are known to be derived from wild-type from *Bacillus* or *Humicola*, particularly *B.*

*agaradhaerens, B. licheniformis, B. halodurans, B. clausii,* or *H. insolens.* Suitable mannanases are described in WO 99/064619.

Commercially available mannanase enzymes include: MANNAWAY® (Novozymes AIS).

Pectate Lyase

Pectate lyase (E.C. 4.2.2.2) enzymes eliminative cleavage of (1→4)-alpha-D-galacturonan to give oligosaccharides with 4-deoxy-alpha-D-galact-4-enuronosyl groups at their non-reducing ends. Pectate lyase enzymes have been described in patents and published patent applications including, but not limited to: WO2004/090099. Pectate lyase are known to be derived from *Bacillus*, particularly *B. licheniformis* or *B. agaradhaerens*, or a variant derived of any of these, e.g. as described in U.S. Pat. No. 6,124,127, WO 99/027083, WO 99/027084, WO 2002/006442, WO 2002/092741, WO 2003/095638.

Commercially available pectate lyase enzymes include: XPECT™, PECTAWASH™ and PECTAWAY™ (Novozymes A/S); PRIMAGREEN™, ECOSCOUR (DuPont).

Nuclease

Nuclease (EC 3.1.21.1) also known as Deoxyribonuclease I, or DNase preforms endonucleolytic cleavage to 5'-phosphodinucleotide and 5'-phosphooligonucleotide end-products.

Nuclease enzymes have been described in patents and published patent applications including, but not limited to: U.S. Pat. No. 3,451,935, GB1300596, DE10304331, WO2015155350, WO2015155351, WO2015166075, WO2015181287, and WO2015181286.

In one aspect of the invention, at least one amylase variant of the invention is provided in combination with at least one protease. In one embodiment, an amylase variant of the invention is stable in the presence of at least one protease. In one embodiment, an amylase variant of the invention has increased protease stability when compared to the respective amylase parent. In one embodiment, at least one protease is selected from subtilisin 309 as disclosed as sequence a) in Table I of WO 89/06279 or a variant thereof which is at least 80% identical thereto and has proteolytic activity. In one embodiment, an amylase variant of the invention has increased protease stability in the presence of said subtilisin 309 or a variant thereof which is at least 80% identical thereto when compared to the amylase according to SEQ ID NO: 1.

The protease may itself be stabilized by a protease stabilizer or the protease may be non-stabilized. In one embodiment, an amylase variant of the invention has increased protease stability in the presence of a non-stabilized subtilisin 309 or a non-stabilized variant thereof which is at least 80% identical thereto, when compared to the amylase according to SEQ ID NO: 1.

Methods of Making

In another embodiment, the present invention refers to a method of making the variant polypeptide as described herein, comprising: providing a nucleic acid sequence encoding the polypeptide described herein, transforming the nucleic acid sequence into a host cell, cultivating the host cell to produce the variant polypeptide, and optionally purifying the variant polypeptide from the host cell.

A polynucleotide encoding a polypeptide may be "expressed". The term "expression" or "gene expression" means the transcription of a specific gene or specific genes or specific nucleic acid construct. The term "expression" or "gene expression" means the transcription of a gene or genes or genetic construct into structural RNA (e.g., rRNA, tRNA) or mRNA with or without subsequent translation of the latter into a protein. The process includes transcription of DNA and processing of the resulting mRNA product.

Industrial production of enzymes usually is done by using expression systems. "Expression system" may mean a host microorganism, expression hosts, host cell, production organism, or production strain and each of these terms can be used interchangeably. In one embodiment, the expression host is selected from the group consisting of: a bacterial expression system, a yeast expression system, a fungal expression system, and a synthetic expression system. The expression host may be a wildtype cell or a recombinant cell. "Wild-type cells" herein means cells prior to a certain modification. The term "recombinant cell" (also called "genetically modified cell" herein) refers to a cell which has been genetically altered, modified or engineered such it that exhibits an altered, modified or different genotype as compared to the wild-type cell which it was derived from.

The "recombinant cell" may comprise an exogenous polynucleotide encoding a certain protein or enzyme and therefore may express said protein or enzyme.

Thus, in one embodiment, the invention is directed to a genetic construct comprising a polynucleotide encoding the amylase as described herein.

In one embodiment, the invention is directed to an expression vector comprising a polynucleotide encoding the amylase as described herein.

In one embodiment, the invention is directed to a host cell comprising a polynucleotide encoding the amylase as described herein.

In yet another embodiment, the present invention is directed to a method of expressing a polynucleotide, comprising the steps of (a) providing a host cell comprising a heterologous nucleic acid construct comprising a polynucleotide encoding the amylase described herein by introducing the nucleic acid construct comprising the polynucleotide encoding the amylase as described herein into the host cell;

(b) cultivating the recombinant host cell of step (a) under conditions conductive for the expression of the polynucleotide; and (c) optionally, recovering a protein of interest encoded by the polynucleotide.

Examples of expression systems include but are not limited to: *Aspergillus niger, Aspergillus oryzae, Hansenula polymorpha, Thermomyces lanuginosus, Fusarium oxysporum, Fusarium heterosporum, Escherichia coli, Bacillus*, preferably *Bacillus pumilus, Bacillus subtilis*, or *Bacillus licheniformis, Pseudomonas*, preferably *Pseudomonas fluorescens, Pichia pastoris* (also known as *Komagataella phaffii), Myceliopthora thermophile* (C1), *Themothelomyces thermophila, Schizosaccharomyces pombe, Trichoderma*, preferably *Trichoderma reesei* and *Saccharomyces*, preferably *Saccharomyces cerevisiae*. The variant polypeptides may be produced using the expression system listed above.

In one embodiment, the bacterial expression system is selected from an *E. coli*, a *Bacillus*, a *Pseudomonas*, and a *Streptomyces*. In one embodiment, the yeast expression system is selected from a *Candida*, a *Pichia*, a *Saccharomyces*, and/or a *Schizosaccharomyces*. In one embodiment, the fungal expression system is selected from a *Penicillium*, an *Aspergillus*, a *Fusarium*, a *Myceliopthora*, a *Rhizomucor*, a *Rhizopus*, a *Thermomyces*, and a *Trichoderma*.

The term "heterologous" (or exogenous or foreign or recombinant) in the context of polynucleotides and polypeptides is defined herein as:

(a) not native to the host cell;

(b) native to the host cell but structural modifications, e.g., deletions, substitutions, and/or insertions, are included as a result of manipulation of the DNA of the host cell by recombinant DNA techniques to alter the native sequence; or (c) native to the host cell but expression is quantitatively altered, or expression is directed from a genomic location different from the native host cell as a result of manipulation of the DNA of the host cell by recombinant DNA techniques, e.g., a stronger promoter.

With respect to two or more polynucleotide sequences or two or more amino acid sequences, the term "heterologous" is used to characterize that the two or more polynucleotide sequences or two or more amino acid sequences do not occur naturally in the specific combination with each other.

"Genetic construct" or "expression cassette" as used herein, is a DNA molecule composed of at least one sequence of interest to be expressed, operably linked to one or more control sequences (at least to a promoter) as described herein. Typically, the expression cassette comprises three elements: a promoter sequence, an open reading frame, and a 3' untranslated region that, in eukaryotes, usually contains a polyadenylation site. Additional regulatory elements may include transcriptional as well as translational enhancers. An intron sequence may also be added to the 5' untranslated region (UTR) or in the coding sequence to increase the amount of the mature message that accumulates in the cytosol. The expression cassette may be part of a vector or may be integrated into the genome of a host cell and replicated together with the genome of its host cell. The expression cassette usually is capable of increasing or decreasing expression.

The term "vector" as used herein comprises any kind of construct suitable to carry foreign polynucleotide sequences for transfer to another cell, or for stable or transient expression within a given cell. The term "vector" as used herein encompasses any kind of cloning vehicles, such as but not limited to plasmids, phagemids, viral vectors (e.g., phages), bacteriophage, baculoviruses, cosmids, fosmids, artificial chromosomes, or and any other vectors specific for specific hosts of interest. Low copy number or high copy number vectors are also included. Foreign polynucleotide sequences usually comprise a coding sequence which may be referred to herein as "gene of interest". The gene of interest may comprise introns and exons, depending on the kind of origin or destination of host cell.

A vector as used herein may provide segments for transcription and translation of a foreign polynucleotide upon transformation into a host cell or host cell organelles. Such additional segments may include regulatory nucleotide sequences, one or more origins of replication that is required for its maintenance and/or replication in a specific cell type, one or more selectable markers, a polyadenylation signal, a suitable site for the insertion of foreign coding sequences such as a multiple cloning site etc. One example is when a vector is required to be maintained in a bacterial cell as an episomal genetic element (e.g. plasmid or cosmid molecule). Non-limiting examples of suitable origins of replication include the fl-ori and colE1.

A vector may replicate without integrating into the genome of a host cell, e.g. as a plasmid in a bacterial host cell, or it may integrate part or all of its DNA into the genome of the host cell and thus lead to replication and expression of its DNA.

Foreign nucleic acid may be introduced into a vector by means of cloning. Cloning may mean that by cleavage of the vector (e.g. within the multiple cloning site) and the foreign polynucleotide by suitable means and methods (e.g., restriction enzymes), fitting structures within the individual nucleic acids may be created that enable the controlled fusion of said foreign nucleic acid and the vector.

Once introduced into the vector, the foreign nucleic acid comprising a coding sequence may be suitable to be introduced (transformed, transduced, transfected, etc.) into a host cell or host cell organelles. A cloning vector may be chosen suitable for expression of the foreign polynucleotide sequence in the host cell or host cell organelles.

The term "introduction" or "transformation" as referred to herein encompasses the transfer of an exogenous polynucleotide into a host cell, irrespective of the method used for transfer. That is, the term "transformation" as used herein is independent from vector, shuttle system, or host cell, and it not only relates to the polynucleotide transfer method of transformation as known in the art (cf., for example, Sambrook, J. et al. (1989) Molecular Cloning: A Laboratory Manual, 2nd Ed., Cold Spring Harbor Laboratory Press, Cold Spring Harbor, NY), but it encompasses any further kind polynucleotide transfer methods such as, but not limited to, transduction or transfection. Plant tissue capable of subsequent clonal propagation, whether by organogenesis or embryogenesis, may be transformed with a genetic construct and a whole plant regenerated therefrom. The particular tissue chosen will vary depending on the clonal propagation systems available for, and best suited to, the particular species being transformed.

In one embodiment of the invention, a vector is used for transformation of a host cell.

The polynucleotide may be transiently or stably introduced into a host cell and may be maintained non-integrated, for example, as a plasmid. "Stable transformation" may mean that the transformed cell or cell organelle passes the nucleic acid comprising the foreign coding sequence on to the next generations of the cell or cell organelles. Usually stable transformation is due to integration of nucleic acid comprising a foreign coding sequence into the chromosomes or as an episome (separate piece of nuclear DNA).

"Transient transformation" may mean that the cell or cell organelle once transformed expresses the foreign nucleic acid sequence for a certain time—mostly within one generation. Usually transient transformation is due to nucleic acid comprising a foreign nucleic acid sequence is not integrated into the chromosomes or as an episome.

Alternatively, it may be integrated into the host genome. The resulting transformed plant cell may then be used to regenerate a transformed plant in a manner known to persons skilled in the art.

Recombinant cells may exhibit "increased" or "decreased" expression when compared to the respective wild-type cell.

The term "increased expression", "enhanced expression" or "overexpression" as used herein means any form of expression that is additional to the original wild-type expression level (which can be absence of expression or immeasurable expression as well). Reference herein to "increased expression", "enhanced expression" or "overexpression" is taken to mean an increase in gene expression and/or, as far as referring to polypeptides, increased polypeptide levels and/or increased polypeptide activity, relative to control organisms. The increase in expression may be in increasing order of preference at least 5%, at least 10%, at least 20%, at least 30%, at least 40%, at least 50%, at least 60%, at least 70%, at least 80%, at least 85%, at least 90%, or 100% or even more compared to that of control organisms.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to increase expression of a nucleic acid encoding the polypeptide of interest. For example, endogenous promoters may be altered in vivo by mutation, deletion, and/or substitution (see Kmiec et al., U.S. Pat. No. 5,565,350; Zarling et al., WO 93/22443), or isolated promoters may be introduced into an organism in the proper orientation and distance from a gene of the present invention so as to control the expression of the gene.

An intron sequence may also be added to the 5' untranslated region (UTR) or the coding sequence of the partial coding sequence to increase the amount of the mature message that accumulates in the cytosol. Inclusion of a spliceable intron in the transcription unit in expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit.

To obtain increased expression or overexpression of a polypeptide most commonly the nucleic acid encoding this polypeptide is overexpressed in sense orientation with a polyadenylation signal. Introns or other enhancing elements may be used in addition to a promoter suitable for driving expression with the intended expression pattern.

Enzymes are generally produced commercially by using recombinant cells which express the desired enzyme by cultivation of the same under conditions suitable for expression of the desired enzyme.

Cultivation normally takes place in a suitable nutrient medium allowing the recombinant cells to grow (this process may be called fermentation) and express the desired protein. At the end of fermentation, fermentation broth is collected and may be further processed, wherein the fermentation broth comprises a liquid fraction and a solid fraction.

The enzyme of interest may be further purified from the fermentation broth. The term "purification" or "purifying" refers to a process in which at least one component, e.g., a protein of interest, is separated from at least another component, e.g., a particulate matter of a fermentation broth, and transferred into a different compartment or phase, wherein the different compartments or phases do not necessarily need to be separated by a physical barrier. Examples of such different compartments are two compartments separated by a filtration membrane or cloth, i.e., filtrate and retentate; examples of such different phases are pellet and supernatant or cake and filtrate, respectively. The resulting solution after purifying the enzyme of interest from the fermentation broth is called herein "purified enzyme solution".

The desired enzyme may be secreted (into the liquid fraction of the fermentation broth) or may not be secreted from the host cells (and therefore is comprised in the cells of the fermentation broth). Depending on this, the desired enzyme may be recovered from the liquid fraction of the fermentation broth or from cell lysates. Recovery of the desired enzyme uses methods known to those skilled in the art. Suitable methods for recovery of proteins or enzymes from fermentation broth include but are not limited to collection, centrifugation, filtration, extraction, and precipitation. If the enzyme of interest precipitates or crystallizes in the fermentation broth or binds at least in part to the particulate matter of the fermentation broth additional treatment steps might be needed to release the enzyme from the biomass or solubilize enzyme crystals and precipitates. U.S. Pat. No. 6,316,240B1 describes a method for recovering an enzyme, which precipitates and/or crystallizes during fermentation, from the fermentation broth. In case the desired enzyme is comprised in the cells of the fermentation broth release of the enzyme from the cells might be needed. Release from the cells can be achieved for instance, but not being limited thereto, by cell lysis with techniques well known to the skilled person.

The purified enzyme solution may be further processed to form an "enzyme formulation". "Enzyme formulation" means any non-complex formulation comprising a small number of ingredients, wherein the ingredients serve the purpose of stabilizing the enzymes comprised in the enzyme formulation and/or the stabilization of the enzyme formulation itself. The term "enzyme stability" relates to the retention of enzymatic activity as a function of time during storage or operation. The term "enzyme formulation stability" relates to the maintenance of physical appearance of the enzyme formulation during storage or operation as well as the avoidance of microbial contamination during storage or operation.

An "enzyme formulation" is a composition which is meant to be formulated into a complex formulation which itself may be determined for final use. An "enzyme formulation" according to the invention is not a complex formulation comprising several components, wherein the components are formulated into the complex formulation to exert each individually a specific action in a final application. A complex formulation may be without being limited thereto a detergent formulation, wherein individual detergent components are formulated in amounts effective in the washing performance of the detergent formulation.

In one aspect of the invention, at least one amylase variant of the invention is comprised in an enzyme formulation.

The enzyme formulation can be either solid or liquid. Enzyme formulations can be obtained by using techniques known in the art. For instance, without being limited thereto, solid enzyme formulations can be obtained by extrusion or granulation. Suitable extrusion and granulation techniques are known in the art and are described for instance in WO9419444A1 and WO9743482A1.

"Liquid" in the context of enzyme formulation is related to the physical appearance at 20° C. and 101.3 kPa.

Liquid enzyme formulations may comprise amounts of enzyme in the range of 0.1% to 40% by weight, or 0.5% to 30% by weight, or 1% to 25% by weight, or 3% to 10%, all relative to the total weight of the enzyme formulation.

The liquid enzyme formulation may comprise more than one type of enzyme. In one embodiment, the enzyme formulation comprises one or more amylases according to the present invention. In one embodiment, the enzyme formulation comprises one or more amylases according to the present invention and at least one additional enzyme selected from the group consisting of selected from the group consisting of: a second amylase, a lipase, a protease, a cellulase, a laccase, a pectinase, a nuclease, and any combination thereof.

Aqueous enzyme formulations of the invention may comprise water in amounts of more than about 50% by weight, more than about 60% by weight, more than about 70% by weight, or more than about 80% by weight, all relative to the total weight of the enzyme formulation.

Liquid enzyme formulations of the invention may comprise residual components such as salts originating from the fermentation medium, cell debris originating from the production host cells, metabolites produced by the production host cells during fermentation.

In one embodiment, residual components may be comprised in liquid enzyme formulations in amounts less than 30% by weight, less than 20% by weight less, than 10% by weight, or less than 5% by weight, all relative to the total weight of the aqueous enzyme formulation. In one embodiment, the enzyme formulation, in particular the liquid enzyme formulation, comprises in addition to the one or more enzymes one or more additional compounds selected from the group consisting of solvent, salt, pH regulator, preservative, stabilizer, chelators, and thickening agent. The preservative in a liquid enzyme formulation maybe a sorbitol, a benzoate, a proxel, or any combination therefore. The stabilizers in a liquid enzyme formulation maybe an MPG, a glycerol, an acetate, or any combination thereof. The chelators in a liquid enzyme formulation maybe a citrate.

In one embodiment, an enzyme formulation comprises at least one polypeptide variant of the invention and at least one preservative. Non-limiting examples of suitable preservatives include (quaternary) ammonium compounds, isothiazolinones, organic acids, and formaldehyde releasing agents. Non-limiting examples of suitable (quaternary) ammonium compounds include benzalkonium chlorides, polyhexamethylene biguanide (PHMB), Didecyldimethylammonium chloride (DDAC), and N-(3-aminopropyl)-N-dodecylpropane-1,3-diamine (Diamine). Non-limiting examples of suitable isothiazolinones include 1,2-benzisothiazolin-3-one (BIT), 2-methyl-2H-isothiazol-3-one (MIT), 5-chloro-2-methyl-2H-isothiazol-3-one (CIT), 2-octyl-2H-isothiazol-3-one (OIT), and 2-butyl-benzo [d]isothiazol-3-one (BBIT). Non-limiting examples of suitable organic acids include benzoic acid, sorbic acid, L-(+)-lactic acid, formic acid, and salicylic acid. Non-limiting examples of suitable formaldehyde releasing agent include N,N'-methylenebismorpholine (MBM), 2,2',2"-(hexahydro-1,3,5-triazine-1,3,5-triyl)triethanol (HHT), (ethylenedioxy)dimethanol, .alpha.,.alpha.',.alpha."-trimethyl-1,3,5-triazine-1,3,5 (2H,4H,6H)-triethanol (HPT), 3,3'-methylenebis[5-methyloxazolidine](MBO), and cis-1-(3-chloroallyl)-3,5,7-triaza-1-azoniaadamantane chloride (CTAC).

Further useful preservatives include iodopropynyl butylcarbamate (IPBC), halogen releasing compounds such as dichloro-dimethyl-hydantoine (DCDMH), bromo-chloro-dimethyl-hydantoine (BCDMH), and dibromo-dimethyl-hydantoine (DBDMH); bromo-nitro compounds such as Bronopol (2-bromo-2-nitropropane-1,3-diol), 2,2-dibromo-2-cyanoacetamide (DBNPA); aldehydes such as glutaraldehyde; phenoxyethanol; Biphenyl-2-ol; and zinc or sodium pyrithione.

In one embodiment, an enzyme formulation comprises at least one polypeptide variant of the invention and at least one enzyme stabilizer. An enzyme stabilizer is selected from substances which are capable of reducing loss of enzymatic activity during storage of at least one enzyme comprised in a liquid enzyme formulation. Reduced loss of enzymatic activity within this invention may mean that the loss of enzymatic activity is reduced by at least 5%, by at least 10%, by at least 15%, by at least 20%, by at least 25%, by at least 30%, by at least 40%, by at least 50%, by least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% when compared to the initial enzymatic activity before storage. Preferred stabilizers are selected from the group consisting of salt (e.g., CaCl$_2$)), propanediol, polyethylene glycol, an MPG, a glycerol, an acetate, or any combination thereof.

Enzyme Applications

In another embodiment, the polypeptide variant as described herein may be used in foods, for example the enzyme can be an additive for baking. The enzymes can be used in feed, for example the enzyme is an animal feed additive. The enzyme can be used in the starch processing industry, for example the amylases are used in the conversion of starch to ethanol or sugars (high fructose corn syrup) and other byproducts such as oil, dry distiller's grains, etc. The polypeptide variants are used in in pulp and paper processing, for example, the enzymes can be used for improving paper strength. The enzymes can be used for mining and oil well services, for example cellulases can be used for breaking guar during oil well fracturing. In one embodiment, the polypeptide variant as described herein are used in detergent formulations or cleaning formulations.

In one embodiment, the present invention refers to a method of preparing a dough or a baked product prepared from the dough, the method comprising adding one of the variant polypeptides having amylase activity as described herein to the dough and baking it. In one embodiment, the present invention refers to a method of use of the variant polypeptide having amylase activity as described herein for processing starch. In one embodiment, the present invention refers to a method of use of the variant polypeptide having amylase activity as described herein for cleaning or washing textiles, hard surfaces, or dishes. In one embodiment, the present invention refers to a method of use of the variant polypeptide having amylase activity as described herein for making ethanol. In one embodiment, the present invention refers to a method of use of the variant polypeptide having amylase activity as described herein for processing pulp or paper. In one embodiment, the present invention refers to a method of use of the variant polypeptide having amylase activity as described herein for feeding an animal.

In one embodiment, the amylases of the present invention are used in detergent formulations or cleaning formulations.

"Detergent formulation" or "cleaning formulation" means compositions designated for cleaning soiled material. Cleaning includes laundering and hard surface cleaning. Soiled material according to the invention includes textiles and/or hard surfaces.

The term "laundering" relates to both household laundering and industrial laundering and means the process of treating textiles with a solution containing a detergent composition of the present invention. The laundering process may be carried out by using technical devices such as a household or an industrial washing machine. Alternatively, the laundering process may be done by hand.

The term "textile" means any textile material including yarns (thread made of natural or synthetic fibers used for knitting or weaving), yarn intermediates, fibers, non-woven materials, natural materials, synthetic materials, as well as fabrics (a textile made by weaving, knitting or felting fibers) made of these materials such as garments (any article of clothing made of textile), cloths and other articles.

The term "fibers" includes natural fibers, synthetic fibers, and mixtures thereof. Examples of natural fibers are of plant (such as flax, jute and cotton) or animal origin, comprising proteins like collagen, keratin and fibroin (e.g. silk, sheep wool, angora, mohair, cashmere). Examples for fibers of synthetic origin are polyurethane fibers such as Spandex® or Lycra®, polyester fibers, polyolefins such as elastofin, or polyamide fibers such as nylon. Fibers may be single fibers or parts of textiles such as knitwear, woven, or nonwovens.

The term "hard surface cleaning" is defined herein as cleaning of hard surfaces wherein hard surfaces may include any hard surfaces in the household, such as floors, furnishing, walls, sanitary ceramics, glass, metallic surfaces including cutlery or dishes.

The term "dish wash" refers to all forms of washing dishes, e.g. by hand or automatic dish wash. Dish washing includes, but is not limited to, the cleaning of all forms of crockery such as plates, cups, glasses, bowls, all forms of cutlery such as spoons, knives, forks and serving utensils as well as ceramics, plastics such as melamine, metals, china, glass and acrylics.

The detergent formulation of the invention comprises one or more detergent component(s). The component(s) chosen depend(s) on the desired cleaning application and/or physical form of a detergent composition.

The term "detergent component" is defined herein to mean any types of ingredient, which is suitable for detergent compositions, such as surfactants, building agents, polymers, bleaching systems. Any component(s) known in the art acknowledging their known characteristics are suitable detergent component(s) according to the invention. Detergent components in one embodiment means components which provide washing or cleaning performance, or which effectively aid the processing (maintain physical characteristics during processing, storage and use; e.g. rheology modifiers, hydrotropes, desiccants) when present in effective amounts.

Usually, a detergent composition is a complex formulation of more than two detergent components.

Detergent components may have more than one function in the final application of a detergent formulation, therefore any detergent component mentioned in the context of a specific function herein, may also have another function in the final application of a detergent formulation. The function of a specific detergent component in the final application of a detergent formulation usually depends on its amount within the detergent formulation, i.e. the effective amount of a detergent component.

The term "effective amount" includes amounts of certain components to provide effective stain removal and effective cleaning conditions (e.g. pH, quantity of foaming), amounts of certain components to effectively provide optical benefits (e.g. optical brightening, dye transfer inhibition), and amounts of certain components to effectively aid the processing (maintain physical characteristics during processing, storage and use; e.g. rheology modifiers, hydrotropes, desiccants).

In one embodiment, a detergent formulation is a formulation of more than two detergent components, wherein at least one component is effective in stain-removal, at least one component is effective in providing the optimal cleaning conditions, and at least one component is effective in maintaining the physical characteristics of the detergent.

Cleaning performance is evaluated under relevant cleaning conditions. The term "relevant cleaning conditions" herein refers to the conditions, particularly cleaning temperature, time, cleaning mechanics, suds concentration, type of detergent and water hardness, actually used in laundry machines, automatic dish washers or in manual cleaning processes.

Individual detergent components and usage in detergent compositions are known to those skilled in the art. Suitable detergent components comprise inter alia surfactants, builders, polymers, alkaline, bleaching systems, fluorescent whitening agents, suds suppressors and stabilizers, hydrotropes, and corrosion inhibitors. Further examples are described e.g. in "complete Technology Book on Detergents with Formulations (Detergent Cake, Dishwashing Detergents, Liquid & Paste Detergents, Enzyme Detergents, Cleaning Powder & Spray Dried Washing Powder)", Engineers India Research Institute (EIRI), 6th edition (2015). Another reference book for those skilled in the art may be "Detergent Formulations Encyclopedia", Solverchem Publications, 2016.

Detergent components vary in type and/or amount in a detergent formulation depending on the desired application such as laundering white textiles, colored textiles, and wool. The component(s) chosen further depend(s) on physical form of a detergent formulation (liquid, solid, gel, provided in pouches or as a tablet, etc.). The component(s) chosen e.g. for laundering formulations further depend on regional conventions which themselves are related to aspects like washing temperatures used, mechanics of laundry machine (vertical vs. horizontal axis machines), water consumption per wash cycle etc. and geographical characteristics like average hardness of water.

For example: A low detergent concentration system includes laundering formulations where less than about 800 ppm of detergent components are present in the wash water. A medium detergent concentration includes laundering formulations where between about 800 ppm and about 2,000 ppm of detergent components are present in the wash water. A high detergent concentration includes laundering formulations where more than about 2,000 ppm of detergent components are present in the wash water.

The numeric ranges recited for the individual detergent components provide amounts comprised in detergent compositions. Such ranges have to be understood to be inclusive of the numbers defining the range and include each integer within the defined range.

If not described otherwise, "% by weight" or "% w/w" is meant to be related to total detergent composition. In this case "% by weight" or "% w/w" is calculated as follows: concentration of a substance as the weight of that substance divided by the total weight of the composition, multiplied by 100.

Detergent formulations of the invention may comprise one or more surfactant(s). "Surfactant" (synonymously used herein with "surface active agent") means an organic chemical that, when added to a liquid, changes the properties of that liquid at an interface. According to its ionic charge, a surfactant is called non-ionic, anionic, cationic, or amphoteric.

Non-limiting examples of surfactants are disclosed McCutcheon's 2016 Detergents and Emulsifiers, and McCutcheon's 2016 Functional Materials, both North American and International Edition, MC Publishing Co, 2016 edition. Further useful examples are disclosed in earlier editions of the same publications which are known to those skilled in the art.

Non-ionic surfactant means a surfactant that contains neither positively nor negatively charged (i.e. ionic) functional groups. In contrast to anionic and cationic surfactants, non-ionic surfactants do not ionize in solution.

Preferred Methods and Uses

Preferred herein is a method of making the amylase comprising an A and B domain and a C domain wherein the amino acid sequence of the A and B domain is at least 75% identical to the amino acid sequence of SEQ ID NO: 42 and the amino acid sequence of the C domain is at least 75% identical to the amino acid sequence of SEQ ID NO: 44; comprising: providing a nucleic acid sequence encoding said amylase; transforming the nucleic acid sequence into an expression host, cultivating the expression host to produce the amylase, and optionally purifying the amylase.

Preferred herein is a method of making the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37; comprising: providing a nucleic acid sequence comprising: SEQ ID NO:55, SEQ ID NO:2, SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38; transforming the nucleic acid sequence into an expression host, cultivating the expression host to produce the amylase, and optionally purifying the amylase.

Preferred herein is a method of making the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54; comprising: providing a nucleic acid sequence comprising: SEQ ID NO:55; transforming the nucleic acid sequence into an expression host, cultivating the expression host to produce the amylase, and optionally purifying the amylase.

The method of making the amylase wherein the expression host is selected from the group consisting of: a bacterial expression system, a yeast expression system, a fungal expression system, and a synthetic expression system.

The method of making the amylase wherein the bacterial expression system is selected from an E. coli, a Bacillus, a Pseudomonas, and a Streptomyces, wherein the yeast expression system is selected from a Candida, a Pichia, a Saccharomyces, a Schizosaccharomyces or, wherein the fungal expression system is selected from a Penicillium, an Aspergillus, a Fusarium, a Myceliopthora, a Themothelomyces, a Rhizomucor, a Rhizopus, a Thermomyces, and a Trichoderma, preferably Bacillus.

Preferred herein is a method of making the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ TD NO:37; wherein the expression host is a *Bacillus* host cell, preferably selected from *Bacillus pumilus, Bacillus subtilis*, and *Bacillus licheniformis*, most preferably, *Bacillus licheniformis*.

Preferred herein is a method of making the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, wherein the expression host is a *Bacillus* host cell, preferably selected from *Bacillus pumilus, Bacillus subtilis*, and *Bacillus licheniformis*, most preferably, *Bacillus licheniformis*.

Preferred herein is a method of use of a C domain of a first amylase said C domain having an amino acid sequence which has at least 75% identity to the amino acid sequence of SEQ ID NO: 44 for improving one or more properties selected from the group consisting of stability, pH profile, expression, activity, thermostability, specific activity, substrate specificity, pH-dependent activity, pH-dependent stability, oxidative stability, Ca2+ dependency, performance in laundry, processing starch, cleaning textiles, cleaning hard surfaces, cleaning dishes, making ethanol, processing pulp or paper, and feeding an animal of a second alpha amylase having an A and B domain with at least 75% identity to the amino acid sequence of SEQ ID NO: 42 said use comprising replacing the C domain of the second alpha-amylase with the C domain of the first alpha-amylase.

Preferred herein is a method of preparing a dough or a baked product prepared from the dough, the method comprising adding the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, to the dough and baking it.

Preferred herein is a method of preparing a dough or a baked product prepared from the dough, the method comprising adding the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54 to the dough and baking it.

Preferred herein is a method of use of the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, for processing starch, for cleaning or washing textiles, hard surfaces, or dishes, for making ethanol, for processing pulp or paper, or for feeding an animal, preferably, for cleaning or washing textiles, hard surfaces, or dishes.

Preferred herein is a method of use of the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54 for processing starch, for cleaning or washing textiles, hard surfaces, or dishes, for making ethanol, for processing pulp or paper, or for feeding an animal.

Preferred herein is a method of use of the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, for cleaning or washing textiles, hard surfaces, or dishes.

Preferred herein is a method of use of the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54 for cleaning or washing textiles, hard surfaces, or dishes.

Preferred herein is a method of use of the amylase comprising an amino acid sequence that is at least 95%, at least 96%, at least 97%, at least 98%, at least 98.5%, at least 99%, at least 99.5%, or 100% identical to the full-length amino acid sequence of: SEQ ID NO:54 for cleaning or washing textiles, hard surfaces, or dishes.

Preferred herein is a method of use of the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37, for cleaning or washing textiles.

Preferred herein is a method of use of the amylase comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5%, or 100% identical to the full-length amino acid sequence of: SEQ ID NO:54 for cleaning or washing textiles.

Preferred herein is a method of use of the amylase comprising an amino acid sequence that is at least 95%, at least 96%, at least 97%, at least 98%, at least 98.5%, at least 99%, at least 99.5%, or 100% identical to the full-length amino acid sequence of SEQ ID NO:54 for cleaning or washing textiles.

EXAMPLES

Example 1 Generation of Amylase Expression Constructs

The genes coding for the amino acid sequences were codon optimized to match the native codon abundance of *Bacillus subtilis*, and physically synthesized by an external, commercial DNA provider. Upon receipt, these genes were cloned by restriction-ligation based standard protocols into a gram-positive expression vector featuring regions coding for a promoter, a secretion signal peptide, and a ribosome binding site that are known to provide expression in the Bacillaceae family of organisms (e.g. the promoter driving expression of the *B. subtilis* amyE gene, the signal peptide of *B. subtilis* YdjM enzyme, and a consensus Shine-Dalgarno sequence). The vector furthermore contained an antibiotic based selection marker and an origin of replication. Post reaction, the plasmid assembly mixtures were transformed according to the method of Spizizen (*Anagnostopoulos, C.* and *Spizizen, J.* (1961). *J. Bacteriol.* 81, 741-746.) into a *B. subtilis* PY79 KO-7S (*Bacillus* Genetic Stock Center, BGSCID:1S145; Zeigler D.R) derivative named Bs #056 with an integrated DNA-methyltransferase gene as described for *B. subtilis* Bs #053 in WO2019016051. Successful transformations were selected by plating on LB agar plates supplemented with 20 g/ml kanamycin sulfate and incubating overnight at 37 degrees C. After the overnight selection, individual colonies were obtained which were then grown in a rich medium (e.g. LB broth) with 20 g/ml kanamycin sulfate overnight at 37 degrees with shaking at 250 rpm. The following morning, cells were pelleted by centrifugation, and plasmid DNA was isolated by alkaline lysis method with a Macherey-Nagel NucleoSpin kit. The isolated DNA could then be transformed into electrocompetent *Bacillus licheniformis* cells.

Preparation of electrocompetent *B. licheniformis* cells and transformation of DNA was performed as essentially described by Brigidi et al (*Brigidi, P., Mateuzzi, D.* (1991). *Biotechnol.* Techniques 5, 5) with the following modification: Upon transformation of DNA, cells are recovered in lml LBSPG buffer and incubated for 60 min at 37° C. (Vehmaanpera J., 1989, *FEMS Microbio. Lett.*, 61: 165-170) following plating on selective LB-agar plates (20 g/ml kanamycin sulfate) and incubating overnight at 37 degrees C.

Example 2: Amylase Expression and Protein Quantification

Single colonies of the expression strains were picked into 60 L of rich medium (e.g. LB broth) supplemented with 20 g/mL kanamycin sulfate in a 96-well plate (GE Life Sciences part 28403943). The cultures were grown at 37 degrees C. for 16 hours, then 15 L of culture was used to inoculate 600 µL of defined glucose-mineral media and 20 µg/mL kanamycin sulfate in a 96 well plate. The cultures were grown at 37 degrees C. for 48 hours, after which the supernatant was harvested by pelleting the cells with centrifugation and removing the residual culture liquid. The expression levels (concentration in mg/mL) of variant polypeptide hybrids having alpha-amylase activity were identified by LabChip (LC) analysis and corresponding expression plasmids were sequenced for verification.

Example 3: Red Starch and Residual Activity Assays

Quantitation of starch hydrolysis for the variant polypeptides containing alpha-amylase activity was measured using the Red Starch method as described by Megazyme, "Assay of Alpha-Amylase using Red-Starch" with the following modifications. 10 L of 1.33% red starch prepared in 50 mM HEPES, pH 8.0 buffer was reacted with 10 L enzyme diluted in 50 mM HEPES, pH 8.0 buffer at 25° C. The reaction was terminated after 10 minutes by the addition of 50 L of 200 proof ethanol. After vigorous mixing, the reaction was equilibrated for 10 minutes at room temperature followed by centrifugation at 1,200×g for 10 minutes. 40 L of the reaction was transferred and the solution absorption was read at 510 nm in a BioTek plate reader. Residual activity was calculated by comparing the activity of each enzyme as measured using the red starch assay before and after a heat challenge. A heat challenge was conducted on enzyme diluted in 50 mM HEPES, pH 8.0 buffer by first heating the sample to 80 degrees C. for 15 minutes, chilling at 4 degrees C. for 10 minutes, then holding at 24 degrees C. for 5 minutes before testing using the red starch assay at 25 degrees C.

Each enzyme/temperature pair was done in technical duplicates (25° C. done in triplicate or n=5), with two independent experiments run on different days. For residual activity plots, the reference for "100% activity" was the highest activity measurement across all temperatures. The result for the 80° C. heat challenge is shown in FIG. 1. It is clearly visible that replacing the C domain of SEQ ID NO:41 with the C domain of SEQ ID NO:40 resulting in an amylase having SEQ ID NO:54 (with additional mutations at the positions 430 and 454) greatly increases the thermostability. Using closely related C domains (like closely related to the C domain of SEQ ID NO: 40) gives rise to hybrids being also more stable than SEQ ID NO: 41, underlined by the results obtained with SEQ ID NO: 9.

Example 4: Enzyme Performance in Laundry Applications (Stain Removal)

Wash performance was measured for the hybrid amylases on cotton soiled with starch (stain types EMPA161 and CS28) purchased from Swissatest Testmaterilien AG and CFT (Center for Testmaterials B.V.). The amylase according to SEQ ID NO: 39 is used as reference for the other amylases being hybrid molecules. SEQ ID NO:54 is for example the hybrid of SEQ ID NO: 42 and SEQ ID NO: 44 containing a double deletion at the positions 183 and 184 and further mutations at the positions 430 and 454. Also other amylases chosen (SEQ ID NO: 5, SEQ ID NO: 11, SEQ ID NO: 17 and SEQ ID NO: 27) are hybrids with significant changed C-domains over SEQ ID NO:54.

Amylases were dosed at 0.05, 0.1, 0.2, or 0.4 ppm in 2.5 mM hard water (14° dH, deutsche Harte) plus 3.3 g/L detergent ES1 (Maranil DBS/LC LAS 5.5% w/w, Edenor coco fatty acid C12-C18 coco fatty acid 2.4% w/w, Lutensol AO7 AEO 5.4% w/w, Texapon N70 FAEO 5.4% w/w, 1,2 propylene glycol 6.0% w/w, ethanol 2.0% w/w, KOH 2.2% w/w) plus 3% sodium citrate resulting in an pH of 8.0-8.5. Wash was conducted by means of a Launder-O-meter (SDS Atlas) for 30 minutes at 40° C. Wash liquor was removed then the fabric was rinsed three times with water. The samples were dried overnight at room temperature. Wash performance was measured using digital image analysis of washed stains by means of a spectrophotometer (ELREPHPO, Datacolor; the average L*AB intensity was normalized to the detergent base without amylase; and then average of the four data points (0.05, 0.1, 0.2, or 0.4 ppm) is provided.

Wash performance on test stains CS 28 and EMPA 161 is shown as ddE to show the amylase specific effects (dE amy-dE detergent base).

| CS28 | Type | 0 ppm | | ddE | | |
| | | | 0.05 ppm | 0.1 ppm | 0.2 ppm | 0.4 ppm |
|---|---|---|---|---|---|---|
| Seq ID NO: 39 | Refer-ence | 0 | n.a. | 0.91 | 2.26 | 2.23 |
| Seq ID NO: 54 | Hybrid | 0 | 1.79 | 2.76 | 2.95 | 2.76 |
| Seq ID NO: 5 | Hybrid | 0 | 1.86 | 2.97 | 3.42 | 2.85 |
| Seq ID NO: 11 | Hybrid | 0 | 1.93 | 2.77 | 3.28 | 3.13 |
| Seq ID NO: 17 | Hybrid | 0 | 1.99 | 3.05 | 3.20 | 3.26 |
| Seq ID NO: 27 | Hybrid | 0 | 1.87 | 2.58 | 3.13 | 3.13 |

| EMPA161 | Type | 0 ppm | | ddE | | |
| | | | 0.05 ppm | 0.1 ppm | 0.2 ppm | 0.4 ppm |
|---|---|---|---|---|---|---|
| Seq ID NO: 39 | Refer-ence | 0 | 5.44 | 6.05 | 7.10 | 7.77 |
| Seq ID NO: 54 | Hybrid | 0 | 8.43 | 8.55 | 10.93 | 12.33 |
| Seq ID NO: 5 | Hybrid | 0 | 7.04 | 7.79 | 9.94 | 10.68 |
| Seq ID NO: 11 | Hybrid | 0 | 7.38 | 8.00 | 11.24 | 11.35 |
| Seq ID NO: 17 | Hybrid | 0 | 8.62 | 9.29 | 11.99 | 12.55 |
| Seq ID NO: 27 | Hybrid | 0 | 7.00 | 7.92 | 10.66 | 12.60 |

The results, as provided in the tables above, show that the hybrid amylase enzymes have an improved performance (stain removal) when compared to the parent enzyme SEQ ID NO: 39.

Example 5: Stability Testing by Heat Challenge

Hybrid enzymes of the invention can be stabilized by further changes in the amino acids sequences. This was tested by storing the variants at elevated temperature and measuring the residual activity after certain time.

Herefore, the enzymes were diluted to –20 µg/mL into 0.1 M Hepes pH 8.0 and challenged at 92° C. for 10 min, then chilled at 4° C. using a PCR machine. Unchallenged controls were kept at 4° C. To measure residual activity, challenged enzymes and controls were diluted 10 fold into 1% Red Starch prepared in 0.1 M Hepes pH 8.0 and 0.05% Tween20 following the manufacturer's instructions (Megazyme) and incubated at room temperature for 10 min. Reaction was quenched with two volumes of ice-cold ethanol, incubated for 10 min, then spun down. Supernatant was transferred into new plates and absorbance was read at 510 nm. Improvement Factor (IF) was calculated as the ratio between the specific variant and the parent SEQ ID NO:54.

The mutations are introduced in SEQ ID NO:54 using the numbering according to SEQ ID NO: 39.

| | IF |
|---|---|
| M9L | 1.80 |
| K179L | 2.08 |
| G186E | 2.80 |
| G186N | 2.18 |
| G186Q | 2.48 |
| G186S | 2.57 |
| N195F | 2.84 |
| I206L | 2.42 |
| G435R | 1.44 |
| S437A | 1.61 |
| E441D | 1.60 |
| Q485K | 1.52 |
| Seq ID NO: 54 | 1.00 |

Example 6: Storage of Hybrid Variants in Liquid Laundry Detergent

The stabilization of hybrid enzymes of the invention by further changes in the amino acids sequences was further tested by storing the variants in liquid detergent and measuring the residual activity after certain time.

Storage in liquid laundry detergent was done by incubating the amylases in a ES1-C detergent solution (Maranil DBS/LC LAS 5.5% w/w, Edenor C12-C18 coco fatty acid 2.4% w/w, Lutensol A07 AEO 5.5% w/w, Texapon N70 FAEO 5.5% w/w, 1,2 propylene glycol 6.0% w/w, ethanol 2.0% w/w, KOH 2.2% w/w and Na-citrate 3%, pH 8) including 1% of Bacillus lentus alkaline protease (BLAP) with R101E mutation and stored at 37° C. for 7 days. Samples were taken out at day 0 and 7 and diluted in 50 mM MOPS, pH7 before being analyzed with Infinity amylase reagent at room temperature. The activity is the slope at 405 nm calculated as the 5 point MaxV over 5 minutes. The improvement factor (IF) over the reference hybrid amylase SEQ ID NO: 54 is calculated by taking percent residual activity after storage of each variant and dividing it by the percent residual activity after storage of Seq ID NO: 54. The mutations are introduced in SEQ ID NO: 54 using the numbering according to SEQ ID NO: 39.

| | IF |
|---|---|
| K179L | 3.23 |
| G186E | 7.42 |
| G186N | 5.76 |
| G186S | 6.45 |
| G186Q | 6.89 |
| N195F | 4.92 |
| I206L | 4.22 |
| SEQ ID NO: 54 | 1 |

Example 7: Microscale Wash Tests for Hybrid Variants

Hybrids of the invention can be made more efficient in cleaning performance by minor changes in the amino acids sequences. This was tested by microscale wash trials.

Variants were used to wash aged corn starch stains (CS-126) in 3.3 g/L ES1_C (Lutensit A-LBS LAS 5.5% w/w, Edenor coco fatty acid C12-C18 coco fatty acid 2.4% w/w, Lutensol A07 AEO 5.5% w/w, Texapon N70 FAEO 5.5% w/w, 1,2 propylene glycol 6.0% w/w, ethanol 2.0% w/w, KOH 2.2% w/w and Na-citrate 3%, pH 8) with 2.78 mM hard water (15.5° dH, deutsche Harte) at room temperature at 0.02, 0.05 and 0.1 ppm of amylase added to the wash for 60 minutes before being rinsed for 5 min under running water, dried and measured for intensity of the reflected light as an average of the RGB values. A ratio of the performance of specific variants vs. that of SEQ ID NO:54 was made and a number above 1 indicates higher performance.

The mutations are introduced in SEQ ID NO:54 using the numbering according to SEQ ID NO: 39.

| Mutation | 0.02 ppm | 0.1 ppm |
|---|---|---|
| K179L | 1.57 | 1.69 |
| G186E | 2.15 | 1.76 |
| N195F | 1.54 | 1.68 |
| I206L | 1.58 | 1.69 |
| SEQ ID NO: 54 | 1.00 | 1.00 |

The invention claimed is:

1. An isolated, synthetic, or recombinant polypeptide having alpha-amylase activity comprising an A and B domain and a C domain wherein the amino acid sequence of the A and B domain is at least 90% identical to the amino acid sequence of SEQ ID NO: 42 and the amino acid sequence of the C domain is at least 90% identical to the amino acid sequence of SEQ ID NO: 44.

2. The polypeptide according to claim 1 having alpha-amylase activity consisting of an A and B domain and a C domain wherein the amino acid sequence of the A and B domain is at least 90% identical to the amino acid sequence of SEQ ID NO: 42 and the amino acid sequence of the C domain is at least 90% identical to the amino acid sequence of SEQ ID NO: 44.

3. The polypeptide according to claim 1, wherein the A and B domain has at least 92%, sequence identity to the A and B domain having the amino acid sequence of SEQ ID NO: 42.

4. The polypeptide according to claim 1, wherein the C domain has at least 92% sequence identity to the C domain having the amino acid sequence of SEQ ID NO: 44.

5. The polypeptide according to claim 1 comprising a substitution, deletion, and/or insertion at one or more positions.

6. The polypeptide according to claim 1 comprising the sequence TQXDYLDHPD-VIGWTREGDXXHXXSGLAXLMSDGPXGXKWMX VGKNNAGEXWXDITGNQTNTVTINXDGXGQFXVXX GSXSIYXQX(SEQ ID NO: 56), wherein X can be any amino acid.

7. The polypeptide according to claim 1, wherein the polypeptide has one or more amino acid residues selected from the group consisting of 402R, H; 419S, G, D; 420V, I; 422, A, V; 423N, D, G, K; 428T, A; 435G, R, E; 437S, A; 441N, E, D; 444K, E; 450V, I; 452Y, H, R; 466K, R; 469W, S; 473H, Q, R; 475S, N; 476G, E; 479V, A; 483V, I; and 485R, Q, K according to the numbering of SEQ ID NO: 39.

8. The polypeptide according to claim 1 comprising a substitution at one or more positions selected from the group consisting of 430 and 454 according to the numbering of SEQ ID NO: 39.

9. The polypeptide according to claim 1 comprising an amino acid residue at one or more of the amino acid positions selected from the group consisting of 401, 403, 405, 411, 413, 415, 424, 426, 428, 432, 455, 477, 479 and 481 (according to the numbering of SEQ ID NO: 39) as present in SEQ ID NO: 39.

10. The polypeptide according to claim 1 comprising an amino acid residue at one or more of the amino acid positions selected from the group consisting of 309, 313, 347, 348, 350, 351, 354, 355, 358, 359, 388, 389, 392 and 396 (according to the numbering of SEQ ID NO: 39) as present in SEQ ID NO: 40.

11. The polypeptide according to claim 1 comprising a deletion of one or more amino acids corresponding to positions 181, 182, 183 and 184 corresponding to the numbering of SEQ ID NO: 39.

12. The polypeptide according to claim 1 comprising a substitution at one or more positions selected from the group consisting of 9, 130, 195, 206, 244, 202, 179, 181, 186, and 190 according to the numbering of SEQ ID NO: 39.

13. The polypeptide according to claim 1 comprising: an amino acid sequence having at least 90% sequence identity to SEQ ID NO:54.

14. The polypeptide according to claim 1, wherein the amylase has an increase in expression, activity, thermostability, stability, performance in laundry, specific activity, substrate specificity, pH-dependent activity, pH-dependent stability, oxidative stability, Ca2+ dependency, or any combination thereof compared to the amylase having the amino acid sequence of SEQ ID NO: 39 or SEQ ID NO: 40.

15. A composition comprising the isolated, synthetic, or recombinant polypeptide having alpha-amylase activity according to claim 1.

16. The composition of claim 15, further comprising at least one second enzyme selected from the group consisting of: a second amylase, a lipase, a protease, a cellulase, a laccase, a mannanase, a pectinase, xylanase, and a nuclease.

17. A method of making the isolated, synthetic, or recombinant polypeptide having alpha-amylase activity according to claim 1, comprising: providing a nucleic acid sequence encoding the polypeptide, transforming the nucleic acid sequence into an expression host, cultivating the expression host to produce the polypeptide, and optionally purifying the polypeptide.

18. A method of preparing a dough or a baked product prepared from the dough, the method comprising adding the isolated, synthetic, or recombinant polypeptide having alpha-amylase activity according to claim 1 to the dough and baking it.

\* \* \* \* \*